United States Patent
Machatha et al.

(10) Patent No.: US 11,911,385 B1
(45) Date of Patent: Feb. 27, 2024

(54) METHOTREXATE TREATMENT METHODS

(71) Applicant: Aldeyra Therapeutics, Inc., Lexington, MA (US)

(72) Inventors: Stephen Gitu Machatha, Wilmington, MA (US); Dean Eliott, Carlsbad, CA (US); Tomasz Stryjewski, Somerville, MA (US)

(73) Assignee: ALDEYRA THERAPEUTICS, INC., Lexington, MA (US)

( * ) Notice: Subject to any disclaimer, the term of this patent is extended or adjusted under 35 U.S.C. 154(b) by 0 days.

(21) Appl. No.: 18/081,546

(22) Filed: Dec. 14, 2022

(51) Int. Cl.
| | |
|---|---|
| A61K 31/519 | (2006.01) |
| A61K 9/00 | (2006.01) |
| A61P 27/02 | (2006.01) |
| A61K 47/26 | (2006.01) |

(52) U.S. Cl.
CPC .......... *A61K 31/519* (2013.01); *A61K 9/0019* (2013.01); *A61K 9/0048* (2013.01); *A61K 47/26* (2013.01); *A61P 27/02* (2018.01)

(58) Field of Classification Search
CPC ... A61K 31/519; A61K 9/0019; A61K 9/0048
See application file for complete search history.

(56) References Cited

U.S. PATENT DOCUMENTS

| | | | |
|---|---|---|---|
| 7,166,570 B2 | 1/2007 | Hunter et al. | |
| 9,259,427 B2 | 2/2016 | Tierney et al. | |
| 10,098,884 B2 | 10/2018 | Eliott et al. | |
| 2004/0253243 A1 | 12/2004 | Epstein et al. | |
| 2005/0255144 A1 | 11/2005 | Schultz | |
| 2006/0073182 A1 | 4/2006 | Wong et al. | |
| 2006/0258698 A1 | 11/2006 | Mudumba et al. | |
| 2008/0241221 A1 | 10/2008 | Whitcup et al. | |
| 2009/0081277 A1 | 3/2009 | Robinson et al. | |
| 2010/0087474 A1 | 4/2010 | Kaushal et al. | |
| 2011/0200662 A1 | 8/2011 | Glazier | |
| 2014/0105956 A1 | 4/2014 | Banerjee et al. | |
| 2019/0054023 A1 | 2/2019 | Seaman et al. | |
| 2022/0370460 A1 | 11/2022 | Eliott et al. | |
| 2023/0017743 A1 | 1/2023 | Eliott et al. | |
| 2023/0018197 A1 | 1/2023 | Eliott et al. | |

FOREIGN PATENT DOCUMENTS

| | | |
|---|---|---|
| WO | WO-2014033184 A1 | 3/2014 |
| WO | WO-2014074823 A1 | 5/2014 |
| WO | WO-2016019165 A1 | 2/2016 |
| WO | WO-2018201146 A1 | 11/2018 |

(Continued)

OTHER PUBLICATIONS

Benner et al., "Intravitreal methotrexate for the treatment of proliferative vitreoretinopathy," BMJ Open Ophthalmol. 2019;4(1):e000293.

(Continued)

*Primary Examiner* — Carlos A Azpuru
(74) *Attorney, Agent, or Firm* — Dechert LLP; Andrea L. C. Reid; Joseph W. Arico

(57) ABSTRACT

The present disclosure provides compositions of methotrexate for ocular administration, including intravitreal administration, and use of the formulations for treating proliferative vitreoretinopathy (PVR), uveitis, macular edema, and uveitic macular edema.

20 Claims, 3 Drawing Sheets

(56) References Cited

FOREIGN PATENT DOCUMENTS

| WO | WO-2019169306 A1 |   | 9/2019 |
|----|------------------|---|--------|
| WO | 2021/051003 A1   | * | 3/2021 |
| WO | WO-2021051003 A1 |   | 3/2021 |
| WO | WO-2021173929 A1 |   | 9/2021 |

OTHER PUBLICATIONS

Gonzalez-Tello et al., "Density and Viscosity of Concentrated Aqueous Solutions of Polyethylene Glycol," J Chem Eng Data. 1994; 39(3):611-614.

Kwon et al., "Retinal Detachment and Proliferative Vitreoretinopathy," Dev Ophthalmol. 2016;55:154-62.

Liu et al., "Pharmacological clearance of misfolded rhodopsin for the treatment of RHO-associated retinitis pigmentosa," FASEB J. Aug. 2020;34(8):10146-10167.

Owen et al., "Preliminary Results of Treatment With Intravitreal Methotrexate in Patients With Macula Oedema Secondary to Uveitis," Invest Ophthalmol Vis Sci. 2012; 53(14):1179(meeting abstract).

PCT International Search Report and Written Opinion from PCT/US2020/050565, dated Dec. 22, 2020.

Regupathi et al., "Densities and Viscosities of Poly(ethylene glycol) 4000 + Diammonium Hydrogen Phosphate + Water Systems," J Chem Eng Data. 2009; 54(3):1100-1106.

Roche Diagnostics GbbH, "Tween 20 Datasheet: Poly(oxyethylene)x-sorbitane-monolaurate," ; Sigma-Aldrich. Retrieved Nov. 19, 2020: https://www.sigmaaldrich.com/catalog/product/roche/11332465001?lang=en&region=US#:~: text=Tween%2020%>.

Sadaka et al., "Intravitreal methotrexate infusion for proliferative vitreoretinopathy," Clin Ophthalmol. 2016;10:1811-1817.

Sarfare et al., "Biocompatibility of a Synthetic Biopolymer for the Treatment of Rhegmatogenous Retinal Detachment," J Clin Exp Ophthalmol. 2015;6(5):475.

Schwartz et al., "Tamponade in surgery for retinal detachment associated with proliferative vitreoretinopathy," Cochrane Database Syst Rev. 2014;2(2):CD006126.

Yeh and Wilson, "Combination intravitreal rituximab and methotrexate for massive subretinal lymphoma," Eye (Lond). 2010;24(10):1625-7.

Alabi, Rolake, MD, Ph.D et al., "Rescue Intravitreal Methotrexate Treatment Following Early Recognition of Proliferative Vitreoretinopathy," Retinal Cases and Brief Reports, DOI: 10.1097/ICB.0000000000001252, Ophthalmic Communications Society, Inc., Jan. 22, 2022 (13 Pages).

Banerjee, Philip J., et al., "Slow-Release Dexamethasone in Proliferative Vitreoretinopathy," Ophthalmology, vol. 124, No. 6, Jun. 2017, pp. 757-767.

Ma, Wei-Li et al., "Clinical Outcomes of Primary Intraocular Lymphoma Patients Treated With Front-Line Systemic High-Dose Methotrexate and Intravitreal Methotrexate Injection," Ann Hematol, 2016, DOI 10.1007/s00277-015-2582-x, vol. 95, pp. 593-601.

Roca, Jose A. et al., "Adjunctive Serial Post-Operative Intravitreal Methotrexate Injections in the Management of Advanced Proliferative Vitreoretinopathy," Retinal Disorders, Graefe's Archive for Clinical and Experimental Ophthalmology, DOI 10.1007/s00417-021-05206-z, Springer Nature 2021 (5 Pages).

Schiff, William M. et al., "Safety and Efficacy Assessment of Chimeric Ribozyme to Proliferating Cell Nuclear Antigen to Prevent Recurrence of Proliferative Vitreoretinopathy," Arch Ophthalmol, vol. 125, No. 9, Sep. 2007, pp. 1161-1167.

Wa, Christianne April et al., "Post-Operative Intravitreal Methotrexate Injections After Recurrent Retinal Detachment Repair Can Reduce the Risk and Progress of Proliferative Vitreoretinopathy," Investigative Ophthalmology & Visual Science, Jun. 2020, vol. 61, No. 1413 (2 Pages).

Hardwig et al., "The Safety of Intraocular Methotrexate in Silicone-Filled Eyes," Retina, Lippincott, Williams & Wilkins, Aug. 31, 2008, vol. 28, No. 8, pp. 1082-1086.

Idrees et al., "Proliferative Vitreoretinopathy: a Review," International Opthalmogy Clinics, Jan. 1, 2019, pp. 221-240.

* cited by examiner

METHOTREXATE TREATMENT METHODS

BACKGROUND

Diseases and disorders of the eye include uveitic macular edema (uveitic ME), retinitis pigmentosa (RP), proliferative vitreoretinopathy (PVR), and primary vitreoretinal lymphoma (PVRL).

Uveitis is a form of eye inflammation that affects the uvea, which is the middle layer of tissue in the eye. An eye with uveitis will have redness, possibly accompanied by eye pain, light sensitivity, and/or blurred or decreased vision. The immune system may be responding to an infection in the eye or attacking healthy eye tissue while fighting an infection elsewhere in the body. Other causes include injury, autoimmune diseases, and/or inflammatory diseases. The cause of uveitis is often unknown, and the onset and worsening of symptoms can be swift.

Macular edema (ME) is the most common structural complication and cause of visual impairment and legal blindness in uveitis patients. Traditional approaches to the treatment of uveitic ME have included the use of regional corticosteroid therapy, delivered periocularly, including posterior sub-Tenon's and orbital floor injections, or via the intravitreal route. While corticosteroid injections may reduce ME and improve vision, the effect is often variable with a limited duration. Persistent macular edema is a common occurrence and often requires repeated intravitreal injections of corticosteroids, which expose eyes to a significant risk of increased intraocular pressure ocular and cataract development. The often refractory nature of uveitic ME and its impact on visual function underscores the need to identify effective alternative medical therapeutic options.

Retinitis pigmentosa (RP) is a group of rare eye diseases that affect the retina. Over time, cells in the retina break down, resulting in vision loss. RP is usually hereditary, and typically symptoms begin in childhood. For example, parents may notice that the child has reduced night vision. Other causes are medication side effects, infection, or eye injury.

Proliferative vitreoretinopathy (PVR) is a clinical syndrome that occurs after rhegmatogenous retinal detachment, such as caused by a break in the retina (e.g., retinal tear or retinal hole) and its surgical repair. The pathogenesis of PVR involves the release of cells into the vitreous cavity (extraretinal cells) where they replicate and form periretinal fibrocellular membranes on the inner and/or outer surfaces of the retina, creating shortening of the retina and retinal traction. PVR is characterized by intraretinal fibrosis and reduced elasticity, which leads to tractional elevation of the retina and subsequently new retina breaks and recurrent retinal detachment. PVR can occur in untreated eyes with retinal detachment or after retinal procedures such as retinal cryopexy, laser retinopexy, pneumatic retinopexy, scleral buckle and/or pars plana vitrectomy. The prevalence of PVR varies widely but is estimated to range about 5 to 12% of all rhegmatogenous retinal detachment cases (Kwon et al., Dev Ophthalmol., 2016; 55:154-62). PVR and its associated retinal traction is one of the main reasons for failure (i.e., recurrent retinal detachment) of initially successful repairs of retinal detachment and is present in approximately 75% of failed retinal detachment repairs (Sadaka et al., Clinical Ophthalmology, 2016; 10 1811-1817).

Retinal detachment surgery can include scleral buckling, pneumatic retinopexy, and pars plana vitrectomy (PPV). Pneumatic retinopexy involves injecting gas into the vitreous cavity while PPV for retinal detachment involves removal of the vitreous and its replacement with a tamponade agent, such as silicone oil or gas. Tamponade agents provide surface tension across retinal breaks, preventing further fluid flow into the subretinal space until the retinopexy (photocoagulation or cryopexy) provides a permanent seal. For complex detachments involving PVR, silicone oil is often used. Commonly used viscosities of silicone oils include 1,000 and 5,000 centistokes. Silicone oils have a lower specific gravity (0.97 g/mL) than vitreous (1.005-1.008 g/mL), and as a result, they float in the vitreous cavity. Similarly, gases also float in the vitreous cavity due to their very low specific gravities (~0.001 g/mL) and they have a much greater buoyancy than silicone oils. Heavier silicone oils (HSOs) and perfluorocarbon liquids have been used for inferior retinal breaks because the lighter silicone oils and gases may be less effective tamponade for retinal breaks at these locations. Given the prevalence of PVR following retinal detachment and retinal detachment surgery, anti-inflammatory and immunosuppressive agents have been administered to control PVR and reduce the failure rates of PPV. Use of anti-inflammatory or immunosuppressive agents may be beneficial for subjects at higher risk of PVR.

Methotrexate (MTX) is an antineoplastic antimetabolite with immunosuppressant properties and inhibits enzymes requiring folate as a cofactor, including enzymes involved in nucleotide biosynthesis necessary for DNA replication. MTX has been used to treat chronic inflammatory and fibrotic conditions. Studies of intravitreal MTX administration following retinal reattachment surgery show promise in reducing the incidence of retinal detachment following surgery (Benner et al., BMJ Open Ophth., 2019; 4:e000293; Sadaka et al., Clinical Ophthalmology, 2016; 10:1811-1817). Desirable are formulations of MTX for treating PVR following retinal detachment, particularly for cases when silicone oil is used as the preferred tamponade agent, as well as for treating other ocular disorders amenable to treatment with MTX, such as uveitic macular edema (uveitic ME), retinitis pigmentosa (RP), and proliferative vitreoretinopathy (PVR).

SUMMARY OF THE INVENTION

In one aspect, the present invention provides a method of treating proliferative vitreoretinopathy (PVR), comprising administering intravitreally to a subject in need thereof a composition comprising methotrexate at a concentration of about 5 mg/mL to about 12 mg/mL; sucrose at a concentration of about 7% w/v to about 12% w/v; and a phosphate buffer; wherein the volume of composition administered is about 20 µL to about 300 µL, and the incidence of secondary punctate keratitis in the subject is reduced.

In some embodiments, the incidence of secondary punctate keratitis in the subject is reduced by about 10% to 50% compared to a similar subject administered a non-GMP composition of methotrexate or a composition comprising methotrexate in a volume greater than 300 µL.

In some embodiments, the incidence of secondary punctate keratitis in the subject is reduced by about 20% to 40% compared to a similar subject administered a non-GMP composition of methotrexate or a composition comprising methotrexate in a volume greater than 300 µL.

In some embodiments, the incidence of secondary punctate keratitis in the subject is reduced by about 40% compared to a similar subject administered a non-GMP composition of methotrexate or a composition comprising methotrexate in a volume greater than 300 µL.

In some embodiments, the method produces a statistically significant (p<0.05) reduction in incidence of punctate keratitis across a representative group of subjects.

In some embodiments, the volume of composition administered is about 20 µL to about 80 µL.

In some embodiments, the volume of composition administered is about 50 µL±10 µL.

In some embodiments, the method provides an improved incidence of intraocular pressure (IOP) elevation (hypotony) compared to a similar subject administered a non-GMP composition of methotrexate or a composition comprising methotrexate in a volume greater than 300 µL.

In some embodiments, the method provides a reduced incidence of retinal re-detachments due to PVR requiring re-operation within 6 months vs. routine surgical care.

In some embodiments, the method provides improved visual acuity vs. routine surgical care.

In some embodiments, the method provides an improvement in macular thickness, epiretinal membrane formation, and/or hypotony (elevated IOP) vs. routine surgical care.

In some embodiments, the composition has a transit rate of less than 10 min in 1 mL of silicone oil (SiO) having a viscosity of at least 1000 centistoke and depth of 1 cm.

In some embodiments, the transit rate is less than 8 min.

In some embodiments, the SiO is polydimethyl siloxane 5000 centistoke oil or polydimethyl siloxane 1000 centistoke oil.

In some embodiments, the methotrexate is at a concentration of about 7 mg/mL to about 9 mg/mL.

In some embodiments, the composition has a density of about 1.0 to about 1.20 g/cm$^3$ at 20° C.

In some embodiments, the sucrose is at a concentration of about 7.0% w/v to about 8% w/v.

In some embodiments, the phosphate buffer is sodium phosphate dibasic.

In some embodiments, the sodium phosphate dibasic is at a concentration of about 0.05 mg/mL to 0.3 mg/mL.

In some embodiments, the composition has a pH of about 6 to about 8.

In some embodiments, the subject has a prior history of one or more of: chronic ocular inflammation, infectious retinitis, multiple retinal detachments, large retinal breaks or giant retinal tears, multiple retinal breaks, ocular trauma, retinal detachment associated with vitreous hemorrhage, and choroidal detachment; and combinations thereof.

In some embodiments, each dose of methotrexate is independently about 200 µg to about 600 µg, or about 300 µg to about 500 µg.

In some embodiments, each dose of methotrexate is independently about 200 µg, about 300 µg, about 400 µg, or about 500 µg.

In some embodiments, the composition is administered before, during, or within 24 hrs of retinal detachment surgery.

In some embodiments, the composition is administered before, during, or within 24 hrs of retinal detachment surgery, followed by administration about once a week.

In some embodiments, the composition is administered before, during, or within 24 hrs of retinal detachment surgery, followed by administration about once a week for about 6-12 weeks.

In some embodiments, after the administration about once a week, the composition is then administered about once every 2 weeks for up to 24 weeks.

In some embodiments, the administration about once every 2 weeks continues for about 8 weeks (about 4 administrations over about 8 weeks).

In some embodiments, the composition is administered before, during, or after retinal detachment surgery, followed by administration of the composition one, two, three, four, five, six, seven, or eight times a month for up to 6 months.

In another aspect, the present invention provides a method of treating proliferative vitreoretinopathy (PVR) comprising administering to a subject in need thereof a composition comprising methotrexate at a concentration of about 8 mg/mL; sucrose at a concentration of about 7.5% w/v, and a phosphate buffer at a pH of about 7.9 to about 9.0; wherein the volume of composition administered is 50 µL±10 µL; and the incidence of secondary punctate keratitis in the subject is substantially reduced.

In some embodiments, the osmolality of the composition is about 250 to about 350 mOsm.

In some embodiments, the composition has a transit rate of less than 10 min in 1 mL of silicone oil (SiO) having a viscosity of at least 1000 centistoke and depth of 1 cm.

In some embodiments, the transit rate is less than 8 min.

In some embodiments, the SiO is polydimethyl siloxane 5000 centistoke oil or polydimethyl siloxane 1000 centistoke oil.

In some embodiments, the composition has a density of about 1.0 to about 1.20 g/cm$^3$ at 20° C.

In another aspect, the present invention provides a method of treating an ocular disease selected from intraocular lymphoma, uveitis, macular edema, uveitic macular edema, and retinitis pigmentosa (RP), comprising administering intravitreally to a subject in need thereof a composition comprising methotrexate at a concentration of about 5 mg/mL to about 12 mg/mL; sucrose at a concentration of about 7% w/v to about 12% w/v; and a phosphate buffer; and wherein the volume of composition administered is about 20 µL to about 300 µL.

In some embodiments, the ocular disease is retinitis pigmentosa (RP).

In some embodiments, the ocular disease is intraocular lymphoma.

In some embodiments, the intraocular lymphoma treated is primary vitreoretinal lymphoma (PVRL).

In some embodiments, the intraocular lymphoma is accompanied by cerebral nervous system lymphoma (PCNSL).

In some embodiments, the intraocular lymphoma is diffuse large B-cell lymphoma.

In some embodiments, the ocular disease is uveitis.

In some embodiments, the ocular disease is macular edema or uveitic macular edema.

In some embodiments, the incidence of secondary punctate keratitis in the subject is reduced by about 10% to 50% compared to a similar subject administered a non-GMP composition of methotrexate or a composition comprising methotrexate in a volume greater than 300 µL.

In some embodiments, the incidence of secondary punctate keratitis in the subject is reduced by about 20% to 40% compared to a similar subject administered a non-GMP composition of methotrexate or a composition comprising methotrexate in a volume greater than 300 µL.

In some embodiments, the incidence of secondary punctate keratitis in the subject is reduced by about 40% compared to a similar subject administered a non-GMP composition of methotrexate or a composition comprising methotrexate in a volume greater than 300 µL.

In some embodiments, the method produces a statistically significant (p<0.05) reduction in incidence of punctate keratitis across a representative group of subjects.

In some embodiments, the volume of composition administered is about 20 μL to about 80 μL.

In some embodiments, the volume of composition administered is about 50 μL±10 μL.

In some embodiments, the method provides an improved incidence of intraocular pressure (IOP) elevation (hypotony) compared to a similar subject administered a non-GMP composition of methotrexate or a composition comprising methotrexate in a volume greater than 300 μL.

In some embodiments, the method provides improved visual acuity vs. routine surgical care.

In some embodiments, the method provides an improvement in macular thickness, epiretinal membrane formation, and/or hypotony (elevated IOP) vs. routine surgical care.

In some embodiments, the methotrexate is at a concentration of about 7 mg/mL to about 9 mg/mL.

In some embodiments, the sucrose is at a concentration of about 7.0% w/v to about 8% w/v.

In some embodiments, the phosphate buffer is sodium phosphate dibasic.

In some embodiments, the sodium phosphate dibasic is at a concentration of about 0.05 mg/mL to 0.3 mg/mL.

In some embodiments, the composition has a pH of about 6 to about 8.

In some embodiments, the dose of methotrexate is about 200 μg to about 600 μg, or about 300 μg to about 500 μg.

In some embodiments, each dose of methotrexate is independently about 200 μg, about 300 μg, about 400 μg, or about 500 μg.

In some embodiments, the composition is administered intravitreally once every 2 months, once every 4 weeks (month), once every two weeks, once a week, two times a week, three times a week, or four times a week.

In one aspect, the present invention provides a method of treating retinitis pigmentosa (RP), comprising administering to a subject in need thereof a composition comprising methotrexate at a concentration of about 8 mg/mL; sucrose at a concentration of about 7.5% w/v, and a phosphate buffer at a pH of about 7.9 to about 9.0; wherein the volume of composition administered is 50 μL±10 μL; and the incidence of secondary punctate keratitis in the subject is substantially reduced.

In some embodiments, the incidence of secondary punctate keratitis in the subject is reduced by about 10% to 50% compared to a similar subject administered a non-GMP composition of methotrexate or a composition comprising methotrexate in a volume greater than 300 μL.

In some embodiments, the incidence of secondary punctate keratitis in the subject is reduced by about 20% to 40% compared to a similar subject administered a non-GMP composition of methotrexate or a composition comprising methotrexate in a volume greater than 300 μL.

In some embodiments, the incidence of secondary punctate keratitis in the subject is reduced by about 40% compared to a similar subject administered a non-GMP composition of methotrexate or a composition comprising methotrexate in a volume greater than 300 μL.

In some embodiments, the method produces a statistically significant (p<0.05) reduction in incidence of punctate keratitis across a representative group of subjects.

In some embodiments, the volume of composition administered is about 20 μL to about 80 μL.

In some embodiments, the volume of composition administered is about 50 μL±10 μL.

In some embodiments, the composition is administered once every two months, once a month, twice a month, three times a month, or once a week.

In some embodiments, the composition is administered once a month or twice a month.

In some embodiments, each dose of methotrexate is independently about 200 μg to about 600 μg, or about 300 μg to about 500 μg.

In some embodiments, each dose of methotrexate is independently about 200 μg, about 300 μg, about 400 μg, or about 500 μg.

In some embodiments, the composition comprising methotrexate is manufactured according to Good Manufacturing Practice (GMP).

DETAILED DESCRIPTION 1.1. Exemplary Methotrexate Compositions

Figure 1:
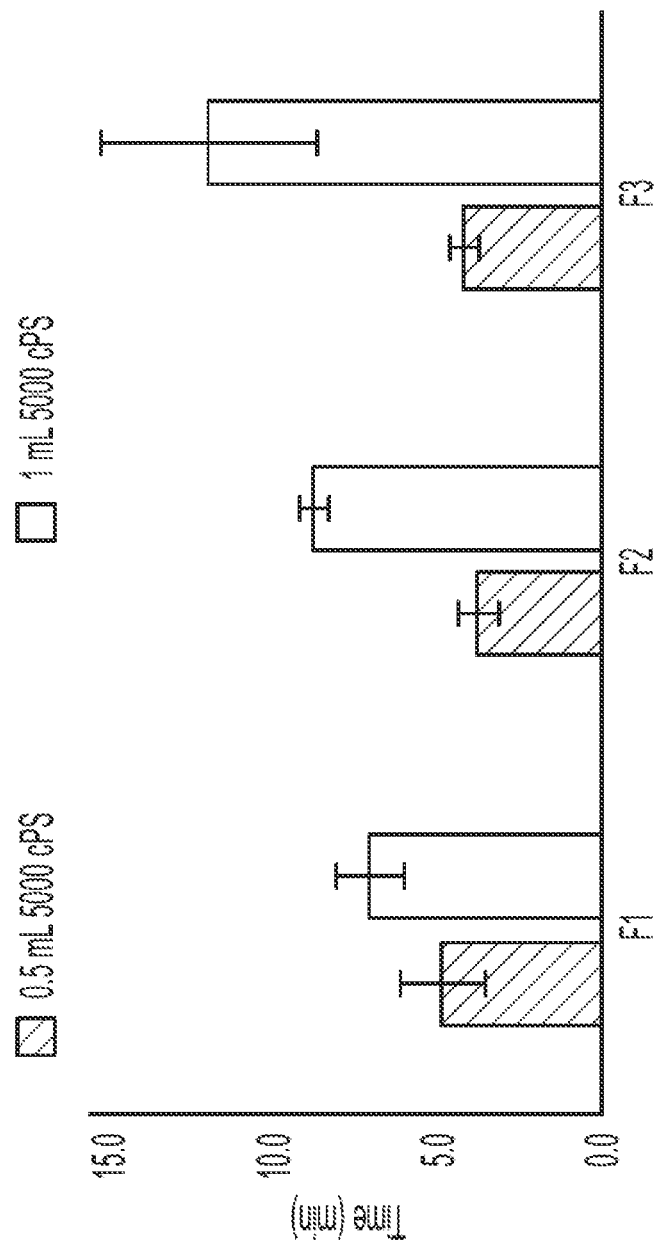
FIG. 1 illustrates the properties of formulations F1, F2, and F3 in transiting through polydimethyl siloxane 5000 centistoke oil to reach the bottom of the silicone oil layer, i.e., oil-buffer interface, of a non-miscible silicone oil/buffer mixture.
Figure 2:
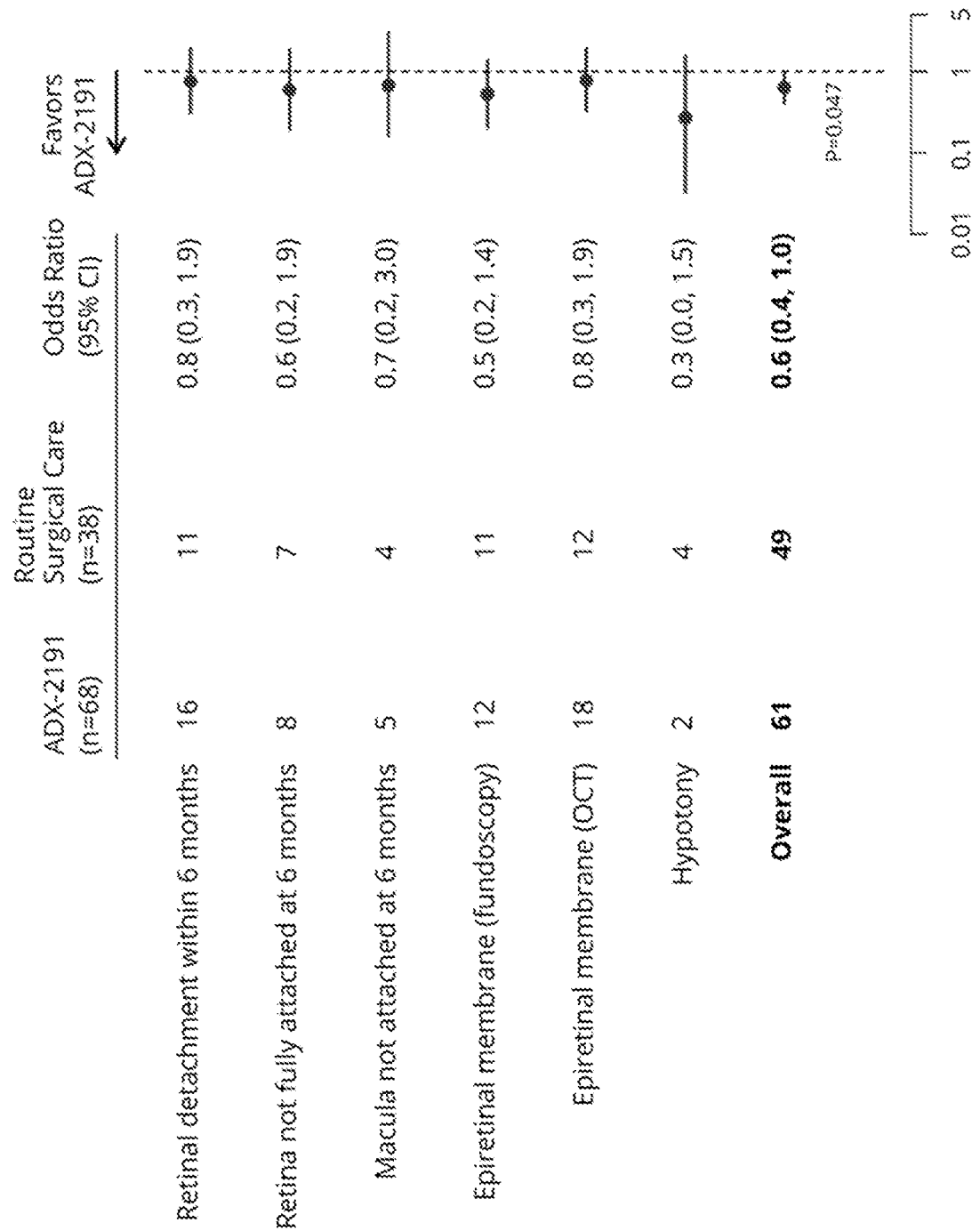
FIG. 2 illustrates the dichotomous endpoints are numerically in favor of ADX-2191.
Figure 3:
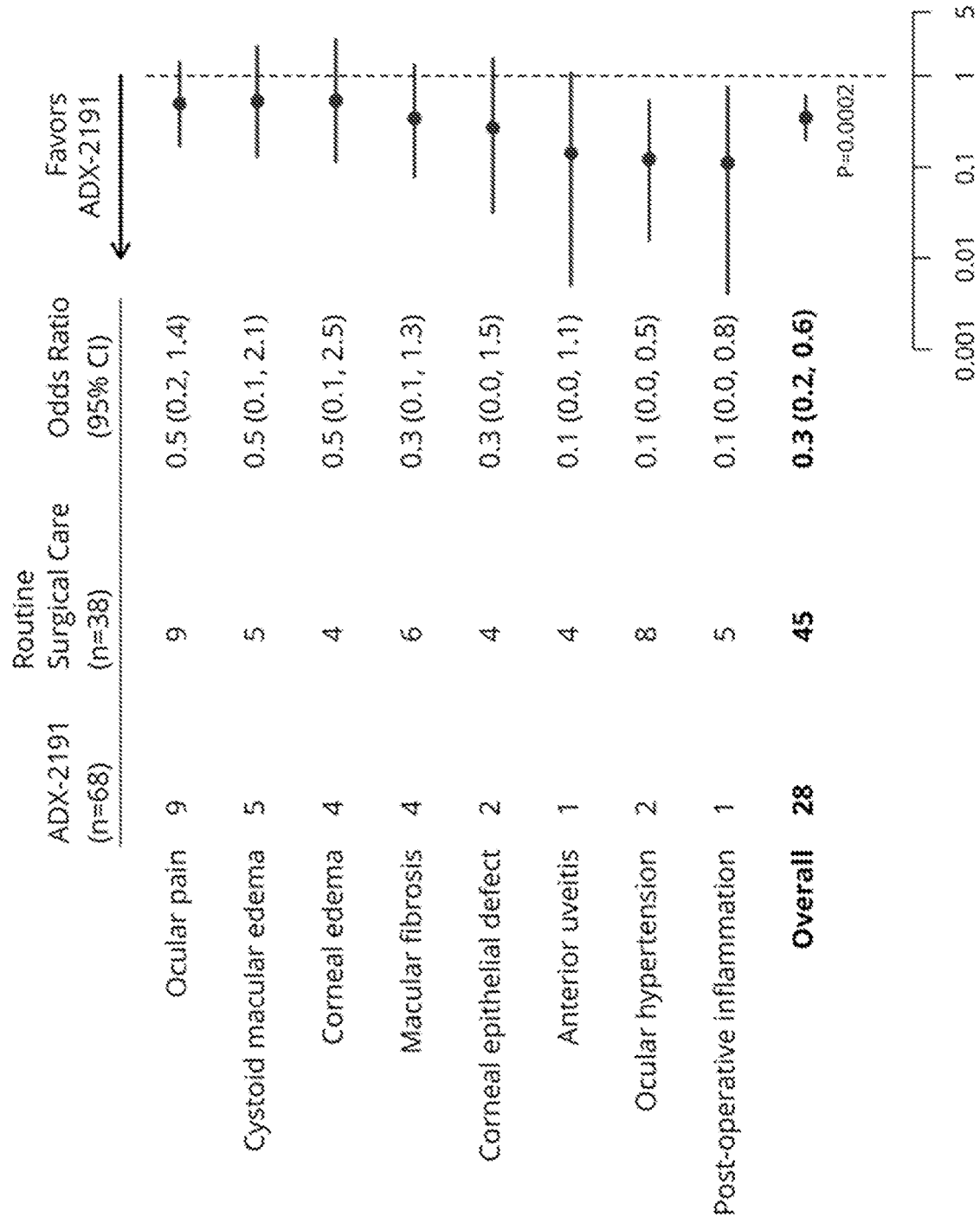
FIG. 3 illustrates that ADX-2191 is Numerically Favorable to Routine Surgical Care for Additional Key Safety Endpoints.

The present disclosure provides compositions of methotrexate (MTX), or a pharmaceutically acceptable salt thereof, for preventing, reducing the risk of, or treating ocular diseases such as proliferative vitreoretinopathy (PVR), intraocular lymphoma (e.g., primary vitreoretinal lymphoma), uveitis, macular edema, uveitic macular edema, retinitis pigmentosa (RP), and intraocular inflammation. The presently described compositions of MTX include sterile, non-compounded formulations of methotrexate designed to meet the unique requirements of intravitreal administration for specific rare retinal diseases, including primary vitreoretinal lymphoma and proliferative vitreoretinopathy. In some embodiments, a provided MTX intravitreal formulation is designed to be vitreous-compatible and optimized for excipient composition, viscosity, density, tonicity, pH, active ingredient concentration, and volume of administration.

The present disclosure provides methods of treating an ocular disease with compositions comprising methoxtrexate. In some embodiments, the ocular disease is a primary disease or disorder of the eye. In other embodiments, the ocular disease is a secondary disease or disorder of the eye that is undesirable side effect of treatment of a primary disease of the eye.

The compositions of the present invention may be administered intravitreally as, without limitation, an aqueous injection, a suspension, an emulsion, a solution, a gel or in a sustained release or extended release implant, either biodegradable or non-biodegradable.

It has now been found that treatment of certain ocular disorders with intravitreal methotrexate (MTX) results in fewer ocular side effects than the current standard of care, e.g., routine surgical care and/or treatment with ranibizumab or corticosteroids. In particular embodiments, the treatments result in less intraocular pressure (IOP) elevation and reduced incidence of punctate keratitis as a complication of PVR.

In one aspect, methods of treating ocular diseases and disorders disclosed herein comprise administration of low-volume injectable compositions, optionally with specific higher viscosities. Such methods have been found to deliver an effective dose of methotrexate with reduced undesirable side effects and complications. ADX-2191 (methotrexate) injection, USP is presented as 400 μg/0.05 mL; the volume of ADX-2191 is 0.05 mL, which is half of the 0.1 mL injection volume administered of compounded methotrexate. The smaller methotrexate injection volume reduces the potential for intraocular pressure (IOP) elevation, and injection site reflux, thereby potentially reducing rates of ocular hypertension and topical methotrexate toxicity leading to keratitis. Of note, in Study ADX-2191-PVR-001, the rate of ocular hypertension was lower in ADX-2191-treated eyes than in eyes with no injection Further, the most commonly reported TEAEs considered related to ADX-2191 in PVR were punctate keratitis (8 patients [11.8%]) and keratitis (5 patients [7.4%]), well-known side effects of intravitreal methotrexate, occurred at a much lower frequency than what has been reported in studies with compounded methotrexate (Frenkel et al. 2008 [26 patients, 100%], Habot-Wilner et al. 2021 [81 patients, 100%], Ma et al. 2016 [19 patients, 58%]). In Study ADX-2191-PVR-001, there were also no cases of toxic anterior segment syndrome which has been previously reported with intravitreal injection of compounded methotrexate (Habot-Wilner et al. 2021).

The present disclosure provides a composition comprising methotrexate (MTX), and a density enhancing agent. In some embodiments, the composition is characterized by a transit time of less than 10 min through a silicone oil (SiO) of 1 cm depth. In some embodiments, the SiO is SiO used in treatment of retinal detachment. In some embodiments, the SiO is SiO having a viscosity of at least 1000 centistoke, e.g., polydimethyl siloxane having viscosity of 1000 centistoke. In some embodiments, the SiO is SiO having a viscosity of about 5000 centistoke. In some embodiments, the SiO is polydimethyl siloxane having a viscosity of about 5000 centistoke.

In some embodiments, the density enhancing agent is selected from sucrose, trehalose, glucose, carbopol, polyvinyl acetate, polyvinyl alcohol (PVA), polyvinylpyrrolidone (PVP), carboxymethylcellulose, hydroxypropyl methylcellulose, hydroxypropyl cellulose, hydroxyethyl cellulose, polyethylene glycol (PEG), glycerol, poly(lactide) (PLA), poly(lactide-co-glycolide) (PLGA), polyglycolide (PGA), polyhydroxybutyric acid, polycaprolactone, polyvalerolactone, polyphosphazene, polyorthoester, cyclodextrin, and mixtures thereof. In some embodiments, the density enhancing agent is used in an appropriate amount to provide the desired density. In some embodiments, the density of the composition is 1.01 g/cm$^3$ or greater. In some embodiments, the density of the composition is about 1.01 g/cm$^3$ to about 1.08 g/cm$^3$.

In some embodiments, the composition further comprises a surfactant. In some embodiments, the surfactant is a non-ionic surfactant. In some embodiments, the surfactant can enhance the dispersion of the MTX in the aqueous phase. In some embodiments, the surfactant is selected from polyoxyethylene (20) sorbitan monolaurate (Tween 20), polyoxyethylene (20) sorbitan monopalmitate (Tween 40), polyoxyethylene (20) sorbitan monostearate (Tween 60), polyoxyethylene (20) sorbitan mono-oleate (Tween 80), polyoxyethylene (20) sorbitan tristearate (Tween 65), polyoxyethylene (20) sorbitan tri-oleate (Tween 85), sorbitan trioleate (Span 85), sorbitan monopalmitate (Span 40), sorbitan monostearate (Span 60), sorbitan mono-oleate (Span 80), and sorbitan tristearate (Span 65). In some embodiments, the surfactant is Tween 20 (polysorbate 20) or Tween 80 (polysorbate 80). In some embodiments, the surfactant is present at about 0.001 w/v to about 0.05% w/v.

In some embodiments, the composition includes a buffering agent. In some embodiments, the buffering agent is a pharmaceutically acceptable buffering agent, in particular for intravitreal administration. In some embodiments, the buffering agent is borate, phosphate, bicarbonate, carbonate, citrate, tetraborate, biphosphate, tromethamine, hydroxyethyl morpholine, or THAM (trishydroxymethylaminomethane).

In some embodiments, the composition has a pH of about 6 to 8. In some embodiments, the composition has a pH of about 6.5 to about 7.5. In some embodiments, the composition has a pH appropriate for intravitreal administration.

In another aspect, the present disclosure provides kits comprising the MTX compositions described herein. In some embodiments of the kits, the MTX composition is provided as multi-dose vial or single dose vial. In some embodiments, the MTX composition is in dry form, which is reconstituted with an appropriate solvent for preparing the composition for administration. In some embodiments, the MTX composition is provided in a sterile, single-dose syringe providing accuracy of dose and avoidance of site of administration compounding. It is well known that improper compounding practices can result in serious drug quality problems such as contamination, or excessive amounts of active ingredient, both of which can lead to patient injury and death (fda.gov/drugs/human-drug-compounding/compounding-and-fda-questions-and-answers). Sterile endophthalmitis is an infrequent complication of intravitreal injections but has been observed in the context of compounded drugs that have not been approved for intravitreal administration (Marticorena et al. 2012). From the studies administering compounded methotrexate, 5 patients were observed to have mild to severe inflammatory reactions that were described as sterile endophthalmitis (Frenkel et al. 2008, Habot-Wilner et al. 2021, Ma et al. 2016, Smith et al. 2002). In a prospective study evaluating methotrexate administered in post-operative eyes at risk for proliferative vitreoretinopathy (PVR) (Study ADX-2191-PVR-001, the GUARD Trial), no events of sterile or infectious endophthalmitis occurred.

In some embodiments, the amount of the composition administered intravitreally to a patient in need thereof is a small volume. In some embodiments, less than 0.5 mL is administered.

In some embodiments, a volume of 5 μL to 0.5 mL per dose of the composition is administered. In some embodiments, a volume of 15 μL to 0.3 mL per dose of the composition is administered. In some embodiments, a volume of 20 μL to 0.2 mL per dose of the composition is administered. In some embodiments, a volume of 25 μL to 0.1 mL per dose of the composition is administered.

In other embodiments, a volume of about 100 μL or less per dose of the composition is administered. In some embodiments, a volume of 25 μL to 75 μL per dose of the composition is administered. In some embodiments, a volume of 35 μL to 65 μL per dose of the composition is administered. In some embodiments, a volume of 45 μL to 55 μL per dose of the composition is administered.

In some embodiments, a volume of 50 μL±10 μL per dose of the composition is administered. In some embodiments, a volume of 50 μL±10 μL per dose of the composition is administered. In some embodiments, a volume of about 50 μL per dose of the composition is administered.

In some embodiments, the eye of the subject is administered the MTX composition described herein sufficient to deliver MTX at a dose of about 25 μg to about 600 μg. In some embodiments, the eye of the subject is administered a dose of MTX of about 30 µg to about 580 µg, about 35 µg to about 560 µg, about 40 µg to about 540 µg, about 45 µg to about 520 µg, about 50 µg to about 500 µg, about 60 µg to about 480 µg, about 70 µg to about 460 µg, about 80 µg to about 440 µg, about 90 µg to about 430 µg, about 100 µg to about 420 µg, about 120 µg to about 400 µg, about 140 µg to about 380 µg, about 160 µg to about 360 µg, about 180 µg to about 340 µg, or about 200 µg to about 320 µg. In some embodiments, the dose of MTX is about 200 µg to about 600 µg, or about 300 µg to about 500 µg.

In some embodiments, each dose of MTX is independently about 200 µg, about 300 µg, about 400 µg, or about 500 µg.

In one aspect, the present invention provides a method of treating proliferative vitreoretinopathy (PVR) comprising administering to a subject in need thereof intravitreally a composition comprising methotrexate at a concentration of about 5 mg/mL to about 12 mg/mL.

In some embodiments, the method comprises administering intravitreally a composition comprising methotrexate at a concentration of about 7 mg/mL to about 9 mg/mL; sucrose at a concentration of about 7% w/v to about 12% w/v; and a phosphate buffer.

In some embodiments, the composition is administered before, during, or after retinal detachment surgery.

In some embodiments, the composition is administered before, during, or after retinal detachment surgery, followed by administration about once a week. In some embodiments, the administration about once a week continues for 1, 2, 3, 4, 5, 6, 7, 8, 9, 10, 11, 12, 13, 14, 15, 16, 17, 18, 19, 20, 21, 22, 23, or 24 weeks. In some embodiments, the composition is administered before, during, or after retinal detachment surgery, followed by administration about once a week for about 6-12 weeks, or about 8 weeks.

In some embodiments, after the administration about once a week, the composition is then administered about once every other week for 1, 2, 3, 4, 5, 6, 7, 8, 9, 10, 11, 12, 13, 14, 15, 16, 17, 18, 19, 20, 21, 22, 23, or 24 weeks.

In some embodiments, the composition is administered before, during, or after retinal detachment surgery, followed by administration about once a week for about 8 weeks; further followed by administration about once every 2 weeks for about 8 weeks (about 4 administrations over about 8 weeks).

In some embodiments, the composition is administered before, during, or after retinal detachment surgery, followed by administration of the composition for up to 1 year, 10 months, 8 months, 6 months, 4 month, 3 months, 2 months, or 1 month.

In some embodiments, the composition is administered before, during, or after retinal detachment surgery, followed by administration of the composition for up to 6 months.

Surprisingly, it has now been found that treatment of certain ocular disorders with intravitreal methotrexate (MTX) results in fewer ocular side effects than standard of care.

In some embodiments, a central subfield thickness is less than 1.1 times the upper limit of normal and/or cystoid space(s) within 1 mm central subfield is measured after treatment.

In some embodiments, the central subfield thickness is measured from 4 to 14 weeks post-injection.

In some embodiments, the central subfield thickness is measured 12 weeks post-injection.

In some embodiments, the percent change in central subfield thickness from injection to measurement is at least 5%, at least 10%, or at least 15%.

In some embodiments, the upper limit of normal is 330 µm for Zeiss and Topcon SD OCT.

In some embodiments, the upper limit of normal is 352 µm for Heidelberg OCT.

In some embodiments, the cystoid space(s) are within 1 mm central subfield.

In some embodiments, the method results in an intraocular eye pressure elevation of less than or equal to 30 mm Hg.

In some embodiments, the method results in an intraocular eye pressure elevation of less than or equal to 24 mm Hg.

In some embodiments, the method results in an intraocular eye pressure elevation of less than or equal to 10 mm Hg.

In some embodiments, the method results in a greater than 20% reduction in macular thickness.

In some embodiments, the incidence of secondary punctate keratitis is reduced compared to the incidence of secondary punctate keratitis in subjects treated with comparative intravitreal ranibizumab injection or comparative dexamethasone treatment.

In some embodiments, the method provides an improved incidence of ocular side effects than treatment with ranibizumab or corticosteroids.

In some embodiments, the method provides an improved incidence of intraocular pressure (IOP) elevation (hypotony).

In some embodiments, the method provides a reduced incidence of retinal re-detachments due to PVR requiring re-operation within 6 months vs. routine surgical care.

In some embodiments, the method provides improved visual acuity vs. routine surgical care.

In some embodiments, the method provides an improvement in macular thickness, epiretinal membrane formation, and/or hypotony (elevated IOP) vs. routine surgical care.

In some embodiments, the method provides a reduced incidence of punctate keratitis. In some embodiments, the incidence is reduced by about 10-40%. In some embodiments, the incidence is reduced by 10%, 20%, 30%, 40%, or greater than 40%.

In some embodiments, the reduced incidence or improvement is statistically significant (p<0.05) across a group of patients.

Superficial punctate keratitis is an eye disorder caused by death of small groups of cells on the surface of the cornea (the clear layer in front of the iris and pupil). The eyes may become red, watery, and sensitive to light, and vision may decrease. In superficial punctate keratitis, the eyes are usually painful, watery, sensitive to bright light, and bloodshot, and vision may be slightly blurred. Often there is a burning, gritty feeling or a feeling as if a foreign object is trapped in the eye. Punctate keratitis is often an undesirable side effect of ocular injections or implants.

In some embodiments, the eye of the subject is administered the MTX composition described herein sufficient to deliver MTX at a dose of about 25 µg to about 600 µg. In some embodiments, the eye of the subject is administered a dose of MTX of about 30 µg to about 580 µg, about 35 µg to about 560 µg, about 40 µg to about 540 µg, about 45 µg to about 520 µg, about 50 µg to about 500 µg, about 60 µg to about 480 µg, about 70 µg to about 460 µg, about 80 µg to about 440 µg, about 90 µg to about 430 µg, about 100 µg to about 420 µg, about 120 µg to about 400 µg, about 140 µg to about 380 µg, about 160 µg to about 360 µg, about 180 µg to about 340 µg, or about 200 µg to about 320 µg. In some embodiments, the dose of MTX is about 200 µg to about 600 µg, or about 300 µg to about 500 µg.

In some embodiments, the composition further comprises sucrose at a concentration of about 7% w/v to about 12% w/v.

In some embodiments, the composition further comprises a phosphate buffer.

In some embodiments, the volume of composition administered is about 20 µL to about 300 µL. In particular embodiments, the composition administered is less than 100 µL, and is 45 µL to 65 µL, and most particularly the administration volume is 50 µL.

In some embodiments, the composition has a transit rate of less than 10 min in 1 mL of silicone oil (SiO) having a viscosity of at least 1000 centistoke and depth of 1 cm.

In some embodiments, the methotrexate is at a concentration of about 7 mg/mL to about 9 mg/mL; the sucrose is at a concentration of about 7% w/v to about 9% w/v; and the phosphate buffer is sodium phosphate dibasic. In some embodiments, the volume of composition administered is about 45 µL to about 60 µL. In particular embodiments, the compositions administered is 50 µL.

In some embodiments, the composition comprises methotrexate at a concentration of about 5 mg/mL to about 12 mg/mL, wherein the volume of composition administered is about 50 µl. In particular embodiments, the composition comprises methotrexate at a concentration of about 7 mg/mL to about 9 mg/mL, wherein the volume of composition administered is about 50 µl. In some embodiments, the composition comprises methotrexate at a concentration of about 8 mg/mL, wherein the volume of composition administered is about 50 µl.

In some embodiments, the composition comprises methotrexate at a concentration of about 8 mg/mL and sucrose at a concentration of about 7.5% w/v, wherein the volume of composition administered is about 50 µl.

In some embodiments, the composition comprises methotrexate at a concentration of about 8 mg/mL and sucrose at a concentration of about 7.5% w/v, wherein the volume of composition administered is about 50 µl and the pH is about 7.0 to about 9.0, more particularly about 7.1 to 8.1. In some embodiments, the osmolality of the composition is about 250-350 mOsm.

In some embodiments, the composition further comprises a sodium phosphate buffer at a concentration of about 0.113 mg/mL.

In some embodiments, the composition is stable upon storage at room temperature for at least one week. In some embodiments, the composition is stable upon storage at room temperature for up to one month. In some embodiments, the composition is stable upon storage at room temperature for up to two months. In some embodiments, the composition is stable upon storage at room temperature for up to three, four, five, or six months. In this context "stable" includes a lack of discoloration, precipitation, particulate matter, and/or impurities such that the composition can be used safely to treat an ocular disease described herein.

In some embodiments, the composition is light-stable, e.g., stable to exposure to indoor lighting and sunlight.

Presently, methotrexate compositions for intravitreal administration must be made at a compounding pharmacy, which may lead to contamination of the composition and unreliable purity, reproducibility, and safety. This need is addressed by the presently described compositions.

In some embodiments, the compositions are manufactured and packaged under GMP conditions. In some embodiments, the present methods utilize a sterile syringe pre-filled with a single dose of methotrexate composition. By using GMP procedures, the compositions, syringe, and packaging are sterile and deliver a reproducible and accurate dose.

The present invention further provides a kit comprising a disclosed composition in a pre-filled syringe. In some embodiments, the syringe contains a single dose volume of the composition, such as 50 µL±10 µL. In some embodiments, the syringe includes a needle appropriate for intravitreal injection.

In some embodiments, the compositions are delivered by intravitreal injection. In some embodiments, the compositions are high viscosity, and are delivered to the surface of the eye.

In some embodiments, the composition of MTX is used to treat, prevent, or reduce the risk of PVR, such as in a patient who has had retinal detachment surgery. In some embodiments, the present compositions provide sufficient rate of transit through silicone oil (SiO) used in retinal detachment surgery to deliver MTX in a therapeutically effective amount to prevent, reduce the risk of, or treat PVR.

In some embodiments, the composition of MTX is used to treat or prevent recurrent retinal detachment due to PVR. In some embodiments, the composition of MTX is used to treat or prevent recurrent retinal detachment in a patient who has undergone retinal detachment surgery. In some embodiments, the composition of MTX is used to treat retinal detachment associated with open-globe injury.

In some embodiments, the composition of MTX is used to treat intraocular lymphoma, such as primary vitreoretinal lymphoma (PVRL).

In some embodiments, the compositions of MTX are used to treat intraocular inflammation, such as uveitis; cystoid macular edema (CME) or diabetic macular edema; choroidal neovascularization; or prosthetic membranopathy.

In some embodiments, the composition of MTX is used to treat diseases that affect the retina, such as retinitis pigmentosa (RP).

In reference to the present disclosure and the detailed description that follow, the singular forms "a", "an" and "the" include plural referents unless the context clearly indicates otherwise. Thus, for example, reference to "a compound" refers to more than one compound.

Also, the use of "or" means "and/or" unless stated otherwise. Similarly, "comprise," "comprises," "comprising," "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

As used herein, the term "treating" or "treatment" of a disease, disorder, or syndrome, as used herein, includes (i) preventing the disease, disorder, or syndrome from occurring in a subject, i.e., causing the clinical symptoms of the disease, disorder, or syndrome not to develop in an animal that may be exposed to or predisposed to the disease, disorder, or syndrome but does not yet experience or display symptoms of the disease, disorder, or syndrome; (ii) inhibiting the disease, disorder, or syndrome, i.e., arresting its development; and (iii) relieving the disease, disorder, or syndrome, i.e., causing regression of the disease, disorder, or syndrome. As is known in the art, adjustments for systemic versus localized delivery, age, body weight, general health, sex, diet, time of administration, drug interaction and the severity of the condition may be necessary, and is ascertainable by one of ordinary skill in the art.

As used herein, the term "prophylactic treatment" refers to a treatment administered to a subject who does not display signs or symptoms of a disease, pathology, or medical disorder, or displays only early signs or symptoms of a disease, pathology, or disorder, for the purpose of diminishing, preventing, or decreasing the risk of developing the disease, pathology, or medical disorder. A prophylactic treatment functions as a preventative treatment against a disease or disorder.

As used herein, the term "therapeutically effective amount" means any amount which, as compared to a corresponding subject who has not received such amount, results in improved treatment, healing, prevention, or amelioration of a disease or disorder, or a decrease in the rate of advancement of a disease or disorder, and also includes amounts effective to enhance normal physiological function.

As used herein, the term "pharmaceutically acceptable" refers to those compounds, biologic agents, materials, compositions and/or dosage forms, which are, within the scope of sound medical judgment, suitable for administration to a subject, e.g., a mammal or human, without excessive toxicity, irritation allergic response and other problem complications commensurate with a reasonable benefit/risk ratio.

In one aspect, the present disclosure provides a composition comprising MTX, or a pharmaceutically acceptable salt thereof, and a density enhancing agent. In some embodiments, the density enhancing agent is present in an amount effective to provide a transit rate of less than 10 min in 1 ml of silicone oil (SiO). As used herein, a "transit rate" refers to the time in which the MTX composition when applied to SiO layer separated from a non-miscible aqueous layer, preferably phosphate buffered saline (PBS), reaches the interface of the SiO and aqueous layer. In some embodiments, where the composition has a higher density than the density of the SiO, the transit rate can be referred to as the "sink rate." In some embodiments, the transit or sink rate of the composition is less than 10 min, less than 8 min, less than 7 min, less than 6 min, or less than 5 min in 1 ml of SiO having a depth of 1 cm. In some embodiments, the transit rate or sink rate of the composition is measured in SiO used as a tamponade for treating retinal detachment.

In some embodiments, the SiO has a lower density than water. In these SiOs, the SiO layer floats on top of an aqueous layer, and the MTX composition sinks in the SiO to the interface of the SiO and aqueous layer.

In some embodiments, the transit rate or sink rate is in SiO having a viscosity of at least 1000 centistoke. In some embodiments, the SiO has a viscosity of about 1000 centistoke. In some embodiments, the SiO having a viscosity of 1000 centistoke is polydimethyl siloxane 1000 centistoke oil.

In some embodiments, the transit rate or sink rate is in SiO having a viscosity of about 5000 centistoke. In some embodiments, the SiO having a viscosity of 5000 centistoke is polydimethyl siloxane 5000 centistoke oil.

In some embodiments, the density of the MTX composition is higher than the density of the SiO to provide an appropriate transit rate or sink rate. In some embodiments, the density of the composition is at least about 1.01 $g/cm^3$, at least about 1.02 $g/cm^3$, at least about 1.03 $g/cm^3$, at least about 1.04 $g/cm^3$, at least about 1.05 $g/cm^3$, at least about 1.06 $g/cm^3$, at least about 1.07 $g/cm^3$, at least about 1.08 $g/cm^3$, at least about 1.09 $g/cm^3$, at least about 1.10 $g/cm^3$, at least about 1.11 $g/cm^3$, at least about 1.12 $g/cm^3$, at least about 1.13 $g/cm^3$, at least about 1.14 $g/cm^3$, at least about 1.15 $g/cm^3$, at least about 1.20 $g/cm^3$, or at least about 1.25 $g/cm^3$ at 20° C.

In some embodiments, the density of the MTX composition is about 1.01 to about 1.2 $g/cm^3$, about 1.02 $g/cm^3$ to about 1.2 $g/cm^3$, about 1.03 $g/cm^3$ to about 1.2 $g/cm^3$, about 1.04 $g/cm^3$ to about 1.2 $g/cm^3$, about 1.05 $g/cm^3$ to about 1.2 $g/cm^3$, about 1.06 $g/cm^3$ to about 1.2 $g/cm^3$, about 1.07 $g/cm^3$ to about 1.2 $g/cm^3$, about 1.08 $g/cm^3$ to about 1.2 $g/cm^3$, about 1.09 $g/cm^3$ to about 1.2 $g/cm^3$, about 1.10 $g/cm^3$ to about 1.2 $g/cm^3$, about 1.11 $g/cm^3$ to about 1.2 $g/cm^3$, about 1.12 $g/cm^3$ to about 1.2 $g/cm^3$, about 1.13 $g/cm^3$ to about 1.2 $g/cm^3$, about 1.14 $g/cm^3$ to about 1.2 $g/cm^3$, about 1.15 $g/cm^3$ to about 1.2 $g/cm^3$, about 1.16 $g/cm^3$ to about 1.2 $g/cm^3$, about 1.17 $g/cm^3$ to about 1.2 $g/cm^3$, about 1.18 $g/cm^3$ to about 1.2 $g/cm^3$, or about 1.19 $g/cm^3$ to about 1.2 $g/cm^3$ at 20° C. In some embodiments, the composition has a density of about 1.01 $g/cm^3$ to about 1.08 $g/cm^3$ at 20° C.

In some embodiments, the density of the composition is about 1.01 to about 1.25 $g/cm^3$ at 20° C. In some embodiments, the density of the composition is about 1.02 to about 1.2 $g/cm^3$ at 20° C. In some embodiments, the density of the composition is about 1.03 to about 1.15 $g/cm^3$ at 20° C. In some embodiments, the density of the composition is about 1.04 to about 1.1 $g/cm^3$ at 20° C.

In some embodiments, the density of the composition is about 1.01 g/mL, about 1.02 $g/cm^3$, about 1.03 $g/cm^3$, about 1.04 $g/cm^3$, about 1.05 $g/cm^3$, about 1.06 $g/cm^3$, about 1.07 $g/cm^3$, about 1.08 $g/cm^3$, about 1.09 $g/cm^3$, about 1.10 $g/cm^3$, about 1.11 $g/cm^3$, about 1.12 $g/cm^3$, about 1.13 $g/cm^3$, about 1.14 $g/cm^3$, about 1.15 $g/cm^3$, about 1.16 $g/cm^3$, about 1.17 $g/cm^3$, about 1.18 $g/cm^3$, about 1.19 g/mL, about 1.2 $g/cm^3$, about 1.21 $g/cm^3$, about 1.22 $g/cm^3$, about 1.23 $g/cm^3$, about 1.24 $g/cm^3$, or about 1.25 $g/cm^3$ at 20° C.

In some embodiments, the SiO is heavy silicone oil (HSO), which refers to SiO that has a higher density than the density of water. In such embodiments, the aqueous layer floats on top of the HSO layer. In some embodiments, the MTX composition is formulated to have a lower density than the density of HSO, thus allowing the MTX composition to float from the SiO to the interface of the SiO and aqueous layer. In some embodiments, the transit rate of the MTX composition is less than 10 min in 1 ml of HSO at a depth of 1 cm. In some embodiments, the transit rate of the MTX composition is less than 8 min, less than 7 min, less than 6 min, or less than 5 min in 1 ml of HSO having a depth of 1 cm. In some embodiments, the MTX composition is applied to the bottom of the SiO layer 1 cm away from the interface of the HSO and the aqueous layer to assess the transit rate.

In some embodiments, the HSO is Oxane HD (mixture of 5700-centistoke SiO and RMN-3, a partially fluorinated olefin; density of 1.02 $g/cm^3$ and a viscosity of 3,300-3,500 mPas at 25° C.), Densiron 68 (mixture of perfluorohexyloctane (F6H8) and 5,000-centistoke silicone oil; density 1.06 $g/cm^3$; viscosity 1400 mPas at 25° C.), or HSV-45 3000. In some embodiments, the HSO is perfluorocarbon liquids (PFCLs) or semifluorinated alkanes, such as perfluorohexyloctane (F6H8; density of 1.331 $g/cm^3$). PFCLs include perfluoro-n-octane (C8F18; density of 1.759 $g/cm^3$) and perfluorodecalin (C10F18). The specific gravity of these SiOs can range from 1.7 g/mL to more than 2.0 g/mL.

In some embodiments where HSO is used, the density of the MTX composition is lower than the density of the HSO. In some embodiments, the density of the composition is less than about 2.0 g/cm³, less than about 1.8 g/cm³, less than about 1.6 g/cm³, less than about 1.5 g/cm³, less than about 1.4 g/cm³, less than about 1.3 g/cm³, less than about 1.2 g/cm³, less than about 1.19 g/cm³, less than about 1.18 g/cm³, less than about 1.17 g/cm³, less than about 1.16 g/cm³, less than about 1.15 g/cm³, less than about 1.14 g/cm³, less than about 1.13 g/cm³, less than about 1.12 g/cm³, less than about 1.11 g/cm³, less than about 1.10 g/cm³, less than about 1.09 g/cm³, less than about 1.08 g/cm³, less than about 1.07 g/cm³, less than about 1.06 g/cm³, less than about 1.05 g/cm³, less than about 1.04 g/cm³, less than about 1.03 g/cm³, or less than about 1.02 g/cm³.

In some embodiments, the density of the composition is about 2.0 g/cm³ to about 1.01 g/cm³, about 1.8 g/cm³ to about 1.01 g/cm³, about 1.6 g/cm³ to about 1.01 g/cm³, about 1.5 g/cm³, to about 1.01 g/cm³, about 1.4 g/cm³ to about 1.01 g/cm³, about 1.3 g/cm³ to about 1.01 g/cm³, about 1.2 g/cm³ to about 1.01 g/cm³, about 1.19 g/cm³ to about 1.01 g/cm³, about 1.18 g/cm³ to about 1.01 g/cm³, about 1.17 g/cm³ to about 1.01 g/cm³, about 1.16 g/cm³ to about 1.01 g/cm³, about 1.15 g/cm³, to about 1.01 g/cm³, about 1.14 g/cm³ to about 1.01 g/cm³, about 1.13 g/cm³ to about 1.01 g/cm³, about 1.12 g/cm³ to about 1.01 g/cm³, about 1.11 g/cm³ to about 1.01 g/cm³, about 1.10 g/cm³ to about 1.01 g/cm³, about 1.09 g/cm³ to about 1.01 g/cm³, about 1.08 g/cm³ to about 1.01 g/cm³, about 1.07 g/cm³ to about 1.01 g/cm³, about 1.06 g/cm³ to about 1.01 g/cm³, about 1.05 g/cm³ to about 1.01 g/cm³, about 1.04 g/cm³ to about 1.01 g/cm³, or about 1.03 g/cm³ to about 1.01 g/cm³.

In some embodiments, where a combination of an oil having a density lower than water and an oil having a density higher than water are used as a tamponade, the MTX composition has a density greater than the oil having lower density than water and a density lower than the oil having a higher density than water. The MTX composition having the appropriate density can be selected based on the guidance provide herein. In some embodiments, compositions having the appropriate density in the applicable ranges described above can be used.

In certain embodiments, the composition comprises a density enhancing agent to provide an appropriate density to impart a desired transit rate or sink rate. In some embodiments, the density enhancing agent is sucrose, trehalose, glucose, carbopol, polyvinyl acetate, polyvinyl alcohol (PVA), polyvinylpyrrolidone (PVP), carboxymethylcellulose, hydroxypropyl methylcellulose, hydroxypropyl cellulose, hydroxylethyl cellulose, polyethylene glycol (PEG), glycerol, poly(lactide) (PLA), poly(lactide-co-glycolide) (PLGA), polyglycolide (PGA), polyhydroxybutyric acid, polycaprolactone, polyvalerolactone, polyphosphazene, polyorthoester, cyclodextrin, or mixtures thereof. In some embodiments, a preferred density enhancing agent is sucrose or PEG 4000.

In some embodiments, the density enhancing agent comprises sucrose. In some embodiments, the composition comprises sucrose at a concentration of about 0.5% w/v to about 20% w/v; about 1% w/v to about 20% w/v, 2% w/v to about 20% w/v, about 3% w/v to about 20% w/v, about 4% w/v to about 20% w/v, about 5% w/v to about 20% w/v, about 6% w/v to about 20% w/v, about 7% w/v to about 20% w/v, about 8% w/v to about 20% w/v, about 9% w/v to about 20% w/v, about 10% w/v to about 20% w/v, about 11% w/v to about 20% w/v, about 12% w/v to about 20% w/v, about 13% w/v to about 20% w/v, about 14% w/v to about 20%, about 15% w/v to about 20%, or about 16% w/v to about 20%.

In some embodiments, the composition comprises sucrose at a concentration of about 0.5% w/v to about 18% w/v, about 1% w/v to about 17%, w/v 2% w/v to about 16% w/v, about 3% w/v to about 15% w/v, about 4% w/v to about 14% w/v, about 5% w/v to about 1% w/v, about 6% w/v to about 13% w/v, about 7% to about 12% w/v, or about 8% to about 11% w/v. In some embodiments, the composition comprises sucrose at a concentration of about 7% w/v to about 9% w/v, preferably about 7.7% w/v.

In some embodiments, the composition comprises sucrose at a concentration of about 0.5% w/v, about 0.6% w/v, about 0.7% w/v, about 0.8% w/v, about 0.9% w/v, about 1% w/v, about 2% w/v, about 3% w/v, about 4% w/v, about 5% w/v, about 6% w/v, about 7% w/v, about 8% w/v, about 9% w/v, about 10% w/v, about 11% w/v, about 12% w/v, about 13% w/v, about 14% w/v, about 15% w/v, about 16% w/v, about 17% w/v, about 18% w/v, about 19% w/v, or about 20% w/v. In some embodiments, the composition has sucrose at a concentration of about 7.5% w/v, 8.5% w/v, or about 9.5% w/v.

In some embodiments, the density enhancing agent comprises polyethylene glycol (PEG). In some embodiments, the PEG is PEG 400 to PEG 20000. In some embodiments, the PEG is PEG 400, PEG 500, PEG 600, PEG 700, PEG 800, PEG 900, PEG 1000, PEG 1100, PEG 1200, PEG 1300, PEG 1400, PEG 1450, PEG 1500, PEG 1600, PEG 1700, PEG 1800, PEG 1900, PEG 2000, PEG 2100, PEG 2200, PEG 2300, PEG 2400, PEG 2500, PEG 2600, PEG 2700, PEG 2800, PEG 2900, PEG 3000, PEG 3250, PEG 3350, PEG 3500, PEG 3750, PEG 4000, PEG 4250, PEG 4500, PEG 4750, PEG 5000, PEG 5500, PEG 6000, PEG 6500, PEG 7000, PEG 7500, PEG 8000, or mixtures thereof. In some embodiments, the PEG is PEG 9000, PEG 10000, PEG 11000, PEG 12000, PEG 13000, PEG 14000, PEG 15000, PEG 16000, PEG 17000, PEG 18000, PEG 19000, PEG 20000, or mixtures thereof. In a preferred embodiment, the PEG is PEG 4000.

In some embodiments, the composition comprises PEG at a concentration to provide sufficient density for the composition to have the transit rate or sink rate described herein. The densities of PEG solutions of different molecular weights are available in the art (see, e.g., Gonzalez-Tello et al., J Chem Eng Data, 1994; 39:611-614; Regupahti et al., J. Chem. Eng. Data, 2009; 54(3):1100-1106; publications incorporated herein by reference). For example, PEG 4000 at 50% w/v in water has a density of about 1.13 g/cm³ at 20° C.

In some embodiments, the composition comprises PEG 4000 at a concentration of about 1% w/v to about 60% w/v, about 1% w/v to about 60% w/v, about 2% w/v to about 60% w/v, about 3% w/v to about 60% w/v, about 4% w/v to about 60% w/v, about 5% w/v to about 60% w/v, about 6% w/v to about 60% w/v, about 7% w/v to about 60% w/v, about 8% w/v to about 60% w/v, about 9% w/v to about 60% w/v, about 10% w/v to about 60% w/v, about 15% w/v to about 60% w/v, about 20% w/v to about 60% w/v, about 25% w/v to about 60% w/v, about 30% w/v to about 60% w/v, about 35% w/v to about 60% w/v, about 40% w/v to about 60% w/v, about 45% w/v to about 60%, about 50% w/v to about 60% w/v, or about 55% w/v to about 60% w/v.

In some embodiments, the composition comprises PEG 4000 at a concentration of about 1% w/v to about 60% w/v, about 1% w/v to about 55% w/v, about 2% w/v to about 50% w/v, about 3% w/v to about 45% w/v, about 4% w/v to about 40% w/v, about 5% w/v to about 35% w/v, about 6% w/v to about 30% w/v, about 7% w/v to about 28% w/v, about 8% w/v to about 26% w/v, about 9% w/v to about 24% w/v, about 10% w/v to about 22% w/v, or about 15% w/v to about 20% w/v. In some embodiments, the composition comprises PEG 4000 at a concentration of about 1% w/v to about 15% w/v, 12% w/v to about 14% w/v, 3% w/v to about 13% w/v, 4% w/v to about 12% w/v, 5% w/v to about 11% w/v, 6% w/v to about 10% w/v, or 7% w/v to about 9% w/v.

In some embodiments, the composition comprises PEG 4000 at a concentration of about 1% w/v, about 2% w/v, about 3% w/v, about 4% w/v, about 5% w/v, about 6% w/v, about 7% w/v, about 8% w/v, about 9% w/v, about 10% w/v, about 11% w/v, about 12% w/v, about 13% w/v, about 14% w/v, about 15% w/v, about 16% w/v, about 17% w/v, about 18% w/v, about 19% w/v, about 20% w/v, about 25% w/v, about 30% w/v, about 35% w/v, about 40% w/v, about 45% w/v, about 50% w/v, about 55% w/v, or about 60% w/v.

It is to be understood that while the description for the MTX composition herein uses sucrose or PEG 4000 as exemplary density enhancing agents, the appropriate concentration of other density enhancing agents to achieve the desired transit rate or sink rate and/or the desired density can be used in view of the knowledge in the art of the densities for the various density enhancing agents described herein.

In some embodiments, the MTX composition further comprises one or more surfactants. In some embodiments, the surfactant is a non-ionic surfactant. In some embodiments, the surfactant is suitable for intravitreal administration. In some embodiments, the surfactant is polyoxyethylene (20) sorbitan monolaurate (Tween 20), polyoxyethylene (20) sorbitan monopalmitate (Tween 40), polyoxyethylene (20) sorbitan monostearate (Tween 60), polyoxyethylene (20) sorbitan mono-oleate (Tween 80), polyoxyethylene (20) sorbitan tristearate (Tween 65), polyoxyethylene (20) sorbitan tri-oleate (Tween 85), sorbitan trioleate (Span 85), sorbitan monopalmitate (Span 40), sorbitan monostearate (Span 60), sorbitan mono-oleate (Span 80), sorbitan tristearate (Span 65), or combinations thereof. In some embodiments, the surfactant is Tween 20 (polysorbate 20) or Tween 80 (polysorbate 80).

In some embodiments, the composition comprises a surfactant at about 0.001% w/v to about 0.5% w/v, about 0.002% w/v to about 0.5% w/v, about 0.004% w/v to about 0.5% w/v, about 0.006% w/v to about 0.5% w/v, about 0.008% w/v to about 0.5% w/v, about 0.010% w/v to about 0.5% w/v, about 0.012% w/v to about 0.5% w/v, about 0.014% w/v to about 0.5% w/v, about 0.016% w/v to about 0.5% w/v, about 0.018% w/v to about 0.5% w/v, about 0.02% w/v to about 0.5% w/v, about 0.03% w/v to about 0.5% w/v, about 0.04% w/v to about 0.5% w/v, about 0.05% w/v to about 0.5% w/v, about 0.06% w/v to about 0.5% w/v, about 0.07% w/v to about 0.5% w/v, about 0.08% w/v to about 0.5% w/v, about 0.1% w/v to about 0.5% w/v, about 0.12% w/v to about 0.5% w/v, about 0.14% w/v to about 0.5% w/v, about 0.16% w/v to about 0.5% w/v, about 0.18% w/v to about 0.50% w/v, about 0.2% w/v to about 0.50% w/v, about 0.30% w/v to about 0.50% w/v, or about 0.4% w/v to about 0.5% w/v. In some embodiments, the surfactant is present at 0.0015% w/v to about 0.05% w/v. In some embodiments, the surfactant is present at 0.01% w/v to 0.05% w/v. In some embodiments, the surfactant is present at 0.015% w/v to about 0.03% w/v.

In some embodiments, the composition has surfactant at about 0.001% w/v, about 0.002% w/v, about 0.004% w/v, about 0.006% w/v, about 0.008% w/v, about 0.010% w/v, about 0.012% w/v, about 0.014% w/v, about 0.016% w/v, about 0.018% w/v, about 0.02% w/v, about 0.03% w/v, about 0.04% w/v, about 0.05% w/v, about 0.06% w/v, about 0.07% w/v, about 0.08% w/v, about 0.10% w/v, about 0.12% w/v, about 0.14% w/v, about 0.16% w/v, about 0.18% w/v, about 0.2% w/v, about 0.22% w/v, about 0.24% w/v, about 0.26% w/v, about 0.28% w/v, about 0.3% w/v, about 0.32% w/v, about 0.34% w/v, about 0.36% w/v, about 0.38% w/v, about 0.4% w/v, about 0.42% w/v, about 0.44% w/v, about 0.46% w/v, about 0.48% w/v, or about 0.5% w/v.

In some embodiments, the composition includes a preservative, particularly a pharmaceutically acceptable preservative for intravitreal injection. In some embodiments, the preservative is benzyl alcohol. In some embodiments, the composition is free of preservatives.

In some embodiments, the composition further comprises a buffering agent. In some embodiments, the buffering agent is a pharmaceutically acceptable buffering agent, in particular a buffering agent suitable for intravitreal administration. In some embodiments, the buffering agent is borate, phosphate, bicarbonate, carbonate, citrate, tetraborate, biphosphate, tromethamine, hydroxyethyl morpholine, or THAM (trishydroxymethylamino-methane). In some embodiments, the buffering agent is phosphate.

In some embodiments, the buffering agent is present in a sufficient amount to provide buffering capacity to the composition. In some embodiments, the buffering agent is present at a concentration of about 0.005 mM to about 5 mM, about 0.01 mM to about 4 mM, about 0.02 mM to about 3 mM, about 0.03 mM to about 2 mM, about 0.04 mM to about 1.5 mM, about 0.05 mM to about 1 mM, or about 0.1 mM to about 0.8 mM.

In some embodiments, the buffering agent is present at a concentration of about 0.005 mM, 0.01 mM, 0.02 mM, 0.03 mM, 0.04 mM, 0.05 mM, 0.1 mM, 0.2 mM, 0.3 mM, 0.4 mM, 0.5 mM, 0.6 mM, 0.7 mM, 0.8 mM, 0.9 mM, 1 mM, 2 mM, 3 mM, 4 mM, 5 mM or more as needed.

In some embodiments, the pH of the composition is about 5.5 to about 8.5. In some embodiments, the pH is about 6 to about 8, or about 6.5 to about 7.5. In some embodiments, the composition has a pH of about 5.5, about 6.0, about 6.5, about 7, about 7.5 or about 8. Preferably, the pH of the composition is approximate pH of the vitreous in the eye.

In some embodiments, the MTX is present in the composition at a concentration that when administered is sufficient to prevent or reduce the risk of or treat a disease, disorder, or conditions disclosed herein. In some embodiments, the MTX is present in the composition at a concentration sufficient to prevent or reduce the risk of or treat PVR. In some embodiments, the MTX is present in the composition at a concentration sufficient to prevent or reduce the risk of or treat intraocular lymphoma. In some embodiments, the MTX is present in the composition at a concentration sufficient to prevent or reduce the risk of or treat intraocular inflammation. Methotrexate is also known by its chemical names N-[4-[[(2,4-diamino-6-pteridinyl)methyl]methylamino]benzoyl]-L-glutamic acid and 4-amino-10-methylfolic acid. In some embodiments, the MTX in composition is present in an amount such that intravitreal administration provides a therapeutically effective dose, including a prophylactically effective dose.

In some embodiments, the MTX, or a pharmaceutically acceptable salt thereof, is present at about 2 mg/mL to about 20 mg/mL. In some embodiments, the MTX, or a pharmaceutically acceptable salt thereof, is present at about 3 mg/mL to about 20 mg/mL, about 4 mg/mL to about 20 mg/mL, about 5 mg/mL to about 20 mg/mL, about 6 mg/mL to about 20 mg/mL, about 7 mg/mL to about 20 mg/mL, about 8 mg/mL to about 20 mg/mL, about 9 mg/mL to about 20 mg/mL, about 10 mg/mL to about 20 mg/mL, about 11 mg/mL to about 20 mg/mL, about 12 mg/mL to about 20 mg/mL, about 13 mg/mL to about 20 mg/mL, about 14 mg/mL to about 20 mg/mL, about 15 mg/mL to about 20 mg/mL, about 16 mg/mL to about 20 mg/mL, or about 18 mg/mL to about 20 mg/mL.

In some embodiments, the MTX, or a pharmaceutically acceptable salt thereof, is present at about 2 mg/mL to about 19 mg/mL, about 3 mg/mL to about 18 mg/mL, about 4 mg/mL to about 18 mg/mL, about 5 mg/mL to about 17 mg/mL, about 6 mg/mL to about 16 mg/mL, about 7 mg/mL to about 15 mg/mL, about 8 mg/mL to about 14 mg/mL, about 9 mg/mL to about 13 mg/mL, about 10 mg/mL to about 12 mg/mL. In some embodiments, the MTX, or a pharmaceutically acceptable salt thereof, is present at about 5 mg/ml to about 12 mg/mL, 6 mg/mL to about 11 mg/mL, or about 7 mg/mL to about 10 mg/mL.

In some embodiments, the MTX, or a pharmaceutically acceptable salt thereof, is present at about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 18 mg/mL, or about 20 mg/mL. Preferably, the MTX is present at about 8 mg/mL.

In some embodiments, the MTX is present in the composition as a pharmaceutically acceptable salt or as esters of MTX. Pharmaceutically acceptable salts can be selected from, but are not limited to, alkali metal salts such as sodium or potassium, alkaline earth salts or an ammonium salt (all of which are herein referred to as a pharmaceutically acceptable salts). In some embodiments, methotrexate refers to methotrexate disodium. Methotrexate also includes acetylated forms, benzhydryl-sulfinylacetic acid forms, sulfone forms, hydroxylated forms, polymorphic forms, analogs, derivatives, cogeners, prodrugs, metabolic acids and compounds made by mixtures thereof. In some embodiments, the methotrexate also includes individual enantiomers or racemic mixtures of methotrexate.

In some embodiments, the composition has an osmolarity that is compatible with its use in treating a disease, disorder, or condition disclosed herein. In some embodiments, the osmolarity of the composition is compatible with intravitreal use. In some embodiments, the composition has an osmolarity of about 200 to about 1000 mOsm/L or about 200 to about 500 mOsm/L, or any specific value within said ranges, for example, 200 mOsm/L, 210 mOsm/L, 220 mOsm/L, 230 mOsm/L, 240 mOsm/L, 250 mOsm/L, 260 mOsm/L, 270 mOsm/L, 280 mOsm/L, 290 mOsm/L, 300 mOsm/L, 310 mOsm/L, 320 mOsm/L, 330 mOsm/L, 340 mOsm/L, 350 mOsm/L, 360 mOsm/L, 370 mOsm/L, 380 mOsm/L, 390 mOsm/L, or 400 mOsm/L. In a particular embodiment, the ophthalmic formulations are adjusted with a tonicity agent to an osmolarity in the range of about 250 to about 450 mOsm/L, or about 300 to about 400 mOsm/L.

Preferably, the osmolarity of the composition is about 350±50 mOsm/L.

In some embodiments, the compositions can have one or more tonicity agents, which can be used to adjust the tonicity of the composition, for example, to the tonicity appropriate for intravitreal use. Suitable tonicity agents include, by way of example and not limitation, dextrans (e.g., dextran 40 or 70), dextrose, glycerin, potassium chloride, propylene glycol, and sodium chloride. Equivalent amounts of one or more salts made up of cations, such as potassium, ammonium; and anions such as chloride, citrate, ascorbate, borate, phosphate, bicarbonate, sulfate, thiosulfate, bisulfate; the salts sodium bisulfate and ammonium sulfate, can also be used. The amount of tonicity agent can vary, depending on the particular agent to be added.

In some embodiments, the MTX composition comprises the following:
Methotrexate: 2 mg/mL to about 20 mg/mL; and
Sucrose: 0.5% w/v to about 20% w/v.

In some embodiments, the MTX composition comprises the following:
Methotrexate: 5 mg/mL to about 15 mg/mL; and
Sucrose: 4% w/v to about 15% w/v.

In some embodiments, the MTX composition comprises the following:
Methotrexate: 2 mg/mL to about 20 mg/mL; and
PEG 4000: 1% w/v to about 60% w/v.

In some embodiments, the MTX composition comprises the following:
Methotrexate: 5 mg/mL to about 15 mg/mL; and
PEG 4000: 4% w/v to about 15% w/v.

In some embodiments, each of the above compositions further includes a surfactant. In some embodiments, any of the surfactants disclosed herein can be used. In some embodiments, the surfactant is polyoxyethylene (20) sorbitan monolaurate (Tween 20), polyoxyethylene (20) sorbitan monopalmitate (Tween 40), polyoxyethylene (20) sorbitan monostearate (Tween 60), polyoxyethylene (20) sorbitan mono-oleate (Tween 80), polyoxyethylene (20) sorbitan tristearate (Tween 65), polyoxyethylene (20) sorbitan trioleate (Tween 85), and sorbitan trioleate (Span 85). sorbitan monopalmitate (Span 40), sorbitan monostearate (Span 60), sorbitan mono-oleate (Span 80), or sorbitan tristearate (Span 65). In some embodiments, the surfactant is Tween 20 or Tween 80.

In some embodiments, the MTX composition comprises the following:
Methotrexate: 2 mg/mL to about 20 mg/mL;
Sucrose: 0.5% w/v to about 20% w/v; and
Surfactant: 0.001% to about 0.5% w/v.

In some embodiments, the MTX composition comprises the following:
Methotrexate: 5 mg/mL to about 15 mg/mL;
Sucrose: 4% w/v to about 15% w/v;
Surfactant: 0.01% to about 0.05% w/v.

In some embodiments, the MTX composition comprises the following:
Methotrexate: 2 mg/mL to about 20 mg/mL; and
PEG 4000: 1% w/v to about 60% w/v; and
Surfactant: 0.001% to about 0.5% w/v.

In some embodiments, the MTX composition comprises the following:
Methotrexate: 5 mg/mL to about 15 mg/mL;
PEG 4000: 4% w/v to about 15% w/v; and
Surfactant: 0.01% to about 0.05% w/v.

In some embodiments, the surfactant in the above embodiments is Tween 20, also referred to as polysorbate 20. In some embodiment, the surfactant in the above embodiments is Tween 80, also referred to as polysorbate 80.

In some embodiments, the MTX composition has the following formulation (F1):

| Component | Concentration |
|---|---|
| Methotrexate | 8 mg/mL |
| Sucrose | 8% w/v |
| Sodium phosphate dibasic dihydrate | 0.142% w/v |
| 1M NaOH/HCl | pH adjusted to 7.4 ± 0.2 |

| Component | Concentration |
| --- | --- |
| Final volume | 1 mL |

In some embodiments, the MTX composition has the following formulation (F2):

| Component | Concentration |
| --- | --- |
| Methotrexate | 8 mg/mL |
| Polyethylene Glycol 4000 | 7.5% w/v |
| Sodium phosphate dibasic dihydrate | 0.142% w/v |
| 1M NaOH/HCl | pH adjusted to 7.4 ± 0.2 |
| Final volume | 1 mL |

In some embodiments, the MTX composition has the following formulation (F3):

| Component | Concentration |
| --- | --- |
| Methotrexate | 8 mg/mL |
| NaCl | 0.9% w/v |
| Final volume | 1 mL |

In some embodiments, the MTX composition has the following formulation (F4):

| Component | Concentration |
| --- | --- |
| Methotrexate | 8 mg/mL |
| Sucrose | 8% w/v |
| Tween 20 | 0.015% w/v |
| Sodium phosphate dibasic dihydrate | 0.142% w/v |
| 1M NaOH/HCl | pH adjusted to 7.4 ± 0.2 |
| Final volume | 1 mL |

In some embodiments, the MTX composition has the following formulation (F5):

| Component | Concentration |
| --- | --- |
| Methotrexate | 8 mg/mL |
| Sucrose | 8% w/v |
| Tween 20 | 0.03% w/v |
| Sodium phosphate dibasic dihydrate | 0.142% w/v |
| 1M NaOH/HCl | pH adjusted to 7.4 ± 0.2 |
| Final volume | 1 mL |

In some embodiments, the MTX composition has the following formulation (F6):

| Component | Concentration |
| --- | --- |
| Methotrexate | 8 mg/mL |
| Sucrose | 8% w/v |
| Tween 80 | 0.015% w/v |
| Sodium phosphate dibasic dihydrate | 0.142% w/v |
| 1M NaOH/HCl | pH adjusted to 7.4 ± 0.2 |
| Final volume | 1 mL |

In some embodiments, the MTX composition has the following formulation (F7):

| Component | Concentration |
| --- | --- |
| Methotrexate | 8 mg/mL |
| Sucrose | 7.5% w/v |
| Sodium phosphate dibasic dihydrate | 0.142% w/v |
| 1M NaOH/HCl | pH adjusted to 7.4 ± 0.2 |
| Final volume | 1 mL |

In some embodiments, the MTX composition has the following formulation (F8):

| Component | Concentration |
| --- | --- |
| Methotrexate | 8 mg/mL |
| Sucrose | 75 mg/mL |
| Sodium phosphate dibasic dihydrate | 0.113 mg/mL |
| 1M NaOH/HCl | As needed |
| Final volume | As needed to QS |

It is to be understood that variations in the above specific embodiments can be prepared according to the guidance provided herein.

1.2. Uses and Methods

In another aspect, the present disclosure provides use of the MTX compositions for preventing or reducing the risk of or treating PVR, intraocular lymphoma, or intraocular inflammation.

In some embodiments, the present disclosure provides use of the MTX compositions for preventing or reducing the risk of PVR or treating PVR. In some embodiments, a method of preventing or reducing the risk of or treating PVR comprises administering to a subject in need thereof a therapeutically effective amount of an MTX composition described herein. In some embodiments, the MTX composition is administered intravitreally.

In some embodiments, the present disclosure provides use of MTX in the preparation of a medicament for treating PVR, intraocular lymphoma, or intraocular inflammation, wherein the medicament comprises any of the compositions described above. In some embodiments, the medicament comprises MTX and a density enhancing agent, as described herein. In some embodiments, the medicament comprises MTX, a density enhancing agent, and a surfactant, as described herein.

In some embodiments, the subject for treatment with the MTX composition has a retinal injury, such as a tear or hole in the retina but which has not resulted in retinal detachment. In some embodiments, the subject for treatment with the MTX composition has undergone laser surgery (e.g., photocoagulation) for treatment for the retinal tear or hole. In some embodiments, the subject for treatment with the MTX composition has undergone cryopexy for treatment of the retinal tear or hole. In some embodiments, the subject for treatment with the MTX composition has undergone treatment for a retinal tear or hole and has one or more risk factors for PVR, as discussed further below. In some embodiments, the method comprises administering to an eye of a subject who has undergone laser surgery (e.g., laser retinopexy) or cryopexy for treatment of a retinal tear or hole a therapeutically effective amount of an MTX composition of the present disclosure.

In some embodiments, the subject for treatment with the MTX composition has suffered a retinal injury which is a retinal detachment. In some embodiments, the subject for treatment with the composition has suffered a primary retinal detachment. In some embodiments, the subject for treatment has a primary retinal detachment which is a rhegmatogenous retinal detachment. In some embodiments, subject for treatment with the MTX composition has suffered a secondary retinal detachment. In some embodiments, the subject for treatment with the MTX composition has suffered a rhegmatogenous retinal detachment, tractional retinal detachment, or a combined tractional-rhegmatogenous retinal detachment. In some embodiments, the subject for treatment with the MTX composition has an open-globe injury.

In some embodiments, the retinal detachment is a localized retinal detachment, and in some embodiments, the retinal detachment is a complete retinal detachment. In some embodiments, the method comprises administering to an eye of a subject afflicted with retinal detachment a therapeutically effective amount of a MTX composition of the present disclosure.

In some embodiments, the subject for treatment with the MTX composition has undergone treatment for a retinal detachment. In some embodiments, the method comprises administering to an eye of a subject treated for retinal detachment a therapeutically effective amount of a MTX composition of the present disclosure. In some embodiments, the subject for treatment with the MTX composition has undergone laser surgery (e.g., photocoagulation, laser retinopexy, etc.) for treatment of the retinal tear or hole associated with retinal detachment. In some embodiments, the subject for treatment with the MTX composition has undergone cryopexy for treatment of the retinal tear or hole associated with the retinal detachment. In some embodiments, the subject for treatment with the MTX composition has undergone pneumatic retinopexy to treat retinal detachment. In some embodiments, the subject for treatment with the MTX composition has undergone scleral buckling to treat retinal detachment. In some embodiments, the subject for treatment with the MTX composition has undergone a vitrectomy to treat retinal detachment, e.g., pars plana vitrectomy (PPV) with an intraocular tamponade, such as gas or silicone oil.

In some embodiments, the subject for treatment with the MTX composition is administered or has been administered intravitreally SiO in the affected eye, such as a tamponade for treating retinal detachment. In some embodiments, the SiO administered is SiO having a viscosity of at least 1000 centistoke. In some embodiments, the SiO administered has a viscosity of about 1000 to about 5000 centistoke. In some embodiments, the SiO administered is 1000 centistoke oil, in particular polydimethyl siloxane 1000 centistoke oil. In some embodiments, the SiO administered is 5000 centistoke oil, in particular polydimethyl siloxane 5000 centistoke oil.

In some embodiments, the subject for treatment with the MTX composition is administered or has been administered intravitreally heavy silicone oil (HSO), such as a tamponade for treating inferior retinal detachment. In some embodiments, the HSO is Oxane HD, Densiron 68, or HSV-45 3000. In some embodiments, the eye of the subject for treatment is administered or has been administered intravitreally perfluorocarbon liquids (PFCLs) or semifluorinated alkanes, such as perfluorohexyloctane (F6H8). PFCLs include perfluoro-n-octane (C8F18) and perfluorodecalin (C10F18).

In some embodiments, the MTX composition is administered by intravitreal injection into the SiO of a subject who has been treated with intravitreal SiO. In some embodiments, the MTX composition is co-administered with the SiO administered to the eye treated with the SiO and MTX composition. In some embodiments, the composition is present in the SiO when the SiO is administered into the posterior segment.

In some embodiments, the subject for treatment with the MTX composition has one or more risk factors for rhegmatogenous retinal detachment. In some embodiments, the subject for treatment with the MTX compositions has a prior history of one or more of the following: chronic ocular inflammation, infectious retinitis, multiple retinal detachments, large retinal breaks or giant retinal tears, multiple retinal breaks, ocular trauma, retinal detachment associated with vitreous hemorrhage, choroidal detachment, and combinations thereof.

In some embodiments, the subject for treatment with the MTX composition is characterized by vitreous or subretinal hemorrhage, excessive cryotherapy, pigment release during endodrainage, or combinations thereof.

In some embodiments, the compositions described herein can be used to treat other ocular diseases, disorders, or conditions that would benefit from treatment with methotrexate.

In some embodiments, the compositions herein are used to treat intraocular lymphoma. In some embodiments, a method of treating intraocular lymphoma comprises administering intravitreally to an eye of a subject with intraocular lymphoma a therapeutically effective amount of a composition disclosed herein, including the exemplary formulations disclosed herein.

In some embodiments, the intraocular lymphoma treated is primary vitreoretinal lymphoma (PVRL). Thus, the subject is afflicted or diagnosed with PVRL. In some embodiments, the intraocular lymphoma (e.g., PVRL) is accompanied by cerebral nervous system lymphoma (PCNSL). In some embodiments, the intraocular lymphoma is diffuse large B-cell lymphoma.

Administration and dosages for treatment of intraocular lymphoma are provided in more detail herein.

In addition to the disorders or PVR and intraocular lymphoma, the MTX compositions disclosed herein can also be used to treat inflammatory diseases, disorders, or conditions of the eye, particularly intraocular inflammation. In some embodiments, a method of treating intraocular inflammation comprises administering intravitreally to an eye of a subject with intraocular inflammation a therapeutically effective amount of a composition disclosed herein, including the exemplary formulations disclosed herein.

In some embodiments, the inflammatory diseases, disorders, or conditions for treatment with the MTX compositions herein include, among others, uveitis, for example pan uveitis, intermediate uveitis, and posterior uveitis, particularly non-infectious posterior uveitis; cystoid macular edema (CME); macular edema, for example accompanying uveitis or diabetic macular edema; choroidal neovascularization; and prosthetic membranopathy.

Administration and dosages for treatment of intraocular inflammation are provided in more detail herein.

1.3. Administration and Dosages

In some embodiments, the methods or use described herein include the use of a "therapeutically effective amount" of MTX composition described herein. A "therapeutically effective amount" refers to an amount sufficient to effect beneficial or desired results.

In some embodiments, the eye of the subject in need thereof is administered a therapeutically effective amount, which includes a prophylactically effective amount of the MTX composition of the present disclosure that prevents or reduces the risk of developing PVR. In some embodiments, the eye of the subject in need thereof is administered a therapeutically effective amount of the MTX composition of the present disclosure to treat PVR.

In some embodiments, the eye of the subject in need thereof is administered a therapeutically effective amount of the MTX composition of the present disclosure to treat intraocular lymphoma. In some embodiments, the eye of the subject in need thereof is administered a therapeutically effective amount of the MTX composition of the present disclosure to treat PVRL.

In some embodiments, the eye of the subject in need thereof is administered a therapeutically effective amount of the MTX composition of the present disclosure to prevent, reduce the risk of, or treat intraocular inflammation. In some embodiments, the eye of the subject in need thereof is administered a therapeutically effective amount of the MTX composition of the present disclosure to treat intraocular inflammation.

The amount of MTX administered can take into consideration, among others, the type of disease, disorder, or condition being treated (e.g., the nature or location of damage to the eye; the extent of intraocular lymphoma; or types of intraocular inflammation), the age and sex of the subject, the presence of risk factors, and the type of treatment given to the subject to treat the eye.

A therapeutically effective amount can be administered in one or more administrations, applications, or dosages. In some embodiments, the eye of the subject is administered the MTX composition described herein sufficient to deliver MTX at a dose of about 25 µg to about 600 µg. In some embodiments, the eye of the subject is administered a dose of MTX of about 30 µg to about 580 µg, about 35 µg to about 560 µg, about 40 µg to about 540 µg, about 45 µg to about 520 µg, about 50 µg to about 500 µg, about 60 µg to about 480 µg, about 70 µg to about 460 µg, about 80 µg to about 440 µg, about 90 µg to about 430 µg, about 100 µg to about 420 µg, about 120 µg to about 400 µg, about 140 µg to about 380 µg, about 160 µg to about 360 µg, about 180 µg to about 340 µg, or about 200 µg to about 320 µg, In some embodiments, the dose of MTX is about 200 µg to about 600 µg, or about 300 µg to about 500 µg.

In some embodiments, the eye of the subject is administered a dose of MTX of about 25 µg, about 30 µg, about 35 µg, about 40 µg, about 45 µg, about 50 µg, about 60 µg, about 65 µg, about 70 µg, about 75 µg, about 80 µg, about 85 µg, about 90 µg about 95 µg, about 100 µg, about 110 µg, about 120 µg, about 130 µg, about 140 µg, about 150 µg, about 160 µg, about 170 µg, about 180 µg, about 190 µg, about 200 µg, about 210 µg, about 220 µg, 230 µg, 240 µg, 250 µg, 260 µg, 270 µg, 280 µg, 290 µg, about 300 µg, about 320 µg, about 340 µg, about 360 µg, about 300 µg, about 350 µg, about 400 µg, about 450 µg, about 500 µg, about 550 µg, or about 600 µg. Preferably, the dose of MTX is about 200 µg, 300 µg, 400 µg, or about 500 µg.

In some embodiments for intravitreal administration, the volume of composition administered is suitable for intravitreal administration. By way of example and not limitation, the volume can be adjusted if the administration is intravitreally into gas or SiO filled eye. In some embodiments, the volume of composition administered is about 20 µl to about 300 µl, about 25 µl to about 200 µl, about 30 µl to about 190 µl, about 35 µl to about 180 µl, about 40 µl to about 170 µl, about 45 µl to about 150 µl, about 50 µl to about 140 µl, about 55 µl to about 130 µl, about 60 µl to about 120 µl, about 70 µl to about 110 µl, or about 80 µl to about 100 µl.

In some embodiments for intravitreal administration, the volume of composition administered is about 25 µl, about 30 µl, about 35 µl, about 40 µl, about 45 µl, about 50 µl, about 60 µl, about 70 µl, about 80 µl, about 90 µl, about 100 µl, about 120 µl, about 140 µl, about 160 µl, about 180 µl, about 200 µl, about 220 µl, about 240 µl, about 260 µl, about 280 µl, or about 300 µl. An exemplary volume for intravitreal administration is 100 µl.

In some embodiments, a volume of about 0.5 mL or less per dose of the composition is administered. In some embodiments, a volume of 5 µL to 0.5 mL per dose of the composition is administered. In some embodiments, a volume of 10 µL to 0.4 mL per dose of the composition is administered. In some embodiments, a volume of 15 µL to 0.3 mL per dose of the composition is administered. In some embodiments, a volume of 20 µL to 0.2 mL per dose of the composition is administered. In some embodiments, a volume of 25 µL to 0.1 mL per dose of the composition is administered.

In other embodiments, a volume of about 100 µL or less per dose of the composition is administered. In some embodiments, a volume of 5 µL to 95 µL per dose of the composition is administered. In some embodiments, a volume of 15 µL to 85 µL per dose of the composition is administered. In some embodiments, a volume of 25 µL to 75 µL per dose of the composition is administered. In some embodiments, a volume of 35 µL to 65 µL per dose of the composition is administered. In some embodiments, a volume of 45 µL to 55 µL per dose of the composition is administered.

In some embodiments, a volume of 50 µL±10 µL per dose of the composition is administered. In some embodiments, a volume of 50 µL±10 µL per dose of the composition is administered. In some embodiments, a volume of about 50 µL per dose of the composition is administered.

In some embodiments, the MTX composition is administered at a frequency and duration to provide a prophylactic effect or to treat a disease, disorder, or condition disclosed herein in the affected eye.

In some embodiments, the MTX composition is administered at a frequency and duration to provide a prophylactic effect or to treat PVR.

In some embodiments for treating PVR, the dose, frequency, and duration can be adjusted taking into consideration factors such as, among others, extent of retinal injury, location of the retinal injury, type of surgery used to treat the eye damage, the age and sex of the subject, duration of tamponade needed with gas or SiO, and presence of one or more risk factors for PVR. In some embodiments, the MTX composition is administered once a day, once every two days, once every three days, once every four days, once every five days, once every 6 days, or once every seven days. In some embodiments, the MTX composition is administered once every week, or once every 2 weeks, once every three weeks, or once a month.

In some embodiments, the following is used to treat PVR. In some embodiments, the MTX composition is administered more than once per day, for example two times per day or three times per day. In some embodiments, the subject is administered the MTX composition twice or three times per day postoperatively, for example, in the day surgery has been completed, and/or 1 day, 2 days, 3 days or 4 days following surgical treatment.

In some embodiments, the MTX composition can be administered at least once a day for 3, 4, 5, 6, or 7 days following initial retinal damage and/or post-operative surgery followed by a lower frequency of administration. In some embodiments, the MTX composition is administered at least once a day for at least for two weeks followed by a lower frequency of administration.

In some embodiments, the duration of treatment is for at least 2 days, at least 3 days, at least 4 days, at least 5 days, at least 6 days, at least one week, at least two weeks, at least 3 weeks, at least 1 month, at least 2 months, at least 3 months, at least 4 months, at least 5 months, at least 6 months, at least 7 months, at least 8 months, at least 9 months, at least 10 months, or at least 12 months (i.e., one year). In some embodiments, where the treatment involves gas or SiO, e.g., as a tamponade, the treatment duration is until completion of treatment with the gas or removal of the SiO, respectively. In some embodiments, the treatment with the MTX composition is continued following completion of treatment with the gas or removal of the SiO, for example where the subject has one or more risk factors for PVR.

In some embodiments, intravitreal administration of the MTX composition for treating a disease, disorder, or condition described herein is performed according to standard methods used in the art. In some embodiments, intravitreal administration is performed aseptically after the topical application of anesthesia and an antiseptic agent, e.g., 5% povidone iodine, to the conjunctival sac. In some embodiments, eye of the subject is administered an intravitreal injection of the MTX composition, for example with a 19-26 gauge or 30-gauge needle.

In some embodiments for treating PVR, where the MTX composition is administered intravitreally into SiO in the eye, the subject is maintained in an appropriate position (e.g., lying face up) following administration of SiO, for the MTX composition to transit through the SiO, and in some embodiments, sufficient time for transit through the SiO and dispersion of the MTX composition in the aqueous phase for adsorption into the retinal tissues, especially over the posterior pole. In some embodiments, the patient may be positioned in other positions (e.g., lying on one's side) to direct the methotrexate to a specific area. In some embodiments, the subject is positioned appropriately for at least 30 min, at least 25 min, at least 20 min, at least 15 min, at least 10 min, or at least 5 min following administration of the MTX composition into the SiO.

In some embodiments, the MTX composition is administered at a frequency and duration to effective to treat intraocular lymphoma, e.g., PVRL.

In some embodiments for treating intraocular lymphoma, the dose, frequency, and duration can be adjusted taking into consideration factors such as, among others, the severity or stage of the intraocular lymphoma and other conditions, such as the presence or absence of accompanying PCNSL. In some embodiments, the MTX composition is administered once every 4 weeks (month), once every two weeks, once a week, two times a week, three times a week, or four times a week to treat intraocular lymphoma.

In some embodiments for treating intraocular lymphoma, the treatment regimen includes an induction phase, and optionally a consolidation phase, and/or a maintenance phase.

In some embodiments, the induction phase is administration of the MTX composition two times a week, up to four times a week.

In some embodiments, the consolidation phase, when present, comprises administration once a week or two times a week.

In some embodiments, the maintenance phase, when present, comprises administration once every two weeks or once every month.

In some embodiments for treating intraocular lymphoma, the dose administered is sufficient to provide a therapeutic effect. In some embodiments, any of the doses disclosed above can be used in an effective amount for treating intraocular lymphoma. In some embodiments, the dose of MTX administered is about 100 to 800 µg, about 200 to 600 µg, or about 300 to 500 µg.

In some embodiments, the dose of MTX administered for treating intraocular lymphoma is about 100 µg, about 200 µg, about 300 µg, about 400 µg, about 500 µg, about 600 µg, about 700 µg, or about 800 µg. In preferred embodiments, the dose of MTX administered is about 200 µg, about 300 µg, about 400 µg, or about 500 µg. In some embodiments, the dose of MTX administered is about 400 µg.

In some embodiments for treating intraocular lymphoma, the dose administered is sufficient to provide a therapeutic effect. In some embodiments, the dose of MTX administered is about 100 to 800 µg/0.1 mL, about 200 to 600 µg/0.1 mL, or about 300 to 500 µg/0.1 mL.

In some embodiments, the dose of MTX administered for treating intraocular lymphoma is about 100 µg/0.1 mL, about 200 µg/0.1 mL, about 300 µg/0.1 mL, about 400 µg/0.1 mL, about 500 µg/0.1 mL, about 600 µg/0.1 mL, about 700 µg/0.1 mL, or about 800 µg/0.1 mL. In preferred embodiments, the dose of MTX administered is about 200 µg/0.1 mL, about 300 µg/0.1 mL, about 400 µg/0.1 mL, or about 500 µg/0.1 mL. In some embodiments, the dose of MTX administered is about 400 µg/0.1 mL.

In some embodiments for treating intraocular lymphoma, the treatment with MTX is in combination with a secondary therapeutic agent effective for treatment of the lymphoma. In some embodiments, the secondary therapeutic administered in combination with the MTX is an anti-CD20 antibody. In some embodiments, the anti-CD20 antibody is selected from rituximab, ocrelizumab, veltuzumab, obinutuzumab, and ofatumumab.

In some embodiments, the MTX composition is administered at a frequency and duration to effective to treat intraocular inflammation. In some embodiments, the intraocular inflammation for treatment is uveitis, for example pan uveitis, intermediate uveitis, or posterior uveitis, particularly non-infectious posterior uveitis; cystoid macular edema (CME); macular edema, for example accompanying uveitis, or diabetic macular edema; choroidal neovascularization; and prosthetic membranopathy.

In some embodiments for treating intraocular inflammation, the dose, frequency, and duration can be adjusted taking into consideration factors such as, among others, the type of intraocular inflammation, and the severity or stage of the intraocular inflammation. In some embodiments, the MTX composition is administered once every 4 weeks (month), once every two weeks, once a week, two times a week, three times a week, or four times a week to treat intraocular inflammation.

In some embodiments for treating intraocular inflammation, the treatment regimen includes an induction phase, and optionally a consolidation phase, and/or a maintenance phase.

In some embodiments, the induction phase is administration of the MTX composition two times a week, up to four times a week.

In some embodiments, the consolidation phase, when present, comprises administration once a week or two times a week.

In some embodiments, the maintenance phase, when present, comprises administration once every two weeks or once every month.

In some embodiments for treating intraocular inflammation, the dose administered is sufficient to provide a therapeutic effect. In some embodiments, any of the doses disclosed above can be used in an effective amount for treating intraocular inflammation. In some embodiments, the dose of MTX administered is about 100 to 800 µg, about 200 to 600 µg, or about 300 to 500 µg.

In some embodiments, the dose of MTX administered for treating intraocular inflammation is about 100 µg, about 200 µg, about 300 µg, about 400 µg, about 500 µg, about 600 µg, about 700 µg, or about 800 µg. In particular embodiments, the dose of MTX administered is about 200 µg, about 300 µg, about 400 µg, or about 500 µg. In particular embodiments, the dose of MTX administered is 400 µg.

In some embodiments for treating intraocular inflammation, the dose administered is sufficient to provide a therapeutic effect. In some embodiments, the dose of MTX administered is about 100 to 800 µg/0.1 mL, about 200 to 600 µg/0.1 mL, or about 300 to 500 µg/0.1 mL.

In some embodiments, the dose of MTX administered for treating intraocular inflammation is about 100 µg/0.1 mL, about 200 µg/0.1 mL, about 300 µg/0.1 mL, about 400 µg/0.1 mL, about 500 µg/0.1 mL, about 600 µg/0.1 mL, about 700 µg/0.1 mL, or about 800 µg/0.1 mL. In preferred embodiments, the dose of MTX administered is about 200 µg/0.1 mL, about 300 µg/0.1 mL, about 400 µg/0.1 mL, or about 500 µg/0.1 mL. In some embodiments, the dose of MTX administered is about 400 µg/0.1 mL.

1.4. Viscosity Enhancing Agents and Hyaluronate Formulations

In some embodiments, the pharmaceutical composition comprises any of the compounds above and a viscosity enhancing agent. In some embodiments, the pharmaceutical composition has a viscosity sufficient to reduce substantial diffusion of the therapeutic agent contained therein from the site at which the composition is administered and/or to provide delayed release of the compound. A suitable viscosity enhancing agent is selected from, among others, hyaluronate, hyaluronic acid or pharmaceutically acceptable salt thereof; cross-linked hyaluronic acid; polyvinylpyrrolidone (PVP); hydroxypropyl methylcellulose, hydroxypropyl cellulose, hydroxylethyl cellulose, glycerol; and mixtures thereof. In some embodiments, a viscosity enhancing agent is selected that does not have reactive aldehyde groups capable of reacting with the compounds described herein.

In some embodiments, the viscosity enhancing agent is sodium hyaluronate, polyvinylpyrrolidone (PVP), sodium hydroxypropyl cellulose, or hydroxypropyl methylcellulose. The viscosity enhancing component is present in an amount effective in providing the desired viscosity to the composition.

In some embodiments, the amount of the viscosity enhancing agent is based on the agent used, and is in general in an amount of about 0.05 to 30% w/v. In some embodiments, the concentration of viscosity enhancing agent is about 0.05 to 30% w/v, about 0.1% w/v to about 25% w/v, about 0.25% w/v to about 15% w/v, about 0.5% w/v to about 15% w/v, about 0.75% w/v to about 10% w/v, or about 1.0% w/v to about 5% w/v.

In some embodiments, the amount of the viscosity enhancing agent in the pharmaceutical composition is 0.05% w/v to 1.5% w/v; 0.05% w/v to 0.5% w/v; 0.1% w/v to 3.0% w/v; 0.1% w/v to 1.5% w/v; 0.1% w/v to 1.0% w/v; 0.5% w/v to 1% w/v; 0.5% w/v to 2.5% w/v; 1.0% w/v to 3.0% w/v; 1.0% w/v to 1.5% w/v; 1.0% w/v to 1.25% w/v; 1.25% w/v to 1.5% w/v; or 1.5% w/v to 3.0% w/v.

In some embodiments, the amount of the viscosity enhancing agent in the pharmaceutical composition is about 0.1% w/v, about 0.25% w/v, about 0.5% w/v, about 0.75% w/v, about 1.0% w/v, about 1.1% w/v, about 1.15% w/v, about 1.20% w/v, about 1.25% w/v, about 1.30% w/v, about 1.35% w/v, about 1.40% w/v, about 1.45% w/v, about 1.5% w/v, about 2% w/v, about 3% w/v, about 4% w/v, about 5% w/v, about 10% w/v, about 15% w/v, about 20% w/v, about 25% w/v, or about 30% w/v.

In some embodiments, the molecular weight of a viscosity enhancing agent when polymeric is about 500,000 to about $5 \times 10^6$ Daltons; about 500,000 Daltons to about $3 \times 10^6$ Daltons; about 500,000 to about $2 \times 10^6$ Daltons; about 500,000 to about $1 \times 10^6$ Daltons; about 500,000 to about $2 \times 10^6$ Daltons; about $1 \times 10^6$ Daltons to about $3 \times 10^6$ Daltons; about $1 \times 10^6$ Daltons to about $2.5 \times 10^6$ Daltons; about $1 \times 10^6$ Daltons to about $2 \times 10^6$ Daltons; or about $1.2 \times 10^6$ Daltons to about $1.8 \times 10^6$ Daltons. In some embodiments, the molecular weight is the number average molecular weight, and in other embodiments, the molecular weight is the weight average molecular weight.

In some embodiments, the viscosity of the pharmaceutical composition is about 300 kcP, about 250 kcP, about 200 kcP, about 150 kcP, about 140 kcP, about 130 kcP, about 120 kcP, about 110 kcP, about 100 kcP, about 90 kcP, about 80 kcP, about, 70 kcP, about 40 kcP, about, 30 kcP, about 25 kcP, about 20 kcP, about 10 kcP, about 5 kcP, or about 1 kcP.

In some embodiments, the viscosity of the composition is about 1 kcP to about 300 kcP; about 1 kcP to about 200 kcP, about 1 kcP to about 100 kcP; about 1 kcP to about 50 kcP; about 1 kcP to about 10 kcP; about 10 kcP to about 50 kcP; about 10 kcP to about 100 kcP; about 50 kcP to about 100 kcP; about 100 kcP to about 300 kcP; about 50 kcP to about 200 kcP; about 75 kcP to about 180 kcP; about 100 kcP to about 150 kcP; about 150 kcP to about 200 kcP; about 200 kcP to about 250 kcP; or about 250 kcP to about 300 kcP.

In some embodiments, the pharmaceutical composition comprises a compound of the present disclosure and hyaluronic acid or a pharmaceutically acceptable salt of the hyaluronic acid. Hyaluronic acid is a glycosaminoglycan, whose molecular weight can vary from 50,000 Daltons to about 8,000,000 Daltons and forms highly viscous solutions. In some embodiments, the hyaluronic acid contained in the formulation can be, either in its acid form or in the form of one of its pharmaceutically acceptable salts, such as an alkali metal or alkaline-earth metal hyaluronate, for instance sodium hyaluronate, potassium hyaluronate, magnesium hyaluronate, calcium hyaluronate or others. In some embodiments, the hyaluronic acid is in the form of sodium hyaluronate. In some embodiments, the hyaluronate is sodium hyaluronate solution in combination with a citric acid salt, for example tri-sodium citrate.

In some embodiments of the pharmaceutical compositions, the hyaluronate is a high molecular weight (HMW) hyaluronic acid or a pharmaceutically acceptable salt thereof. As used herein, HMW hyaluronic acid refers to a hyaluronic acid material having a molecular weight of at least about $1 \times 10^6$ to about $5 \times 10^6$ Daltons. In some embodiments, the HMW hyaluronic acid is $1 \times 10^6$ to about $5 \times 10^6$ Daltons; $1.5 \times 10^6$ to about $4 \times 10^6$ Daltons, $2 \times 10^6$ to about $4 \times 10^6$ Daltons; $2 \times 10^6$ to about $4 \times 10^6$ Daltons; $1 \times 10^6$ to about $3 \times 10^6$ Daltons; or $1.5 \times 10^6$ to about $2 \times 10^6$ Daltons. In some embodiments, the HMW hyaluronic acid in the pharmaceutical compositions can have a molecular weight of about $1 \times 10^6$ Daltons. In some embodiments, the HMW hyaluronic acid can have a molecular weight of about $2.8 \times 10^6$ Daltons. In some embodiments, the hyaluronic acid or its salt has a weight-average molecular weight that is not below $1\times10^6$ Daltons, more preferably an average molecular weight in the range of $1.3\times10^6$ to $3\times10^6$ Daltons. In some embodiments, the molecular weight is about $1.7\times10^6$ Daltons.

In some embodiments, the hyaluronate is a low molecular weight (LMW) hyaluronic acid or a pharmaceutically acceptable salt thereof. As used herein, a LMW hyaluronic acid refers to hyaluronic acid material having a molecular weight of less than about $1\times10^6$ Daltons. In some embodiments, the LMW hyaluronic acid can have a molecular weight of between about 200,000 to less than about $1\times10^6$ Daltons, for example, between about 300,000 to about 750,000 Daltons. In some embodiments, an average molecular weight is less than about 750,000. In some embodiments, the average molecular weight of the hyaluronate component is in a range of about 50,000 or about 100,000 Daltons to about 750,000 Daltons.

In some embodiments, an average molecular weight of the hyaluronic acid or salt thereof is in a range of about 10,000 Daltons or less to about $2\times10^6$ Daltons. In some embodiments, the average molecular weight of the hyaluronic acid is in a range of about 100,000 Daltons or about 200,000 Daltons to about $1\times10^6$ Daltons, or to about $1\times10^6$ Daltons. In some embodiments, the molecular weight of the hyaluronic acid component can be varied over a substantial range to obtain the desired final viscosity of the composition. In some embodiments, two or more distinct molecular weight ranges of the hyaluronic acid may be used to increase the shear thinning attributes of the composition. In some embodiments, the hyaluronate is a metal hyaluronate component, preferably selected from alkali metal hyaluronates, alkaline earth metal hyaluronates and mixtures thereof, and still more preferably selected from sodium or potassium hyaluronates, and mixtures thereof.

In some embodiments, the molecular weight of the hyaluronate or hyaluronic acid or a pharmaceutically acceptable salt thereof is about 500,000 to about $5\times10^6$ Daltons; about 500,000 to about $3\times10^1$ Daltons; about 500,000 to about $2\times10^6$ Daltons; about 500,000 to about $1\times10^6$ Daltons; about 500,000 to about $2\times10^6$ Daltons; about $1\times10^6$ to about $3\times10^6$ Daltons; about $1\times10^6$ to about $2.5\times10^6$ Daltons; about $1\times10^6$ to about $2\times10^6$ Daltons; or about $1.2\times10^6$ to about $1.8\times10^6$ Daltons.

In some embodiments, the amount of hyaluronate in the pharmaceutical composition is about 0.05% w/v; about 0.1% w/v, about 0.25% w/v, about 0.5% w/v, about 0.75% w/v, about 1.0% w/v, about 1.1% w/v, about 1.15% w/v, about 1.20% w/v, about 1.25% w/v, about 1.30% w/v, about 1.35% w/v, about 1.40% w/v, about 1.45% w/v, about 1.5% w/v; about 2% w/v; about 2.5% w/v; about 3% w/v; about 3.5% w/v; or about 4% w/v.

In some embodiments, the amount of hyaluronate in the pharmaceutical composition is about 0.05% w/v to about 1.5% w/v; about 0.05% w/v to about 0.5% w/v; about 0.10% w/v to about 4.0% w/v; about 0.10% w/v to about 3.0% w/v; about 0.10% w/v to about 1.50% w/v; about 0.1% w/v to about 1.0% w/v; about 0.5% w/v to about 1% w/v; about 0.5% w/v to about 2.5% w/v; about 1.0% w/v to about 3.0% w/v; about 1.0% w/v to about 1.5% w/v; about 1.0% w/v to about 1.25% w/v; about 1.25% w/v to about 1.5% w/v; or about 1.5% w/v to about 3.0% w/v.

In some embodiments, the hyaluronate is in an amount in a range about 0.05% to about 0.5% (w/v). In some embodiments, the hyaluronate is present in an amount in a range of about 1% to about 4% (w/v). At the higher concentrations, the high viscosity can result in a gel that slows particle sedimentation and diffusion of dissolved solutes, such as upon injection into the eye. Such a composition can be provided in pre-filled syringes for ease of administration.

In some embodiments, the hyaluronic acid is a cross-linked hyaluronic acid. In some embodiments, the hyaluronic acid is present at about 50% to 99% by weight, or 70% to 95% by weight in the form of a crosslinked hyaluronic acid, from 1% to 50% by weight, preferably 5% to 30% by weight, of hyaluronic acid present in the free form or a pharmaceutically acceptable salt thereof. In some embodiments where the hyaluronic acid is crosslinked, the crosslinked hyaluronic acid can have a degree of modification ranging from 0.1 to 20%, preferably from 0.4 to 10%. In some embodiments, the cohesive, crosslinked hyaluronic-based gel includes no greater than about 1% to about 10% of free hyaluronic acid material by volume, for example, no greater than about 5% free hyaluronic acid material.

In some embodiments, the cross-linked hyaluronic acid can be prepared by, among others, use of dihyrazides, photocrosslinking, enzymatic cross-linking, expoxidic crosslinks, and click chemistry. The "degree of modification" refers to the ratio between the number of moles of crosslinking agent attached to the hyaluronic acid and the number of moles of hyaluronic acid forming said cross-linked hyaluronic acid gel. Free hyaluronic acid is generally water soluble, and as used herein, can be defined as the "uncrosslinked," or lightly crosslinked component of the macromolecular structure. Crosslinked hyaluronic acid and methods of their preparation are described in, among others, Schramm et al., 2012, Invest Ophthalmol Vis Sci. 53:613-621; Schramm et al., 2011, Invest Ophthalmol Vis Sci. 52:452; Egbu et al., 2018, Eur J Pharm Biopharm. 124:95-103; U.S. Pat. Nos. 8,357,795; 9,925,309; all of which are incorporated herein by reference in their entireties.

In some embodiments, the viscosity enhancing agent is hyaluronic acid crosslinked with dextran (see, e.g., Yu et al., 2015, Transl Vis Sci Technol. 4(2):5; incorporated herein by reference). Synthesis of hyaluronic acid crosslinked with dextran can be carried out by chemical crosslinking between functionalized hyaluronic acid and thiolated dextran. In some embodiments, the viscosity enhancing agent is a copolymer of hyaluronic acid and poly(glyceryl glycerol) (PGG) side chains attached via hydrolysable ester linkers (see, e.g., Borke et al., 2018, Macromolecular Bioscience 18:1700200; incorporated herein by reference).

In some embodiments, for intraocular, e.g., intravitreal, formulations, the intraocular dosage composition of hyaluronate has a viscosity sufficient to reduce substantial diffusion of the drug contained therein from the site at which the composition is administered. In some embodiments, the pharmaceutical compositions have viscosity of at least about 10 cps or at least about 100 cps or at least about 1000 cps, more preferably at least about 10,000 cps and still more preferably at least about 70,000 cps or more, for example up to about 200,000 cps or about 250,000 cps, or about 300,000 cps or more, at a shear rate of 0.1/second. In some embodiments, the composition has sufficient viscosity to be structured or formed but injectable into a posterior segment of an eye of a human or animal, for example through a 27 gauge needle, or even through a 30 gauge needle.

In some embodiments, the pharmaceutical composition comprising a compound disclosed herein and a viscosity enhancing agent, further comprises one or more excipients. In some embodiments, the excipient is one or more of tonicity agent, buffering agent, chelating agent, surfactant, preservative, antioxidant, and an additional viscosity enhancing agent different from the first viscosity enhancing agent.

In some embodiments, the pharmaceutical composition further comprises a tonicity agent. In some embodiments, the pharmaceutical composition further comprises a buffering agent. In some embodiments, the pharmaceutical composition further comprises a chelating agent. In some embodiments, the pharmaceutical composition further comprises a surfactant. In some embodiments, the pharmaceutical composition further comprises a preservative. In some embodiments, the pharmaceutical composition further comprises an antioxidant. In some embodiments, the pharmaceutical composition further comprises an additional viscosity enhancing agent different from the first viscosity enhancing agent. In some embodiments, the excipients are suitable for intraocular, e.g., intravitreal, administration.

1.5. Liposomal Formulations

In some embodiments, a pharmaceutical composition comprises a compound of the disclosure formulated in a liposome. Liposomes are artificial, self-closed vesicular structures of various sizes and structures, where one or several membranes encapsulate an aqueous core. In some embodiments, liposome compositions are selected that do not have aldehyde groups capable of reacting with the compounds described herein.

In some embodiments, the types of liposomes include, multilamellar vesicles (MLV) or oligolamellar vesicles (OLV), unilamellar vesicles (SUV) and large unilamellar vesicles (LUV). Generally, a unilamellar liposome is a liposome having a single bilayer of an amphiphilic lipid or a mixture of such lipids, containing aqueous solution inside the chamber. Generally, MLVs have more than one lipid bilayer, where the lipid bilayers in MLVs are separated from the one another other by an aqueous solution.

In some embodiments, small unilamellar liposomes/ vesicles (SUVs) have diameters up to 100 nm, for example 20 um to about 100 um; large unilamellar liposomes/vesicles (LUVs) can have diameters greater than 100 nm, and up to micrometers (μm), the latter sometimes referred to as giant unilamellar vesicles (GUV). MLVs can have diameters of 200 nm to 3 um, for example greater than 0.5 um. In some embodiments, the diameter is a mean diameter. As used herein, "mean diameter" refers generally to a mathematical average of a set of diameters, each diameter being taken for each liposome in a liposome population.

In some embodiments, the pharmaceutical composition comprises a compound of the disclosure formulated in a liposome, preferably as small unilamellar vesicles (SUV) or large unilamellar vesicles (LUV) or multilamellar vesicles (MLV). In some embodiments, the liposomes have a mean diameter of less than about 1 um (i.e., submicron-sized liposomes).

In some embodiments, the liposomes have a mean diameter of about 20 nm to about 1 um or less; about 20 nm to about 900 nm; about 20 nm to about 800 nm; about 20 nm to about 700 nm, about 20 nm to about 600 nm; about 20 nm to about 500 nm; about 20 nm to about 450 nm; about 20 nm to about 400 nm; about 20 nm to about 350 nm; about 20 nm to about 300 nm; about 20 nm to about 250 nm; about 20 nm to about 200 nm; about 20 nm to about 150 nm; about 20 nm to about 125 nm; about 20 nm to about 100 nm; about 20 nm to about 80 nm; about 20 nm to about 70 nm; or; about 20 nm to about 50 nm.

In some embodiments, the liposomes have a mean diameter of about 50 nm to about 900 nm; about 50 nm to about 800 nm; about 50 nm to about 700 nm; about 75 nm to about 600 nm; about 75 nm to about 500 nm; about 100 nm to about 400 nm; or 100 nm to about 300 nm.

In some embodiments, the liposome has a size of or less than about 1 um, 900 nm, 850 nm, 800 nm; 750 nm; 700 nm; 650 nm; 600 nm; 550 nm; 500 nm, 450 nm, 400 nm, 350 nm, 300 nm, 250 nm, 200 nm, 150 nm, 125 nm, 110 nm, 100 nm, 95 nm, 90 nm, 85 nm, 80 nm, 75 nm, 70 nm, 65 nm, 60 nm, 55 nm, 50 nm, 40 nm, 30 nm, or 20 nm.

In the context of various embodiments, the term "liposomal formulation" refers to a formulation of liposomes, wherein liposomes are artificially prepared vesicles made of lipid bilayer. Lipid bilayer may be in a form of a single or one lipid bilayer, or of multiple lipid bilayers. Liposomes may be filled or loaded with drugs. Generally, the liposomes are composed of amphiphilic lipids, such as phospholipids, of natural or synthetic origin. In some embodiments, the membrane properties can be modified by the incorporation of other lipids such as sterols or cholic acid derivatives. In some embodiments, the liposomes comprise one or more of fatty acyls, glycerolipids, phospholipids, glycerophospholipids, sphingolipids, sterol lipids, preno lipids, saccharolipids, and polyketide lipids.

In some embodiments, the liposome comprises a lipid, wherein the lipid includes one or more of phosphatidylcholines, phosphatidylethanolamines, phosphatidic acids, gangliosides, glycolipids, phosphatidylglycerols, and cholesterol. The phosphatidylcholines include, among others, dimyristoylphosphatidylcholine, dipalmitoylphosphatidylcholine, and distearoylphosphatidylcholine. The phosphatidylethanolamines include, among others, dimyristoylphosphatidylethanolamine, dipalmitoylphosphatidylethanolamine, and distearoylphosphatidylethanolamine. The phosphatidic acids include, among others, dimyristoylphosphatidic acid, dipalmitoylphosphatidic acid, distearoylphosphatidic acid, and dicetylphosphoric acid. The gangliosides include, among others, ganglioside GM1, ganglioside GDla, and ganglioside GT1b. The glycolipids include, among others, galactosylceramide, glucosylceramide, lactosylceramide, phosphatide, and globoside. The phosphatidylglycerols include, among others, dimyristoylphosphatidylglycerol, dipalmitoylphosphatidylglycerol, and distearoylphosphatidylglycerol.

In some embodiments, the phosphatidylcholine is selected from L-α-phosphatidylcholine, egg phosphatidylcholines (EPC), 1,2-dioleoyl-sn-glycero-3-phosphocholines (DOPC), 1,2-dioleoyl-sn-glycero-O-ethyl-3-phosphocholines, 1,2-dilauroyl-sn-glycero-3-phosphocholines (DLPC), 1,2-dimyristoyl-sn-glycero-3-phosphocholines (DMPC), 1,2-dipalmitoyl-sn-glycero-3-phosphocholines (DPPC), 1,2-distearoyl-sn-glycero-3-phosphocholines (DSPC) and mixtures thereof. Phosphatidylcholines may be used alone or in combination with other lipids.

In various embodiments, the phosphatidylcholines can each comprise at least one unsaturated fatty acid moiety. For example, the phosphatidylcholines may each comprise L-α-phosphatidylcholine or 95% egg phosphatidylcholines (EPC). In some embodiments, the sphingolipids may each comprise at least one unsaturated fatty acid moiety. For example, the sphingolipids may each comprise hexadecanoylsphingomyelin or egg sphingomyelin.

In some embodiments, the liposomes include lipids derivatized with a hydrophilic polymer. In some embodiments, the hydrophilic polymer is a biocompatible polymer, particularly for injection into the body, such as intraocular administration. Suitable hydrophilic polymers include, among others, polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, hydroxymethylcellulose, hydroxyethylcellulose, hydroxypropylcellulose, polyethyleneglycol, polyaspartamide, poly-L-lysine, and hydrophilic peptide sequences.

In some embodiments, the lipid in the liposome is derivatized with polyethylene glycol. In some embodiments, the PEG chain has a molecular weight of about 300 to about 5,000 Daltons.

In some embodiments, the liposome is surface modified with poly-L-lysine. In some embodiments, the poly-L-lysine has a molecular weight of about 15,000-30,000 (see, e.g., Sasaki et al., 2013, Eur J Pharm Biopharm. 83(3):364-9; incorporated herein by reference).

Methods of preparing lipids derivatized with hydrophilic polymers are described in, for example U.S. Pat. Nos. 5,395,619; 5,556,948; 6,296,870; WO2014031429; all of which are incorporated herein by reference in their entireties).

In some embodiments, the liposome further comprises cholesterol or derivative thereof. In some embodiments, the cholesterol derivative can be cholestanol, dihydrocholesterol, cholesteryl esters, phytosterol, sitosterol, stigmasterol, campesterol, or mixtures thereof. In liposomes containing cholesterol or derivatives thereof, the amount can vary depending on the need or desired properties. In some embodiments, the content of cholesterol or cholesterol derivative in the liposome is about 0% to about 50% by weight of the liposome, about 0% to about 40% by weight of the liposome, about 0% to about 30% by weight of the liposome, about 0% to about 20% by weight of the liposome, about 0% to about 10% by weight of the liposome, about 10% to about 50% by weight of the liposome, about 10% to about 40% by weight of the liposome, about 10% to about 30% by weight of the liposome, about 10% to about 20% by weight of the liposome, about 20% to about 50% by weight of the liposome, about 20% to about 40% by weight of the liposome, about 20% to about 30% by weight of the liposome, or about 30% to about 40% by weight of the liposome. In some embodiments, the cholesterol content of the liposome is about 10% to about 40% by weight of the liposome.

In some embodiments, the liposome comprises a cationic lipid. In some embodiments, the liposome is a cationic liposome. In some embodiments, the cationic lipid is a linear $C_8$-$C_{20}$ alkyl or alkenyl amine. In some embodiments, "$C_8$-$C_{20}$ alkyl" refers to a straight chain hydrocarbon group having from 8 to 20 carbon atoms; "$C_8$-$C_{20}$ alkenyl" refers to a straight chain hydrocarbon group containing one or more double bonds and having from 8 to 20 carbon atoms. Linear $C_8$-$C_{20}$ alkyl or alkenyl amines include, without limitation, dodecyl amine, tallow amine, stearyl amine, cocoamine, octadecyl amine, N-octyloctan-1-amine, 2-nonenylamine, di(2-nonenyl)amine, and mixtures thereof. These linear $C_8$-$C_{20}$ alkyl or alkenyl amines may be used alone or in combination. In some embodiments, the linear $C_8$-$C_{20}$ alkyl or alkenyl amine is stearyl amine. For example, DPPC may be with and without added stearyl amine. In some embodiments, the cationic lipid is 1,2-di-O-octadecenyl-3-trimethylammoniumpropane (DOTMA), 1,2-dioleyloxy-N,N-dimethylaminopropane (DODMA), dioctadecyldi-methylammonium (DODA(Br)/DDAB), dioctadecyldimethylammoniumchloride (DODAC), 1,2-dimyristoyloxypropyl-1,3-dimethylhydroxyethylammonium (DMRIE), 2,3-dioleoyloxy-N-[2(spermine carboxamide)ethyl]-N,N-dimethyl-1-propanamium trifluoroacetate (DOSPA) analogues of these molecules having a different composition of the acyl chain moiety. In some embodiments, the cationic liposome includes one or more non-cationic lipid. In some embodiments, the non-cationic lipid is a neutral lipid, for example, cholesterol (Chol) or sphingomyelin (SM).

In some embodiments, the liposome comprises 1,2-dipalmitoyl-sn-glycero-3-phosphocholines (DPPC).

In some embodiments, the liposome comprises egg phosphatidylcholine (EPC) and 1-α-distearoyl phosphatidylcholine.

In some embodiments, the liposomes comprises egg phosphatidylcholine (EPC) or 1,2-dipalmitoyl-sn-glycero-3-phosphocholine), and cholesterol or a derivative thereof.

In some embodiments, the liposome comprises dioleoylphosphatidylcholine (DOPC), dioleoylphosphatidylglycerol (DOPG), and cholesterol or derivative thereof.

In some embodiments, the liposome comprises dipalmitoylphosphatidylcholine (DPPC), palmitoyl-oleoylphosphatidylcholine (POPC), and cholesterol.

In various embodiments, the liposomes can be prepared by various methods available in the art. In some embodiments, the liposomes can be prepared using lipids in aqueous solutions subjected to mechanical agitation, freeze drying, micro-emulsification, sonication, French pressure cells, membrane extrusions, or freeze thawing. In some embodiments, the liposome can be prepared by a solvent dispersion process, including ether injection, ethanol injection, or double emulsion. Methods for preparing liposomes are described in, among others, International patent publication WO 92/10166; Pat. Pub. US20080274172; U.S. Pat. Nos. 4,744,989; 5,395,619; 5,556,948; 5,549,910; 6,296,870; and 8,591,942.

In some embodiments, the loading of the liposomes with a drug compound is done by having the compound present during formation of the liposome, for example, to encapsulate the compound in the liposome. In some embodiments, the compound can be present in the lipid membrane, particularly hydrophobic compounds. In some embodiments, the compound can be incorporated into the liposome subsequent to liposome formation.

In some embodiments, the pharmaceutical composition comprising a compound of the disclosure in a liposome further comprises one or more excipients. In some embodiments, the excipient is one or more of a tonicity agent, viscosity enhancing agent, buffering agent, chelating agent, surfactant, preservative, and antioxidant. In some embodiments, the pharmaceutical liposome composition further comprises a tonicity agent. In some embodiments, the pharmaceutical liposome composition further comprises a buffering agent. In some embodiments, the pharmaceutical liposome composition further comprises a viscosity enhancing agent. In some embodiments, the pharmaceutical liposome composition further comprises a chelating agent. In some embodiments, the pharmaceutical liposome composition further comprises a surfactant. In some embodiments, the pharmaceutical liposome composition further comprises a preservative. In some embodiments, the pharmaceutical liposome composition further comprises an antioxidant. In some embodiments, the excipients are suitable for intraocular, e.g., intravitreal, administration.

In some embodiments, the liposome formulated with the compound further comprises at least a viscosity enhancing agent, as further describe herein. In some embodiments, the viscosity enhancing agent is hyaluronate or hyaluronic acid or a pharmaceutically acceptable salt thereof, as described herein.

In some embodiments, the liposome formulated with the compound is dispersed in a non-ionic surfactant poloxamer (e.g., Pluronic®). In some embodiments, the liposome is dispersed in a poloxamer selected from P124, P188, P237, P338, P407 and mixtures thereof. In some embodiments, the poloxamer is P188, P407, or mixtures thereof (see, e.g., Fattal et al., 2004, Int J Pharm. 277(1-2):25-30; incorporated herein by reference).

1.6. Biodegradable Microparticles and Nanoparticles

In another aspect, the compounds of the disclosure are formulated in microparticles or nanoparticles, particularly of bioerodible polymers. Various types of biocompatible bioerodible polymers can be used, including, but not limited to, poly(ester)s, poly(ester amide)s, poly(anhydride)s, poly(carbonate)s, poly(amino acid)s, poly(amide)s, poly(urethane)s, poly(ortho-ester)s, poly(iminocarbonate)s, and poly(phosphazene)s, by themselves or in combination. The polymers can be crosslinked or non-crosslinked. If crosslinked, the polymers can be less than 5% crosslinked, usually less than 1% crosslinked. In some embodiments, microparticle and nanoparticle compositions do not have free aldehyde groups capable of reacting with the compounds described herein.

In some embodiments, the biodegradable polymer comprises hydroxyaliphatic carboxylic acids, either homo- or copolymers, and/or polysaccharides. In some embodiments, the polymers are homo- or copolymers of D-lactic acid, L-lactic acid, racemic lactic acid, glycolic acid, caprolactone, and combinations thereof. In some embodiments, the polymers of the compositions include, among others, poly(lactide) (PLA), poly(lactide-co-glycolide) (PLGA), polyglycolide (PGA), polyhydroxybutyric acid, polycaprolactone (e.g., poly(8-caprolactone; PCL), polyvalerolactone, polyphosphazene, and polyorthoester. In some embodiments, the PLA can comprise poly D-lactic acid (PDLA) or poly L-lactic acid (PLLA).

In some embodiments, the pharmaceutical compositions comprise block copolymers of polyesters with polyethylene glycol (PEG). PLGA/PEG block copolymers have been processed as diblock (PLGA-PEG) or triblock molecules with both ABA (PLGA-PEG-PLGA) and BAB (PEG-PLGA-PEG) types. In diblock copolymers, PEG chains orient themselves towards the external aqueous phase in micelles, thus surrounding the encapsulated species. The layer of PEG acts as a barrier and reduces the interactions with other molecules by steric and hydrated repulsion for enhanced shelf stability. In triblock copolymers, ABA and BAB type polymers can act as a thermogel with an A-block covalently coupled with a B-block via ester linkage. The copolymer is usually a free-flowing solution at low temperature and can form a high viscosity gel at body temperature. These temperature-responsive copolymers, PLGA-PEG-PLGA or PEG-PLGA-PEG, are a type of block copolymers composed of hydrophobic PLGA segments and hydrophilic PEG segments. The hydrophobic PLGA segments form associative crosslinks and the hydrophilic PEG segments allow the copolymer molecules to stay in solution. At lower temperatures, hydrogen bonding between hydrophilic PEG segments and water molecules dominates the aqueous solution, resulting in their dissolution in water. As the temperature increases, the hydrogen bonding becomes weaker, while hydrophobic forces among the PLGA segments are strengthened, leading to solution-gel transition.

In some embodiments, the polymers are copolymers of glycolic and lactic acid (e.g., PLGA). In some embodiments, biodegradable polymer matrices include mixtures of hydrophilic and hydrophobic ended PLGA, which are useful in modulating polymer matrix degradation rates. Hydrophobic ended, also referred to as capped or end-capped, PLGA has an ester linkage hydrophobic in nature at the polymer terminus. Typical hydrophobic end groups include, but are not limited to, alkyl esters and aromatic esters. Hydrophilic ended, also referred to as uncapped, PLGA has an end group hydrophilic in nature at the polymer terminus. PLGA with a hydrophilic end group at the polymer terminus typically degrades faster than hydrophobic ended PLGA because it takes up water and undergoes hydrolysis at a faster rate (see, e.g., Tracy et al., 1999, Biomaterials 20:1057-1062, incorporated herein by reference). Examples of suitable hydrophilic end groups that may be incorporated to enhance hydrolysis include, but are not limited to, carboxyl, hydroxyl, and polyethylene glycol.

In some embodiments, the percent of each monomer in poly(lactic-co-glycolic)acid (PLGA) copolymer may be 0-100%, about 15-85%, about 25-75%, or about 35-65%. In some embodiments, the PLGA polymers can have a ratio of lactide to glycolide of about 10:90, 15:85, 20:80, 25:75, 30:70; 35:65, 40:60, 45:55, 50/50, 60:40; 65:35; 70:30 75:25 or 80:20. In some embodiments, the glycolic acid percentage in the polymer is used to adjust the rate of degradation. An increase in glycolic acid percentages generally increases the weight loss of the polymer. For example, PLGA 50:50 (PLA/PGA) exhibits a faster degradation than PLGA 65:35 due to preferential degradation of glycolic acid proportion assigned by higher hydrophilicity. PLGA 65:35 shows faster degradation than PLGA 75:25 and PLGA 75:25 than PLGA 85:15. The glycolic acid content also affects hydrophilicity of the matrix and thus the degradation and drug release rate.

In some embodiments, the microparticles or nanoparticles comprise a poly(ester amide)s ("PEAs") (see, e.g., Andres-Guerrero et al., 2015, J Controlled Release 211, 10:105-117, incorporated herein by reference). PEAs are synthetic polycondensation products comprised of biocompatible building blocks such as hydrophobic L-amino acids, aliphatic di-carboxylic acids and $\alpha,\omega$ diols (see, e.g., patent publication US20170119813A1; Tsitlanadze, et al., 2004, J. Biomater. Sci. Polym. Edn. 15:1-24; U.S. Pat. No. 9,873,764; and Rodriguez-Galin et al., Biodegradable Poly (Ester Amide)s: Synthesis and Applications," In Biodegradable Polymer: Processing and Degradation, G. Felton ed., Chapter 4, pages 207-272, Nova Science Publishers (2011); all publications incorporated herein by reference in their entireties). In some embodiments, the PEA comprises an $\alpha$-amino acid (e.g., glycine, 4-amino butyric acid, L-alanine, L-phenylalanine, etc.). In some embodiments, the PEA comprises L-alanine. In some embodiments, the $\alpha$-amino acid content is about 100%, about 90%, about 80%, about 70%, about 50%, or about 30%.

In some embodiments, the PEA comprises a copolymer of $\alpha$-hydroxy acid and $\alpha$-amino acid. In some embodiments, the PEA comprises poly[(e-caprolactam)-co-(e-caprolactone). In some embodiments, the PEA is a random aliphatic poly(ester amide)s (e.g., based on adipic acid, 6-aminohexanoic acid, and 1,4-butanediol).

In some embodiments, the weight average molecular weight (MW) of the polymers, including copolymers, can be in the range of about 10,000 to about 400,000, or in the range of about 60,000 to about 250,000 Daltons. In some embodiments, the weight average molecular weight (MW) of the polymers is about 8000 to about 14000 Daltons; molecular weight of about 13000 to about 16000 Daltons. Polymers with higher molecular weight, which have longer polymer chains, are used to decrease degradation rates. However this can be opposite for PLLA due to an inversely proportional degree of crystallinity with the molecular weight.

In some embodiments, the pharmaceutical composition is a microsphere, microcapsule, or microparticle. In some embodiments, the microparticles have an average particle size of about 1 to about 250 um, about 1 to about 200 µm; about 1 to about 150 µm; about 1 to about 100 µm; about 1 to about 50 µm; about 1 to about 40 µm; about 1 to about 30 µm; about 1 to about 20 µm; about 1 to about 10 µm; or about 1 to about 5 um.

In some embodiments, the bioerodible pharmaceutical compositions are in the form of a nanoparticle. In some embodiments, the nanoparticles have an average size of about less than about 1 um (sub-micron). In some embodiments, the nanoparticles have an average size of less than about 900 nm, less than about 800 nm, less than about 700 nm, less than about 600 nm, less than about 500 nm, less than about 400 nm, less than about 300 nm, less than about 200 nm, or less than about 100 nm. In some embodiments, the average particle size of the nanoparticle is from about 100 to about 200 nm; about 200 to about 300 nm; about 300 to about 400 nm; or about 400 to about 500 nm. In some embodiments, the average particle size of the nanoparticle is from about 50 to about 900 nm, about 50 to about 800 nm, about 50 to about 700 nm, about 50 to about 600 nm, about 50 to about 500 nm, about 50 to about 400 nm, about 50 to about 300 nm, about 50 to about 200 nm, or about 50 to about 100 nm. In some embodiments, the average particle size is from about 50 to about 500 nm. In other embodiments, the average particle size is from about 50 to about 400 nm. In further embodiments, the average particle size is from about 50 to about 300 nm. In further embodiments, the average particle size is about 50 to about 200 nm. In further embodiments, the average particle size is about 50 to about 100 nm. In further embodiments, the average particle size is about 50 to about 75 nm. In some embodiments, the average particle size is from about 50 to about 60 nm.

In some embodiments of the nanoparticles containing PLGA, the PLGA has an average molecular weight of from about 2,000 to about 10,000 Daltons. In other embodiments, the PLGA has an average molecular weight of from 2,000 to about 7,000 Daltons. In other embodiments, the PLGA has an average molecular weight of from about 2,000 to about 5,000 Daltons. In some embodiments, the PLGA has an average molecular weight of from about 4,000 to about 20,000 Daltons, or from about 4,000 to about 10,000 Daltons, or from about 4,000 to about 5,000 Daltons. In still other embodiments, the PLGA has an average molecular weight of about 2,000, about 4,500, about 5,000, about 7,000, or about 10,000 Daltons.

In some embodiments, the microparticles or nanoparticles can have an associated non-active agent. In some embodiments, the non-active agent is one or more of polyethylene glycols (PEG), fatty acids, amino acids, aliphatic or non-aliphatic molecules, aliphatic thiols, aliphatic amines, and the like. In some embodiments, the non-active agent is a PEG of differing chain lengths. In some embodiments, the non-active agent is a stabilizer, such as polyvinyl alcohol (PVA).

In some embodiments, the pharmaceutical composition is a biocompatible, injectable intraocular drug delivery system comprising (a) a plurality of microparticles with an average diameter of about 8 um to about 14 um, and (b) an aqueous vehicle for the microspheres, wherein the microspheres comprise: (1) a compound disclosed herein, wherein the compound comprises from about 0.1 wt % to about 10 wt % of the microparticles, and; (2) one or more biodegradable polymers comprising PLA polymers or PLGA polymers with a viscosity of between about 0.4 dL/gm and about 0.8 dL/gm, wherein the PLA polymer or PLGA polymer comprises from about 85 wt % to about 99.5 wt % of the microspheres, and; wherein the drug delivery system can be injected into an intraocular location through a 19 to 26 gauge syringe needle.

In some embodiments, the microparticles and nanoparticles can be prepared by various methods, such as oil/water emulsion, solvent/oil/water emulsion, oil/oil emulsion, and spray drying. Methods are described in, for example, Wischke and Schwendeman, 2008, "Principles of encapsulating hydrophobic compounds in PLA/PLGA microparticles," Intl J Pharmaceutics 364:298-327; and patent publication US20160143851A1; incorporated herein by reference. In some embodiments, the microparticles are prepared by an oil in water emulsion process by dissolving the polymer (e.g., PLGA) in a water immiscible, volatile organic solvent (such as dichloromethane (DCM), tetrahydrofuran (THF) or ethyl acetate) and then dissolving the compound, sometimes prepared as particles (e.g., 20-30 um) in the prepared solution or alternatively dissolving the compound in a miscible co-solvent and mixing. Co-solvents are generally used for drugs that do not show a high solubility in the primary organic solvent. The resulting organic oil phase is then emulsified in an aqueous solution (continuous phase) containing an appropriate emulsifier, for example polyvinyl alcohol. The emulsifiers included in the aqueous phase can act as stabilizers for the oil-in-water emulsion. The emulsion is then subjected to solvent removal by either evaporation or extraction process to solidify the oil droplets. Generally, volatile solvents can be removed from such emulsions by evaporation to a gas phase or in any case by extraction to the continuous phase. For example, in the former case, the emulsion is maintained at reduced pressure or at atmospheric pressure and the stir rate is reduced while the temperature is increased to enable the volatile solvent to evaporate. In the latter case, the emulsion is transferred to a large quantity of water (with or without surfactant) or other quench medium, into which the solvent associated with the oil droplets is diffused out. Combination of solvent evaporation and extraction is also applicable. The solid microspheres so obtained are then washed and collected by sieving. These are then dried under appropriate conditions such as by vacuum drying or lyophilization.

In some embodiments, the microparticles are prepared by a solvent/oil/water emulsion, which can be used when the compound cannot be dissolved in a carrier solvent or solvent mixture or extensive drug loss to the continuous phase cannot be avoided when employing cosolvent systems. For the solvent/oil/water emulsion, the compound is dispersed in the oil phase of the organic solvent or mixture of solvents and the polymer dissolved into this phase. The s/o/w method generally uses a low drug particle size in order to allow a complete encapsulation of drug crystals.

In some embodiments, the microparticles are prepared by oil/oil emulsion. This method can be used for compounds that are classified as hydrophobic but exhibit some solubility in aqueous media. The compound to be encapsulated and the polymer are dissolved in an organic solvent (e.g., acetonitrile) and then the solution is emulsified into a continuous phase of a solution of an emulsifier (HLB typically <8) in oil, e.g., cottonseed oil or mineral oil. The first oil-phase solvent (e.g., acetonitrile) is extracted in the external oil phase, which can be a non-solvent for both the polymer and the drug. Alternative methods concern the s/o/o technique combining the concepts of s/o/w and o/o methodologies. The removal of the continuous phase can be done by washing the particles with hexane or petroleum ether. The emulsification process can be achieved by the mechanical stirring, high shear mixers and/or static mixers.

In some embodiments, the microspheres or microparticles can be prepared by spraying a solution or suspension of a compound in an organic solution of the polymer, for example a solid-in-oil dispersion or water-in-oil emulsion. Generally, spray drying is defined as the transformation of a feed from a fluid state (solution, or dispersion) into a dried particulate form by spraying the feed into a gaseous drying medium (e.g., hot air). In some embodiments, various spray drying systems can be used, which may be classified according to the nozzle design as rotary atomization, pressure atomization, and two-fluid atomization. In some embodiments, the spray drying process uses coaxial capillary flow technique to produce monodispersed micro/nanoparticles with either simple or core-shell structure.

For preparing nanoparticles, the techniques used in preparing microparticles can be used. Typically, adjustment of processing parameters allows production of nanoparticles. In some embodiments, the process uses a small dispersed phase ratio and rate of stirring. In some embodiments, nanoparticles are prepared by emulsification-solvent evaporation process, particularly for encapsulation of hydrophobic compounds. Double or multiple emulsion can be used for more hydrophilic compounds. Emulsification at high rate of stirring, e.g., high speed homogenizer, can be used to reduce the formed particle size.

In some embodiments, the nanoparticles are prepared by nanoprecipitation process. In some embodiments, polymer and compound are dissolved in an organic solvent (e.g., acetone) and added to an aqueous solution containing surfactant, such as Pluronic, particularly Pluronic F68. The organic solvent is evaporated at appropriate temperatures and reduced pressures leaving behind the polymer encapsulated nanoparticles with drug compound. Salting out is another method in which a water-in-oil emulsion is first formed containing polymer, solvent (usually non-chlorinated solvent, e.g., acetone), salt (e.g., magnesium acetate tetrahydrate) and stabilizer. Water is then added to the solution until the volume is sufficient to diffuse acetone into the water, resulting in nanoparticle formulations In some embodiments, the pharmaceutical composition of the compound in the form of microparticles or nanoparticles of biodegradable polymer further comprises one or more excipients selected from a tonicity agent, viscosity enhancing agent, buffering agent, chelating agent, surfactant, preservative, and antioxidant.

In some embodiments, the pharmaceutical composition of the compound in the form of microparticles or nanoparticles of a biodegradable polymer further comprises a tonicity agent. In some embodiments, the pharmaceutical composition of the compound in the form of microparticles or nanoparticles of a biodegradable polymer further comprises a buffering agent. In some embodiments, the pharmaceutical composition of the compound in the form of microparticles or nanoparticles of biodegradable polymer further comprises a viscosity enhancing agent. In some embodiments, the pharmaceutical composition of the compound in the form of microparticles or nanoparticles of a biodegradable polymer further comprises a chelating agent. In some embodiments, the pharmaceutical composition of the compound in the form of microparticles or nanoparticles of a biodegradable polymer further comprises a surfactant. In some embodiments, the pharmaceutical composition of the compound in the form of microparticles or nanoparticles of a biodegradable polymer further comprises a preservative. In some embodiments, the pharmaceutical composition of the compound in the form of microparticles or nanoparticles of biodegradable polymer further comprises an antioxidant. In some embodiments, the excipients are suitable for intraocular e.g., intravitreal administration.

1.7. Calcium Phosphate Particles

In some embodiments, the pharmaceutical compositions comprise the compound formulated as a calcium phosphate particle, particularly a calcium phosphate nanoparticle (see, e.g., patent publication WO2004050065A1; Chen et al., 2010, Pharm Soc Japan 130(3):419-24; U.S. Pat. No. 8,287,914; patent publication WO2008129562; patent publication EP2041025A2; all publications incorporated herein by reference). The low solubility of the hydroxyapatite (HA) type of calcium phosphate (CaP) in physiological conditions allows it to remain for extended periods after in vivo placement. In some embodiments, the calcium phosphate particles have an average particle size of about 200 nm to about 4000 nm. In some embodiments, the calcium phosphate particles have an average particle size of about 300 nm to about 4000 nm; about 300 nm to about 2000 nm; about 300 nm to about 1000 nm. In some embodiments, calcium phosphate particle compositions do not have free aldehyde groups capable of reacting with the compounds described herein.

In some embodiments, the calcium phosphate particles have an average particle size of less than 1000 nm (submicron size). In some embodiments, the calcium phosphate particles have an average particle size of about 200 to less than 1000 nm; about 200 to about 900 nm; about 200 to about 800 nm; about 200 to about 600 mm, or about 200 to about 400 nm. In some embodiments, the core particles of the nanoparticles have a morphology that is generally and substantially spherical in shape.

In some embodiments, the calcium phosphate nanoparticles can have varying stoichiometric amounts of $Ca^{2+}$ and $PO_4^{3-}$ ions. In some embodiments, the substitution of some ions of the crystallographic structure by ions such as P, $Na^+$, $K^+$, $Mg^{2+}$ and $CO_3^{2+}$ can provide different properties to the substituted calcium phosphates. In some embodiments, the calcium phosphates is hydroxyapatite (HA). Generally, the reabsorbing rate is proportional to the calcium phosphate solubility, which is also affected by the pH. Generally, CaP's can be ordered by their decreasing solubility as follows: dicalcium phosphate dihydrate (DCPD)>dicalcium phosphate anhydrous (DCPA)>amorphous calcium phosphate (ACP)>tetracalcium phosphate (TTCP)>α-tricalcium phosphate (α-TCP)>octacalcium phosphate (OCP)>tricalcium phosphate (β-TCP)>hydroxyapatite. In some embodiments, the calcium phosphate particle comprises dicalcium phosphate dihydrate (DCPD), dicalcium phosphate anhydrous, amorphous calcium phosphate (ACP), tetracalcium phosphate (TTCP), α-tricalcium phosphate (α-TCP), octacalcium phosphate (OCP), tricalcium phosphate (β-TCP), or hydroxyapatite. In some embodiments, the calcium phosphate particles comprise calcium phosphate, calcium hydroxyapatite, alpha tricalcium phosphate, beta tricalcium phosphate, calcium pyrophosphate, tetracalcium phosphate, or octacalcium phosphate. In some embodiments, the calcium phosphate particle comprises hydroxyapatite. In some embodiments, the calcium phosphate is β-tricalcium phosphate (β-TCP) that is a bioresorbable.

In some embodiments, the calcium phosphate particles can be prepared as a suspension in aqueous medium by reacting a soluble calcium salt with a soluble phosphate salt, and more particularly, by reacting calcium chloride with sodium phosphate under aseptic conditions. For example, an aqueous solution of calcium chloride having a concentration between about 5 mM and about 300 mM is combined by mixing with an aqueous solution of a suitable distilled water-based solution of sodium citrate, having a concentration between about 5 mM and about 300 mM. The presence of sodium citrate contributes to the formation of an electrostatic layer around the core particle, which helps to stabilize the attractive and repulsive forces between the core particles, resulting in physically stable calcium phosphate core particles. An aqueous solution of dibasic sodium phosphate having a concentration between about 5 mM and about 300 mM is then mixed with the calcium chloride/sodium citrate solution. The solution generally become turbid, indicating the formation of calcium phosphate core particles. In some embodiments, mixing is generally continued for at least about 48 hours, or until a suitable core particle size has been obtained, as determined by sampling the suspension and measuring the core particle size using known methods. The core particles may be optionally stored and allowed to equilibrate for a sufficient period of time, e.g., about seven days, at room temperature to achieve stability in size and pH prior to further use.

In some embodiments, the calcium phosphate particle has a calcium/phosphate molar ratio selected from a range of about 1 to 400, about 2 to 400, about 5 to 400, about 10 to 400, about 15 to 400, about 20 to 400, about 25 to 400, about 50 to 400, about 75 to 400, about 100 to 400, about 150 to 400, or about 200 to 400. In some embodiments, the calcium to phosphate molar ratio is about 2 to 350, about 5 to 300, about 10 to 250, about 15 to 200, about 20 to 150, about 25 to 100, or about 50 to 75. In some embodiments, the calcium phosphate particle has a calcium/phosphate molar ratio (Ca/P) of 1, 2, 5, 10. 15, 20, 25, 50, 75, 100, 150, 200, 250, 300, 350 or 400.

In some embodiments, the particles can be at least partially coated or impregnated or both with a pharmacologically active agent, wherein the pharmacologically active agent is disposed on the surface of the core particle and optionally held in place by a surface modifying agent sufficient to bind the agent to the core particle. In some embodiments, the surface modifying agents suitable for use in the particles include modified carbohydrates, carbohydrate derivatives, and other macromolecules with carbohydrate-like components characterized by the abundance of —OH side groups; polyethylene glycol (PEG); and modified PEG, such as PEG-inositol 1,3,4,5,6-pentakisphosphate (PEG-IP5). Surface modifying agents are described in, for example, U.S. Pat. Nos. 5,460,830; 5,462,751; 5,460,831; 5,219,577; Huang et al., 2017, ACS Appl. Mater. Interfaces 9 (12):10435-10445; the entire contents of each of which are incorporated herein by reference.

In some embodiments, the calcium phosphate particle is coated with a lipid (see, e.g., Huang et al., 2018, J Drug Targeting 26(5-6)). In some embodiments, the lipid is one or more of phosphatidylcholines, phosphatidylethanolamines, phosphatidic acids, gangliosides, glycolipids, phosphatidylglycerols, and cholesterol. In some embodiments, the phosphatidylcholine is L-α-phosphatidylcholine, egg phosphatidylcholines (EPC), 1,2-dioleoyl-sn-glycero-3-phosphocholines (DOPC), 1,2-dioleoyl-sn-glycero-O-ethyl-3-phosphocholines, 1,2-dilauroyl-sn-glycero-3-phosphocholines (DLPC), 1,2-dimyristoyl-sn-glycero-3-phosphocholines (DMPC), 1,2-dipalmitoyl-sn-glycero-3-phosphocholines (DPPC), 1,2-distearoyl-sn-glycero-3-phosphocholines (DSPC) and mixtures thereof.

In some embodiments, the lipid coating on the calcium phosphate particle is 1,2 dioleoyl-3-trimethylammonium propane (DOTAP) and cholesterol. In some embodiments, the lipid coating on the calcium phosphate particle is soy lecithin and cholesterol.

Coating of the core particles with a pharmacologically active agent can be carried out by suspending the core particles in a solution containing a dispersed surface modifying agent, for example a solution of water containing from about 0.1 to about 30 wt % of the surface modifying agent. The cores are maintained in the surface modifying agent solution for a suitable period of time, generally about one hour, and may be agitated, e.g., by rocking or sonication. The coated core particles can be separated from the suspension, including from any unbound surface modifying agent, by centrifugation. The coated core particles can then be resuspended in a solution containing the pharmacologically active agent to be adhered to the at least partially coated core particle. Optionally, a second layer of surface modifying agent may also be applied to the pharmacologically active agent adhered to the particle.

In some embodiments, the pharmaceutical composition comprising a compound of the disclosure formulated as calcium phosphate nanoparticles further comprises one or more suitable excipients. In some embodiments, the excipient is one or more of a tonicity agent, buffering agent, viscosity enhancing agent, chelating agent, surfactant, preservative, and antioxidant.

In some embodiments, the calcium phosphate nanoparticle compositions further comprise a tonicity agent. In some embodiments, the calcium phosphate nanoparticle compositions further comprise a buffering agent. In some embodiments, the pharmaceutical calcium phosphate nanoparticle compositions further comprise a viscosity enhancing agent. In some embodiments, the pharmaceutical calcium phosphate nanoparticle compositions further comprise a chelating agent. In some embodiments, the pharmaceutical calcium phosphate nanoparticle compositions further comprise a surfactant. In some embodiments, the pharmaceutical calcium phosphate nanoparticle compositions further comprise a preservative. In some embodiments, the pharmaceutical calcium phosphate particle compositions further comprise an antioxidant. In some embodiments, the excipients are suitable for intraocular, e.g., intravitreal, administration.

1.8. Complexing Agents

In some embodiments, the compounds of the disclosure are prepared as pharmaceutical composition comprising a complexing agent. A complexing agent is capable of complexing with one or more endogenous components of the tissue or tissue fluids, such as the vitreous, for forming a mass of enhanced viscosity. The complexing can occur through ionic interaction between the complexing agent and one or more components of the tissue, although other interaction (e.g., chemical reaction) may alternatively or additionally form the complex. In some embodiments, the complexing agent is cationically (i.e., positively) charged such that it can form an ionic complex with endogenous hyaluronic acid, collagen or both in the tissue or tissue fluid to form the mass of enhanced viscosity. In some embodiments, the complexing agent can be a positively charged polymer. In some embodiments, the complex formed between the complexing agent and the endogenous tissue component (e.g., hyaluronic acid) and the mass of enhanced viscosity formed thereby be bioerodible within the tissue to aid in the gradual breakdown of the mass and/or complex after formation thereof. In some embodiments, pharmaceutical compositions of a complexing agent do not have free aldehyde groups capable of reacting with the compounds described herein.

In some embodiments, the complexing agent is, by way of example and not limitation, polyamino acid, galactomannan (e.g., cationic-derivatized), cellulosic polymers, amine compounds, quaternary ammonium compounds or any combinations thereof. In some embodiments, the complexing agents can be provided in a polymeric and/or positively charged form. The complexing agent can be present in the composition in an amount that is at least 0.01 w/v %, at least 0.1 w/v %, or at least 0.5 w/v %. In some embodiments, the concentration of complexing agent will also typically be no greater than about 10 is w/v %, more typically no greater than about 3 w/v % and even possibly no greater than 1.0 w/v %.

In some embodiments, the complexing agent is a polyamino acid formed of multiple repeat units of an amino acid. Exemplary poly-amino acid complexing agents include, without limitation, polylysine, polyarginine, polyhistidine, or the like. In some embodiments, the polyamino acid, when used, is typically present in the composition at a concentration of at least 0.05% w/v, at least 0.2% w/v, at least 0.7% w/v, or at least 1% w/v. In some embodiments, the polyamino acid is at a concentration that is generally less than 10% w/v, at less than 5.0% w/v, or less than 1.4% w/v. Exemplary polylysines include poly-L-lysine, poly-D-lysine, racemic poly-DL-lysine, derivatives thereof and combinations thereof. In some embodiments, any of alpha polylysines, epsilon polylysines, poly-L-lysines, poly-D-lysines, any derivatives thereof, any combinations thereof or the like may be used for the pharmaceutical compositions. In some embodiments, the complexing agent is poly-c-L-lysine. In some embodiments, the lysine of the composition may be entirely or substantially entirely poly-c-L-lysine. The term substantially entirely, as it refers to poly-c-L-lysine means at least 70% by weight and more preferably at least 90% by weight of the lysine of the composition is poly-c-L-lysine.

In some embodiments, the polylysine in the composition has an average molecular weight that is at least 50,000 Daltons, more typically at least 150,000 Daltons or at least 300,000 Daltons. In some embodiments, the average molecular weight of the polylysine is from about 50,000 to about 500,000 Daltons; about 50,000 to about 400,000 Daltons; or about 50,000 to about 300,000 Daltons In some embodiments, the complexing agent is a positively charged amine compound, particularly positively charged amine polymers. The amine polymers can be primary, secondary, tertiary amines or a combination thereof. Such amine compounds or amine polymers can include or be derived from aromatic or zo heterocyclic base groups such as aniline, pyridine or others. Nucleosides and polymers derived therefrom are one particularly preferred class of amine compounds suitable as complexing agents for the composition of the present invention. Polysaccharides containing amine groups are also preferred for the composition of the present invention. Examples of amine containing polysaccharides include chitosan and water-soluble derivatives of chitosan.

In some embodiments, the complexing agent is a derivative of natural polymers, which has been modified to be positively charged and/or soluble in water. Cellulosic polymers are preferred within this class. In some embodiments, the complexing agent comprises a positively charged cellulosic polymer. In some embodiments, the cellulosic polymer comprises a copolymer of polyethoxylated cellulose or dimethyldiallyl ammonium chloride. In some embodiments, the polymers comprise CELQUAT SC-230M® and CELQUAT SC-240C® (Akzo-Nobel). Advantageously, these polymers can be modified to include varying amounts of nitrogen (i.e., nitrogen substitutions) and, through the use of greater or lesser substitutions, the degree of complexing can respectively be raised or lowered. When included, the positively charged natural (e.g., cellulosic) polymers are typically present in the composition at a concentration that is at least 0.01 w/v %, more typically at least 0.05 w/v % and even more typically at least 0.2 w/v % and a concentration that is typically less than 4.0 w/v %, more typically less than 1.0 w/v % and even more typically less than 0.4 w/v %.

In some embodiments, the complexing agent is a quaternary ammonium compound. A variety of quaternary copolymers of varying quaternization can be synthesized based on homo or copolymers of amino acrylates with methyl, ethyl or propyl side chains. These monomers could also be copolymerized with other nonionic monomers including quaternary acrylic homopolymers such as homopolymers of 2-methacryloxyethyl trimethylammonium chloride and 2-methacryloxyethyl methyl diethyl ammonium bromide and copolymers of quaternary acrylate monomers with water soluble monomers. When included, the quaternary ammonium compounds can be present in the composition at a concentration of at least about 0.01 w/v %, more typically at least 0.05 w/v %, and even more typically at least 0.2 w/v %, and a concentration that is typically less than 4.0 w/v %, more typically less than 1.0 w/v % and even more typically less than 0.4 w/v 0.

A useful polymer complexing agent is a polymeric quaternary ammonium salt of hydroxyethylcellulose and a trimethyl ammonium chloride substituted epoxide. This complexing agent is both a quaternary ammonium compound and a cellulosic polymer and has the CTFA designation polyquaternium-10. A suitable polymer is sold under the tradename UCARE JR-30M, which is commercially available from Rhodia or CELQUAT L-200 and H-100 (Akzo Nobel). In some embodiments, a suitable quaternary ammonium/cellulosic agent is an alkyl modified quaternary ammonium salt of hydroxyethyl cellulose and a trimethyl ammonium chloride substituted epoxide having the CTFA designation polyquaternium-24. An example of such polymer is sold under the tradename QUATRISOFT LM-200 and is commercially available from Amerchol Corp., Edison, N.J. Other useful polymer complexing agents, which are both quaternary ammonium compounds and cellulosic polymers, include various quaternary ammonium salts of hydroxyethyl cellulose sold under the tradename SOFTCAT and commercially available from The Dow Chemical Company, Midland, Mich.

In some embodiments, the complexing agent is a galactomannan polymer, for example cationic-derivatized galactomannan polymer, which can also typically be considered a cellulosic polymer. A useful polymer is positively charged guar. Guar (e.g., guar gum) or other galactomannan polymer substituted with positively charged chemical moieties can be used. In some embodiments, the galactomannan polymer can have a cationic degree of substitution (DS) with a lower limit of 0.01% and an upper limit of 3.0%, preferably a lower limit of 0.1% or 0.3% and an upper limit of 2.5%. The galactomannan, particularly in the case of guar gum, typically has a number weight average molecular weight (MW) with a lower limit of 50,000 and an upper limit of about 1,000,000, more preferably a lower limit of 100, 000 or 300,000 and an upper limit of about 700,000. An exemplary galactomannan is a positively charged guar gum such as 0-[2-hydroxy-3-(trimethylamonium) propyl] chloride guar, which is commercially available under the tradename C261N from Cosmedia. In some embodiments, the galactomannan polymer (e.g., guar gum) compounds exhibit low toxicity. In some embodiments, the galactomannan polymer is typically present in the composition at a concentration that is at least 0.04 w/v %, more typically at least 0.20 w/v % and even more typically at least 0.5 w/v % and a concentration that is typically less than 7.0 w/v %, more typically less than 3.0 w/v % and even more typically less than 1.2 w/v %.

In some embodiments, the pharmaceutical composition comprising the compound of interest and the complexing agent is formulated as a solution or a suspension. In some embodiments, the pharmaceutical composition is aqueous and comprises at least 50% and more typically at least 95% water.

In some embodiments, for intraocular or intravitreal injection, the composition prepared with the complexing agent consist essentially of or substantially of only complexing agent, therapeutic compound and water. As used herein, substantially only complexing agent, therapeutic agent and water means that the composition includes less than 5.0 w/v %, more typically less than 4.0 w/v % and even more preferably less than 2.0 w/v % of any ingredients other than complexing agent, therapeutic agent and water.

In some embodiments, the pharmaceutical composition of the compound and a complexing agent further comprises one or more excipients selected from a tonicity agent, viscosity enhancing agent, buffering agent, chelating agent, surfactant, preservative, and antioxidant.

In some embodiments, a suspending agent may be employed. In some embodiments, the suspending agent is, without limitation, a polysaccharide, e.g., xanthan gum, carboxymethylcellulose, chondroitin sulfate, or carboxyvinyl polymer.

1.9. Cyclodextrin Compositions

In some embodiments, the compounds of the disclosure are formulated as a pharmaceutical composition with a cyclodextrin. Formulations of an aldehyde trapping compound and cyclodextrin are disclosed in U.S. Pat. No. 9,814,701, incorporated herein by reference. In some embodiments, the pharmaceutical composition comprises a compound of the present disclosure, a cyclodextrin, and one or more excipients. In some embodiments, the excipients are suitable for intraocular, e.g., intravitreal administration.

In some embodiments, the cyclodextrin for use in the methods and compositions is selected from α-cyclodextrin, β-cyclodextrin, γ-cyclodextrin, derivatives thereof, and combinations thereof. In particular, the cyclodextrin for use in the methods is selected from β-cyclodextrin, γ-cyclodextrin, derivatives thereof, and combinations thereof.

In some embodiments, the cyclodextrin or derivative thereof is selected from carboxyalkyl cyclodextrin, hydroxyalkyl cyclodextrin, sulfoalkylether cyclodextrin, and alkyl cyclodextrin. In various embodiments, the alkyl group in the cyclodextrin is methyl, ethyl, propyl, butyl, pentyl, or hexyl.

In some embodiments, the cyclodextrin is α-cyclodextrin or a derivative thereof. In some embodiments, the α-cyclodextrin or a derivative thereof is selected from carboxyalkyl-α-cyclodextrin, hydroxyalkyl-α-cyclodextrin, sulfoalkylether-α-cyclodextrin, alkyl-α-cyclodextrin, and combinations thereof. In some embodiments, the alkyl group in the α-cyclodextrin derivative is methyl, ethyl, propyl, butyl, pentyl or hexyl.

In some embodiments, the cyclodextrin is β-cyclodextrin or a derivative thereof. In some embodiments, the α-cyclodextrin or derivative thereof is selected from carboxyalkyl-β-cyclodextrin, hydroxyalkyl-β-cyclodextrin, sulfoalkylether-β-cyclodextrin, alkyl-β-cyclodextrin, and combinations thereof. In some embodiments, the alkyl group in the β-cyclodextrin derivative is methyl, ethyl, propyl, butyl, pentyl or hexyl.

In some embodiments, the β-cyclodextrin or a derivative thereof is hydroxyalkyl-β-cyclodextrin or sulfoalkylether-β-cyclodextrin. In some embodiments, the hydroxyalkyl-β-cyclodextrin is hydroxypropyl-β-cyclodextrin. In some embodiments, the sulfoalkylether-β-cyclodextrin is sulfobutylether-β-cyclodextrin. In some embodiments, β-cyclodextrin or a derivative thereof is alkyl-β-cyclodextrin, in particular methyl-β-cyclodextrin. In some embodiments using methyl-β-cyclodextrin, the β-cyclodextrin is randomly methylated β-cyclodextrin.

In some embodiments, the cyclodextrin is γ-cyclodextrin or a derivative thereof. In some embodiments, the γ-cyclodextrin or derivative thereof is selected from carboxyalkyl-γ-cyclodextrin, hydroxyalkyl-γ-cyclodextrin, sulfoalkylether-γ-cyclodextrin, and alkyl-γ-cyclodextrin. In some embodiments, the alkyl group in the γ-cyclodextrin derivative is methyl, ethyl, propyl, butyl, pentyl, or hexyl. In some embodiments, the γ-cyclodextrin or derivative thereof is hydroxyalkyl-γ-cyclodextrin or sulfoalkylether-γ-cyclodextrin. In some embodiments, the hydroxyalkyl-γ-cyclodextrin is hydroxypropyl-γ-cyclodextrin, such as 2-hydroxypropyl-γ-cyclodextrin. In some embodiments, the γ-cyclodextrin or derivative thereof is S-2-carboxyalkyl-thio-γ-cyclodextrin, such as S-2-carboxyethyl-thio-γ-cyclodextrin.

In some embodiments, various salts of the cyclodextrin or salts of the cyclodextrin derivative can be used in the compositions and methods herein. In some embodiments, the salts are pharmaceutically acceptable salt(s), which refers to those salts of compounds, i.e., cyclodextrin, that are safe and effective for use in mammals and that possess the desired biological activity. Pharmaceutically acceptable salts include salts of acidic or basic groups present in the cyclodextrins. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, and p-toluenesulfonate salts. Suitable base salts include, but are not limited to, aluminum, calcium, lithium, magnesium, potassium, sodium, zinc, and diethanolamine salts. In some embodiments, the cyclodextrin is in the form of a sodium or potassium salt. Guidance on suitable pharmaceutically acceptable salts and their application to drug formulations can be found in various references, such as Remington's Pharmaceutical Sciences, 17th Ed., Mack Publishing Company, Easton, P A., 1985, and Berge, et al., 1977, "Pharmaceutical Salts," J Pharm Sci. 66:1-19, both of which are incorporated herein by reference.

In some embodiments, the cyclodextrin is a mixture of cyclodextrins. Such mixtures can be a combination of: α-cyclodextrin and β-cyclodextrin, including combinations of α-cyclodextrin and β-cyclodextrin derivatives; α-cyclodextrin and γ-cyclodextrin, including combinations of α-cyclodextrin and γ-cyclodextrin derivatives; β-cyclodextrin and γ-cyclodextrin, including combinations of β-cyclodextrin and γ-cyclodextrin derivatives; or combinations of α-cyclodextrin, β-cyclodextrin, and γ-cyclodextrin, including combinations of α-cyclodextrin, 3-cyclodextrin, and γ-cyclodextrin derivatives.

In some embodiments, the cyclodextrin (e.g., α-, β-, or γ-cyclodextrin), such as in a composition as described herein is present at about 0.1% to about 30% w/v, about 0.1% to about 25% w/v, about 0.1% to about 20% w/v, about 0.2% to about 15% w/v, about 0.5% to about 10% w/v, about 0.5% to about 7.5% w/v, or about 1% to about 5% w/v. For example, an exemplary cyclodextrin is sulfobutylether-β-cyclodextrin, which can be present at about 0.1% to about 30% w/v, about 0.1% to about 25% w/v, about 0.1% to about 20% w/v, about 0.2% to about 15% w/v, about 0.5% to about 10% w/v, about 0.5% to about 7.5% w/v, or about 1% to about 5% w/v. In some embodiments, an exemplary cyclodextrin is hydroxypropyl-β-cyclodextrin, which can be present at about 0.1% to about 30% w/v, about 0.1% to about 25% w/v, about 0.1% to about 20% w/v, about 0.2% to about 15% w/v, about 0.5% to about 10% w/v, about 0.5% to about 7.5% w/v, or about 1% to about 5% w/v. In some embodiments, an exemplary cyclodextrin is hydroxypropyl-γ-cyclodextrin, which can be present at about 0.1% to about 30% w/v, about 0.1% to about 25% w/v, about 0.1% to about 20% w/v, about 0.2% to about 15% w/v, about 0.5% to about 10% w/v, about 0.5% to about 7.5% w/v, or about 1% to about 5% w/v.

In embodiments where mixtures of cyclodextrins are used, for example mixtures of sulfobutylether-β-cyclodextrin and hydroxypropyl-β-cyclodextrin, the total amount of cyclodextrin can be present at about 0.1% to about 30% w/v, about 0.1% to about 25% w/v, about 0.1% to about 20% w/v, about 0.2% to about 15% w/v, about 0.5% to about 10% w/v, about 0.5% to about 7.5% w/v, or about 1% to about 5% w/v.

In some embodiments, the cyclodextrin, such as in a composition thereof, in particular an ophthalmic solution, for use in the methods herein is present at about 0.1% w/v, about 0.2% w/v, about 0.5% w/v, about 1% w/v, about 2% w/v, about 30% w/v, about 4% w/v, about 50% w/v, about 6% w/v, about 7% w/v, about 8% w/v, about 9% w/v, about 10% w/v, about 11% w/v, about 12% w/v, about 13% w/v, about 14% w/v, about 15% w/v, about 16% w/v, about 18% w/v, about 20% w/v, about 25% w/v, or about 30% w/v. For example, a β-cyclodextrin, e.g., sulfobutylether-β-cyclodextrin, can be present at about 0.1% w/v, about 0.2% w/v, about 0.5% w/v, about 1% w/v, about 2% w/v, about 3% w/v, about 4% w/v, about 5% w/v, about 6% w/v, about 7% w/v, about 8% w/v, about 9% w/v, about 10% w/v, about 11% w/v, about 12% w/v, about 13% w/v, about 14% w/v, about 15% w/v, about 16% w/v, about 18% w/v, about 20% w/v, about 25% w/v, or about 30% w/v. In some embodiments, a β-cyclodextrin, e.g., hydroxypropyl-β-cyclodextrin, can be present at about 0.1% w/v, about 0.2% w/v, about 0.5% w/v, about 1% w/v, about 2% w/v, about 3% w/v, about 4% w/v, about 5% w/v, about 6% w/v, about 7% w/v, about 8% w/v, about 9% w/v, about 10% w/v, about 11% w/v, about 12% w/v, about 13% w/v, about 14% w/v, about 15% w/v, about 16% w/v, about 18% w/v, about 20% w/v, about 25% w/v, or about 30% w/v. In some embodiments, a γ-cyclodextrin, e.g., hydroxypropyl-γ-cyclodextrin, can be present at about 0.1% w/v, about 0.2% w/v, about 0.5% w/v, about 1% w/v, about 2% w/v, about 3% w/v, about 4% w/v, about 5% w/v, about 6% w/v, about 7% w/v, about 8% w/v, about 9% w/v, about 10% w/v, about 11% w/v, about 12% w/v, about 13% w/v, about 14% w/v, about 15% w/v, about 16% w/v, about 18% w/v, about 20% w/v, about 25% w/v, or about 30% w/v.

In some embodiments where mixtures of cyclodextrins are used, for example mixtures ofسulfobutylether-β-cyclodextrin and hydroxypropyl-β-cyclodextrin, the total amount of cyclodextrin can be present at about 0.1% w/v, about 0.2% w/v, about 0.5% w/v, about 1% w/v, about 2% w/v, about 3% w/v, about 4% w/v, about 5% w/v, about 6% w/v, about 7% w/v, about 8% w/v, about 9% w/v, about 10% w/v, about 11% w/v, about 12% w/v, about 13% w/v, about 14% w/v, about 15% w/v, about 16% w/v, about 18% w/v, about 20% w/v, about 25% w/v, or about 30% w/v.

It is to be understood that while the cyclodextrin levels (e.g., concentration) for administration are given for exemplary cyclodextrins sulfobutylether-β-cyclodextrin, hydroxypropyl-β-cyclodextrin, and hydroxypropyl-γ-cyclodextrin, equivalent concentrations of the other specific cyclodextrins can be readily determined by the person of skill in the art.

In various embodiments containing the compounds formulated with a cyclodextrin, the compositions comprise one or more excipients. In some embodiments, the excipients are one or more of a tonicity agent, buffering agent, viscosity enhancing agent, chelating agent, surfactant, preservative, and antioxidant. In some embodiments, the cyclodextrin composition includes a tonicity agent. In some embodiments, the cyclodextrin composition includes a buffering agent. In some embodiments, the cyclodextrin composition includes a viscosity enhancing agent. In some embodiments, the cyclodextrin composition includes a chelating agent. In some embodiments, the cyclodextrin composition includes a surfactant. In some embodiments, the cyclodextrin composition includes an anti-oxidant. In some embodiments, the cyclodextrin composition includes a preservative.

In some embodiments, the composition of the compound and cyclodextrin containing one or more excipients are suitable for intraocular, e.g., intravitreal administration. In some embodiments, the composition of the compound and cyclodextrin containing one or more excipients are suitable for subcutanenous, intradermal, or intramuscular administration. In some embodiments, the composition of the compound and cyclodextrin containing one or more excipients are formulated to be suitable for intravenous administration.

In some embodiments, the pharmaceutical composition of the compound and cyclodextrin does not include carboxymethylcellulose. In some embodiments, the pharmaceutical composition of the compound and cyclodextrin does not include hydroxypropylcellulose. In some embodiments, where hydroxypropylmethylcellulose is present, the concentration is greater than 1% w/v.

1.10. Injectable Hydrogels

In some embodiments, the pharmaceutical composition comprises a compound of the disclosure and a hydrogel, in particular an injectable hydrogel. Generally, injectable hydrogels can undergo a "sol-gel" transition, where the transition is triggered by a change in environmental condition. In some embodiments, the condition for "sol-gel" transition include properties such as pH, temperature, ionic environment, glucose, or combinations thereof. Injectable hydrogels can be injected into a tissue, organ (e.g., eye) or a part of the body in the form of liquid and once administered undergo in situ gelation (see, e.g., US20160331738; WO2006122183A2; incorporate herein by reference). The compound of interest is incorporated and suspended in the hydrogel in the "sol" state. In some embodiments, hydrogel compositions do not have free aldehyde groups capable of reacting with the compounds described herein.

In some embodiments, the hydrogel is at concentrations in which the composition is liquid at conditions prior to administration, and forms a gel upon administration into the tissue, organ or body part. For example, at concentrations of 20% w/v and higher, aqueous solutions of Poloxamer F407, described below, remain as a liquid at low temperatures (<15° C.) and transitions to a viscous semisolid gel upon intraocular administration.

In some embodiments, the injectable hydrogels are comprised of polyethylene oxide; polypropylene oxide; polyoxyethylene-polyoxypropylene block copolymers (e.g., Poloxamer 407 and Poloxamer 188); acrylic polymers such as, but not limited to, polyacrylic acid (PAA) (e.g., carbomers, Carbopol® 974P, etc.); polyvinylpyrrolidones; polyethylene glycols (PEGs) (e.g., from Nektar); gelatin, polyvinyl alcohols (PVA); polyhydroxyethyl methacrylate (poly-HEMA or PHEMA); cellulose; alginate; chitin or combinations thereof.

In some embodiments, the hydrogel is a biodegradable hydrogel. A biodegradable hydrogel can incorporate a biodegradable linkage in the hydrogel and/or precursor may be water-degradable or enzymatically degradable. Exemplary water-degradable biodegradable linkages include polymers, copolymers and oligomers of glycolide, dl-lactide, 1-lactide, dioxanone, esters, carbonates, and trimethylene carbonate. Exemplary enzymatically biodegradable linkages include peptidic linkages cleavable by metalloproteinases and collagenases. Examples of biodegradable linkages include polymers and copolymers of poly(hydroxy acid)s, poly(orthocarbonate)s, poly(anhydride)s, poly(lactone)s, poly(amino acid)s, poly(carbonate)s, and poly(phosphonate)s. In some embodiments, the gel degrades in the physiological fluid in without causing inflammation by degrading into components that are biocompatible and not acidic. In some embodiments, the hydrogel adheres to the tissue.

In some embodiments, the hydrogel is a thermoresponsive hydrogel. In certain embodiments, the thermoresponsive hydrogel has a lower critical solution temperature (LCST) below body temperature. In some embodiments for therapeutic use, the thermoresponsive hydrogel remains fluid below physiological temperature (e.g., 37° C. for humans) or at or below room temperature (e.g., 25° C.) and forms into a hydrogel at the physiological temperature and is biocompatible. In some embodiments, the thermoresponsive hydrogel can be a liquid at a temperature below 34° C. which reversibly solidifies into a gelled composition at a temperature above 34° C. In some embodiments, the hydrogel composition is a solution at about 20° C. to 27° C. and is a gel at about 34° C. to 37° C.

Thermoresponsive hydrogel can be selected from naturally derived and synthetic polymers exhibiting this behavior. Natural polymers include elastin-like peptides and polysaccharides derivatives, while synthetic polymers include those comprised of poly(n-isopropyl acrylamide) (PNIPAAm), poly(N,N-dimethylacrylamide-co-N-phenylacrylamide), poly(glycidyl methacrylate-co-N-isopropylacrylamide), poly(ethylene oxide)-β-poly(propylene oxide)-β-poly(ethylene oxide), poly(ethylene glycol)-polyester copolymer, and amphiphilic block copolymers. In some embodiments, the amphiphilic block copolymer comprises a hydrophilic component selected from polyethylene oxide (PEO), polyvinyl alcohol (PVA), polyglycolic acid (PGA), poly(N-isopropylacrylamide), poly(acrylic acid) (PAA), polyvinyl pyrrolidone (PVP) or mixtures thereof, and a hydrophobic component selected from polypropylene oxide (PPO), poly(lactic acid) (PLA), poly(lactic acid co glycolic acid) (PLGA), poly(β-benzoyl L-aspartate) (PBLA), poly(γ-benzyl-L-glutamate) (PBLG), poly(aspartic acid), poly(L-lysine), poly(spermine), poly(caprolactone), or mixtures thereof. Exemplary amphiphilic block copolymers include (PEO)(PPO)(PEO) block copolymers (PEO/PPO), and poly(lactic acid co glycolic acid) block copolymers (PLGA), such as (PEO)(PLGA)(PEO) block copolymers.

In some embodiments, the hydrogel is comprised of polyacrylamide (e.g., poly-N-isopropylacrylamide), poly-ethylene oxide/polypropylene oxide, or combinations of the two (e.g., Pluronic® or Tectronic®), butyl methacrylate, polyethylene glycol diacrylate, polyethylene glycol of varying molecular weights, polyacrylic acid, poly-methacrylic acid, poly-lactic acid, poly(tetramethylene ether glycol), poly(N,N'-diethylaminoethyl methacrylate), methyl methacrylate, and N,N'-dimethylaminoethylmethacrylate.

In some embodiments, the hydrogel is selected from xyloglucan, gelatin, agarose, amylase, amylopectin, cellulose derivatives and gellan, exhibiting thermoreversible gelation behaviors. For example, a chitosan-based, injectable thermogels has been engineered through grafting an appropriate amount of PEG onto the chitosan backbone and used for prolonged drug release in vitro (see, e.g., U.S. Pat. Nos. 6,730,735; 8,663,686; incorporated herein by reference).

In some embodiments, the hydrogel is comprised of poly(ethylene oxide)-β-poly(propylene oxide)-β-poly(ethylene oxide), also known as poloxamer, Pluronics®, or Tetronics®. In some embodiments, the poloxamer is P124, P188, P237, P338, P407, or mixtures thereof (e.g., Pluronic®, e.g., L 44 NF, F 68 NF, F 87 NF, F 108 NF, and F 127 NF). In some embodiments, the hydrogel is comprised of P188, or P407, or mixtures thereof. In some embodiments, the hydrogel is a mixture of P188 and P407. In some embodiments, the poloxamer hydrogel can include an additional polymer, such as polyethylene glycol, PAA, methylcellulose, hydroxypropyl methylcellulose, carboxymethyl cellulose to achieve a phase transition temperature higher than room temperature (25° C.) and gelling at tissue, organ or body temperature (e.g., pre-corneal temperature 35° C.).

In some embodiments, the hydrogel is a pH sensitive hydrogel. In some embodiments, the hydrogel is selected from polymethyl methacrylate (PMMA), polyacrylamide (PAAm), polyacrylic acid (PAA), poly-dimethylaminoethylmethacrylate (PDEAEMA) and polyethylene glycol. These polymers are generally hydrophobic but swells in water depending upon the pH prevalent in the external environment. In some embodiments, the pH-sensitive hydrogel can be a copolymer of PMMA and polyhydroxyethyl methyl acrylate (PHEMA), which are anionic copolymers, swell high in neutral or high pH but do not swell in acidic medium.

In some embodiments, the hydrogel comprises a carbomer (e.g., Carbopol®), which is a cross-linked acrylic acid polymer (PAA) and shows pH induced phase transition as the pH is raised above its pKa of about 5.5. Carbomers are available as carbomer homopolymers, which are polymers of acrylic acid crosslinked with allyl sucrose or allyl pentaerythritol; carbomer copolymers, which are polymers of acrylic acid and $C_{10}$-$C_{30}$ alkyl acrylate crosslinked with allyl pentaerythritol; and carbomer interpolymers, which are carbomer homopolymer or copolymer that contains a block copolymer of polyethylene glycol and a long chain alkyl acid ester. In some embodiments, the carbomer is selected from Carbopol 71G NF, 971P NF, 974P NF, 980 NF, 981 NF, 5984 EP, and ETD 2020 NF, Ultrez 10 NF. In some embodiments, the hydrogel comprises a carbomer and a suitable viscosity enhancing agent, e.g. hydroxypropyl methylcellulose or methyl cellulose, in a sufficient amount to allow reduction in PAA concentration without comprising the in situ gelling properties. In some embodiments, the hydrogel is comprised of Carbopol® 940 and Methocel E50LV (HPMC).

In some embodiments, the hydrogels can include about 15% to about 30% by weight poloxamer, more particularly about 17.5% to about 25%, and even more particularly about 20% to about 25%. In some embodiments, the hydrogels can also include about 0.2% to about 4% by weight carbomer, more particularly about 0.5 to about 2.0%, and even more particularly about 0.7% to about 1.5%.

In some embodiments, the compound is deployed in the hydrogel. In some embodiments, the compound is formulated in a microparticle or nanoparticle, as described herein, and the microparticles and/or nanoparticles deployed in the hydrogel. In some embodiments, the compound of the disclosure is formulated in a liposome, as described herein, and the liposome deployed in the hydrogel. In some embodiments, the compound of the disclosure is formulated in a calcium phosphate particle, as described herein, and the calcium phosphate particle deployed in the hydrogel.

In some embodiments, the pharmaceutical composition of the compound formulated in a hydrogel further comprises one or more excipients selected from a tonicity agent, viscosity enhancing agent, buffering agent, chelating agent, surfactant, preservative, and antioxidant.

In some embodiments, the pharmaceutical composition of the compound formulated in a hydrogel further comprises a tonicity agent. In some embodiments, the pharmaceutical composition of the compound formulated in a hydrogel further comprises a viscosity enhancing agent. In some embodiments, the pharmaceutical composition of the compound formulated in a hydrogel further comprises a buffering agent. In some embodiments, the pharmaceutical composition of the compound formulated in a hydrogel further comprises a chelating agent. In some embodiments, the pharmaceutical composition of the compound formulated in a hydrogel further comprises a surfactant. In some embodiments, the pharmaceutical composition of the compound formulated in a hydrogel further comprises a preservative. In some embodiments, the pharmaceutical composition of the compound formulated in a hydrogel further comprises an antioxidant. In some embodiments, the hydrogel and excipients are suitable for intraocular, e.g., intravitreal administration.

1.11. Excipients

In some embodiments, the pharmaceutical compositions comprise one or more pharmaceutically acceptable additive or excipients suitable for injection, including subcutaneous, intradermal, intramuscular, intraperitoneal, intraocular, and in some embodiments, intravenous administration. In particular, the one or more excipients is suitable for intraocular, e.g., intravitreal administration. In some embodiments, the excipient is selected from a tonicity agent, buffering agent, viscosity enhancing agent, chelating agent, surfactant, preservative, and antioxidant.

1.11.1. Tonicity Agents

In some embodiments, the pharmaceutical compositions can have one or more tonicity agents, which can be used to adjust the tonicity of the composition suitable for the mode of administration. Suitable tonicity agents include, by way of example and not limitation, dextrans (e.g., dextran 40 or 70), dextrose, glycerin, propylene glycol, and salts, such as potassium or sodium salts. Equivalent amounts of one or more salts made up of cations, for example, such as potassium, ammonium and anions such as chloride, citrate, ascorbate, borate, phosphate, bicarbonate, sulfate, thiosulfate, bisulfate, the salts sodium bisulfate and ammonium sulfate, can also be used.

The amount of tonicity agent will vary, depending on the particular agent to be added. In general, however, the compositions can have a tonicity agent in an amount sufficient to cause the final composition to have a physiologically acceptable osmolarity, such as an ophthalmically acceptable osmolarity. In some embodiments, the cyclodextrin compositions have an osmolarity of about 200 to about 1000 mOsm/L or about 200 to about 500 mOsm/L, or any specific value within said ranges (e.g., 200 mOsm/L, 210 mOsm/L, 220 mOsm/L, 230 mOsm/L, 240 mOsm/L, 250 mOsm/L, 260 mOsm/L, 270 mOsm/L, 280 mOsm/L, 290 mOsm/L, 300 mOsm/L, 310 mOsm/L, 320 mOsm/L, 330 mOsm/L, 340 mOsm/L, 350 mOsm/L, 360 mOsm/L, 370 mOsm/L, 380 mOsm/L, 390 mOsm/L or 400 mOsm/L). In a particular embodiment, the ophthalmic formulations are adjusted with a tonicity agent to an osmolarity of ranging from about 250 to about 450 mOsm/L, or about 250 to about 350 mOsm/L.

1.11.2. Antioxidants

In some embodiments, the pharmaceutical compositions include an antioxidant tolerated by the subject or the tissue to be treated, for example intraocular tissues. In some embodiments, suitable antioxidant is glucose, ascorbate, sulfides, superoxide dismutase (SOD), cysteine and derivatives thereof. In some embodiments, the anti-oxidant is sodium bisulfite, sodium metabisulfite, ascorbate, sodium sulfite, or thioglycerol. In some embodiments, other antioxidants, tolerated by the intraocular tissues, known in literature, can be used, e.g. hydrosoluble antioxidants, antioxidants which have at least one —SH or —CHO group, peptides and enzymes.

In some embodiments, the antioxidant is glutathione, N-acetylcysteine, tocopherol, ascorbic acid, tetrahexyldecyl ascorbate, butylated hydroxytoluene (BHT), butylated hydroxyanisole, methylgentisate, L-carnosine, tert-butylhydroquinone (TBHQ), glutathione, including derivatives, combinations, and mixtures thereof. In some embodiments, the antioxidant can be at a concentration of 0.01% to 1% w/v, about 0.02% to 1% w/v; about 0.05% to 1% w/v; about 0.01 to 0.5% w/v; about 0.02% to 0.5% w/v; or about 0.05% to 0.5% w/v. In some embodiments, the pharmaceutical composition is free of antioxidants.

1.11.3. Buffering Agents

In some embodiments, the pharmaceutical composition can have one or more buffering agents for adjusting and/or maintaining the pH of the composition. In some embodiments, the one or more buffering agents is used to provide a pH range compatible with the tissue subjected to treatment or administration, for example subcutaneous or intraocular environment. Generally, buffer capacity should be large enough to maintain the product pH for a reasonably long shelf-life but also low enough to allow rapid readjustment of the product to physiologic pH upon administration. Generally, buffer capacities of from about 0.01 to 0.1 can be used, particularly at concentrations that provide sufficient buffering capacity and minimizes adverse effects, e.g., irritation to the tissue. Exemplary buffering agents include, by way of example and not limitation, various salts (e.g., sodium, potassium, etc.), acids or bases, where appropriate, of the following agents, including, among others, acetate, borate, phosphate, citrate, bicarbonate, carbonate, succinate, tartaric, lactic, tetraborate, biphosphate, tromethamine, hydroxyethyl morpholine, or THAM (trishydroxymethylamino-methane).

In some embodiments, the buffering agent can be present from about 0.01 mM to about 100 mM, about 0.05 mM to about 100 mM, about 0.5 mM to about 100 mM, from about 1 mM to about 50 mM, from about 1 mM to about 40 mM, from about 1 mM to about 30 mM, from about 1 mM to about 20 mM, or from about 1 mM to about 10 mM. In some embodiments, the buffering agent can be present at about 0.01 mM, about 0.05 mM, about 0.1 mM, about 0.2 mM, about 0.5 mM, about 1 mM, about 5 mM, about 10 mM, about 20 mM, about 30 mM, about 40 mM, about 50 mM, or about 100 mM.

1.11.4. Surfactants

In some embodiments, the pharmaceutical compositions include one or more suitable surfactants, particularly a non-ionic surfactant. In some embodiments, the surfactant is a non-ionic surfactant which is polyol esters, polyoxyethylene esters, poloxamers. polyol esters, such as glycol and glycerol esters and sorbitan derivatives. In some embodiments, the non-ionic surfactant is selected from polyoxyethylene (20) sorbitan monolaurate (Tween 20), polyoxyethylene (20) sorbitan monopalmitate (Tween 40), polyoxyethylene (20) sorbitan monostearate (Tween 60), polyoxyethylene (20) sorbitan mono-oleate (Tween 80), polyoxyethylene (20) sorbitan tristearate (Tween 65), polyoxyethylene (20) sorbitan tri-oleate (Tween 85), sorbitan monopalmitate (Span 40), sorbitan monostearate (Span 60), sorbitan mono-oleate (Span 80), sorbitan tristearate (Span 65), and sorbitan trioleate (Span 8).

In some embodiments, the surfactant is a poloxamer or poloxamine. In some embodiments, the poloxamer is P124, P188, P237, P338, P407 and mixtures thereof (see, e.g., Bermudez et al., 2011, Intl Res J Pharmacy Pharmacol. 1(6):109-118; Xuan et al., 2011, Drug Delivery 18(5):305-31; all publications incorporated herein by reference in their entireties). Poloxamers are also available under the tradename Pluronic®, e.g., L 44 NF, F 68 NF, F 87 NF, F 108 NF, and F 127 NF.

In some embodiments, the surfactant is selected from polyoxyethylene 15 hydroxystearate; polyoxyethylene alkyl ethers, polyoxyethylene stearates, and polyoxyethylene castor oil, e.g., Cremophor EL, ELP, and RH40. In some embodiments, the non-ionic surfactant is selected from Cremophor EL, Cremophor RH 40, Cremophor RH 60, d-α-tocopherol polyethylene glycol 1000 succinate, polysorbate 20, polysorbate 80, Solutol HS 15, sorbitan monooleate, poloxamer 407, Labrafil M-1944CS, Labrafil M-2125CS, Labrasol, Gellucire 44/14, Softigen 767, and mono- and di-fatty acid esters of PEG 300, 400, or 1750.

In some embodiments, the surfactant can be present at about 0.00001% to about 2% w/v; about 0.00005% to about 2% w/v; about 0.0001% to about 2% w/v; about 0.0005% to about 2% w/v; about 0.001% to about 2% w/v; about 0.005% to about 2% w/v; about 0.01% to about 2% w/v; about 0.02% to about 2% w/v; about 0.05% to about 2% w/v; 0.1% to about 2% w/v; about 0.15% to about 2% w/v; about 0.2% to about 2% w/v; about 0.5% to about 2% w/v; or about 1% to about 2% w/v. In some embodiments, the surfactant can be present at about 0.00001% to about 1.5% w/v; about 0.0001% to about 1% w/v; about 0.0005% to about 1% w/v; about 0.001% to about 1% w/v; about 0.005% to about 0.5% w/v; or about 0.01% to about 0.2% w/v.

1.11.5. Suspending Agent or Viscosity Enhancing Agent

In some embodiments, the pharmaceutical compositions for injection includes one or more suitable suspending or viscosity enhancing agents. The suspending agents can enhance the physical stability of the compositions, and the viscosity enhancing agents can increase the viscosity of the compositions. Suspending agents and viscosity enhancing agents may overlap. In some embodiments, the suspending agent or viscosity enhancing agent is compatible with the tissue of administration or tissue to be treated.

For example, the vitreous humor contained in the posterior chamber of the eye is viscous. Intravitreal injection of a fluid or suspension of substantially lower viscosity into the posterior segment could therefore result in the presence of two somewhat immiscible phases or layers within the eye, which in turn can lead to the "pooling" of the injected fluid or suspension at the bottom of the posterior chamber and uneven or inconsistent dosing to tissues of the posterior segment.

Suspension of therapeutic compounds in a formulation having a relatively high viscosity, such as one approximating that of the vitreous humor, can limit the uneven distribution of the therapeutic agent. Such viscous formulation comprises a viscosity-inducing component.

In some embodiments, the suspending or viscosity enhancing agent is selected from carbopol, polyvinyl alcohol (PVA), polyvinyl pyrrolidone (PVP), polyvinyl acetate, gelatin, xanthan, gum tragacanth, gum acacia, sodium alginate, and cellulosic derivatives. In some embodiments, cellulosic derivatives include hydroxypropyl methyl cellulose (HPMC), hydroxyethyl cellulose (HEC), and methyl cellulose. In some embodiments, the concentration of suspending or viscosity enhancing agent can be present from about 0.1% to about 2% w/v, about 0.5% to about 1% w/v, or any specific value within the ranges.

In some embodiments, the suspending or viscosity enhancing agent ranges from about 0.1% to about 1.0% w/v, or any specific value within said range (e.g., 0.1-0.2%, 0.2-0.3%, 0.3-0.4%, 0.4-0.5%, 0.5-0.6%, 0.6-0.7%, 0.7-0.8%, 0.8-0.9%, 0.9-1.0%; about 0.2%, about 0.21%, about 0.22%, about 0.23%, about 0.24%, about 0.25%, about 0.26%, about 0.27%, about 0.28%, about 0.29%, about 0.30%, about 0.70%, about 0.71%, about 0.72%, about 0.73%, about 0.74%, about 0.75%, about 0.76%, about 0.77%, about 0.78%, about 0.79%, about 0.80%, about 0.81%, about 0.82%, about 0.83%, about 0.84%, about 0.85%, about 0.86%, about 0.87%, about 0.88%, about 0.89%, or about 0.90%). Where the primary component of the pharmaceutical composition has also viscosity enhancing properties, the suspending agents or viscosity enhancing agents can be used to augment the properties of the pharmaceutical compositions. In some embodiments, the viscosity-inducing component is present in an amount in a range of about 0.5% or about 1.0% to about 5% or about 10% or about 20% (w/v) of the composition.

1.11.6. Preservatives

In some embodiments, the pharmaceutical compositions can have one or more suitable preservatives, for example, to extend shelf life or limit bacterial growth in the compositions during storage as well as when administered to a subject. Preservatives that can be used, include, among others, benzalkonium chloride, benzethonium chloride, benzododecinium bromide, cetylpyridinium chloride, chlorobutanol, ethylenediamine tetracetic acid (EDTA), thimerosol, phenylmercuric nitrate, phenylmercuric acetate, methyl/propylparabens, phenylethyl alcohol, sodium benzoate, sodium propionate, sorbic acid, and sodium perborate. The amount of preservative in the solution can be a level that enhances the shelf life, limits bacterial growth, or otherwise preserves the composition (e.g., ophthalmic composition, subcutaneous, etc.) with minimal toxicity to the affected tissues (see, e.g., The United States Pharmacopeia, 22nd rev., and The National Formulary, 17th Ed. Rockville, MD). Levels of preservative suitable for use in the compositions herein can be determined by the person skilled in the art. In some embodiments, the preservatives can be used at an amount of from about 0.001% to about 1.0% w/v. For example, the preservative is present from about 0.005% to about 0.05% w/v, 0.005% to about 0.04% w/v, 0.01% to about 0.03% w/v, 0.01% to about 0.02% w/v, or from about 0.01% to about 0.015% w/v. In some embodiments, the amount of preservative can be about 0.005% w/v, about 0.01% w/v, about 0.012% w/v, about 0.014% w/v, about 0.016% w/v, about 0.018% w/v, about 0.02% w/v, about 0.03% w/v, about 0.04% w/v, or about 0.05% w/v. In some embodiments, no preservatives are used in the compositions.

The pharmaceutical compositions described herein can be prepared by the guidance provided herein and standard techniques, such as described in Remington: The Science and Practice of Pharmacy, 21st Ed. (2005).

1.12. Kits

In another aspect, the MTX composition is provided in the form of a kit. In some embodiments, the MTX composition in the kit is provided in a multi-dose vial. In some embodiments, the MTX composition in the kit is provided as single use vials. In some embodiments, the kit comprises one or more single use vials of the MTX composition. In some embodiments, the MTX composition is provided in the form of a dry composition for reconstitution with an appropriate solvent, such as pyrogen free sterile water or buffer. In some embodiments, the kit when provided as a dry composition includes a vial of solvent for reconstitution of MTX solution for injection.

In some embodiments, the kit further comprises a syringe for injection of the MTX composition. In some embodiments, the kit includes one or more syringes for injection of the MTX composition. In some embodiments, the MTX composition is provided in pre-filled syringes for administration into an eye of a subject.

In certain embodiments, the kit also includes prescribing information for proper use of the compositions. The information may be in the form of printed material or on a computer readable medium.

The following examples are provided to further illustrate the embodiments of the present disclosure. The examples described are illustrative only and are not intended to limit the scope of the invention in any way.

EXAMPLES

Example 1. Preparation of Compositions and Assessment of Transit Through Silicone Oil Water is placed in a suitable container, and each ingredient, e.g., surfactants, buffer, density building agent, methotrexate, etc., as appropriate for the formulation is added and dissolved in the solution one at a time. The pH is adjusted to 7.4±0.2 by addition of 1M sodium hydroxide or HCl. Water is added to make up to the desired final volume.

The impact of formulation composition on the travel time of the methotrexate through silicone layers of varying viscosity and amount was investigated using two grades of silicone oil: Polydimethyl siloxane 1,000 cps (Sigma Aldrich, UK) and 5,000 cps (Mistral industrial chemicals, UK).

1. Two heights of silicone oil were tested: 0.5 cm or 1 cm of oil was placed on top of 2 mL PBS buffer to confirm best height to use.
2. A drop of formulation (~50 mg) was placed at the top of silicone layer. The time taken for the API (formulation drop, yellow in color) to travel was monitored (cm/min), as well as visual observations for the distribution of the formulation phase into aqueous phase after traveling through the silicone phase, e.g., spontaneous, slow, etc.

The transit times of several different formulations examined are provided in FIG. 1.

As a further example, the following formulation was prepared.

|  | Target | Range |
| --- | --- | --- |
| Methotrexate | 8 mg/ml (0.8% w/v) | 7.2-8.8 mgml (90-110%) |
| Sucrose | 75 mg/ml (75% w/v) | 71.25-78.75 (95%-105% |
| pH | 7.1-8.1 | 7.0-9.0 |
| Osmolality | 250-350 mOsm |  |

Several of the formulations were also assessed for the number of times the formulation passes through the oil interface within a 2 h time period. Each formulation was measured for a maximum of 2 h and the results represent the number of times the formulation passed across the silicone oil-PBS buffer interface in the assessed time period. The total number of times at both heights and both viscosities (out of 9 tests) and the % is provided in the table below.

TABLE 1

| | Silicone Oil | | | | |
| --- | --- | --- | --- | --- | --- |
| | 1000 centistoke | | 5000 centistoke | | No. of times crossed interface |
| Formulation | 0.5 mL | 1 mL | 0.5 mL | 1 mL | (%) |
| F1 | 1 | 0 | 1 | 1 | 3 out of 12 (25%) |
| F4 | 1 | 2 | 2 | 2 | 7 out of 12 (58%) |
| F5 | 1 | 2 | 3 | 3 | 9 out of 12 (75%) |
| F6 | 2 | 2 | 3 | 2 | 9 out of 12 (75%) |

Example 2. Efficacy Comparative Clinical Study

Recent pilot studies have shown intravitreal methotrexate (MTX) and intravitreal ranibizumab (Lucentis®, Genentech Inc., San Francisco, CA) to be promising treatments for uveitic ME, and intravitreal dexamethasone implant (Ozurdex®, Allergan, Irvine, CA) has recently been approved by the U.S. FDA for uveitic ME in patients with non-infectious uveitis. In addition to being effective, intravitreal MTX and ranibizumab potentially may have less ocular side effects than corticosteroids, particularly less intraocular pressure (IOP) elevation. However, the relative efficacy of these treatments was previously unknown. The Macular Edema Ranibizumab v. Intravitreal anti-inflammatory Therapy (MERIT) Trial compared the relative efficacy and safety of intravitreal methotrexate, ranibizumab, and dexamethasone implant. The MERIT study was a parallel design (1:1:1), randomized comparative effectiveness trial with an anniversary close-out at the 6 month clinic visit. The primary outcome is percent change in central subfield thickness from the baseline OCT measurement to the 12 week visit.

Active Comparator: Dexamethasone intravitreal implant 0.7 mg

Eligible eye(s) treated at study visit MO1 (week 0).

Retreatment required at study visit M03 (8 weeks) if re-treatment criteria met.

Retreatment permitted at later time points if retreatment criteria met.

Re-Treatment Criteria:
1. Central subfield thickness greater than 1.1× upper limit of normal (330 μm for Zeiss and Topcon SD OCT and 352 μm for Heidelberg OCT) and/or cystoid space(s) within 1 mm central subfield.

2. IOP of <25 mm Hg (treatment with ≤3 IOP-lowering agents permitted) Minimum time between treatments: minimum target is 8 weeks after last injection but re-injection permitted as early as 51 days after last injection;
Drug: Dexamethasone intravitreal implant 0.7 mg
Standard preparation as described for intravitreal injections.
Other Name: Ozurdex
Active Comparator: Intravitreal ranibizumab 0.5 mg in 0.05 mL
Eligible eye(s) treated at study visits MO1 (week 0), M02 (4 weeks), and M03 (8 weeks).
Retreatment permitted at M04 (12 weeks) and at later time points if retreatment criteria met.
Minimum time between treatments: minimum target is 4 weeks after last injection but re-injection permitted as early as 23 days after last injection.
Re-treatment permitted at later time points if re-treatment criteria met.
Drug: Intravitreal Ranibizumab 0.5 mg
Intravitreal Ranibizumab 0.5 mg injection procedures should be carried out under controlled aseptic conditions which include the use of sterile gloves and a sterile eyelid speculum (or equivalent). Adequate anesthesia and a broad-spectrum microbicide such as betadine, applied to the periocular skin, eyelid and ocular surface are required prior to the injection.
Other Name: Lucentis
Active Comparator: Intravitreal methotrexate 400 µg in 0.1 mL
Eligible eye(s) treated at study visit M01 (week 0).
Retreatment required at M02 (4 weeks) and M03 (8 weeks) if retreatment criteria met.
Retreatment permitted at later time points if retreatment criteria met.
Minimum time between treatments: minimum target is 4 weeks after last injection but re-injection permitted as early as 23 days after last injection.
Drug: Intravitreal Methotrexate 400 µg
Intravitreal Methotrexate 400 µg injection procedures should be carried out under controlled aseptic conditions which include the use of sterile gloves and a sterile eyelid speculum (or equivalent). Adequate anesthesia and a broad-spectrum microbicide such as betadine, applied to the periocular skin, eyelid and ocular surface are required prior to the injection.
Primary Outcome Measures:
Percent change in central subfield thickness from the baseline OCT measurement [Time Frame: At 12-week visit]
The primary outcome is the percent change in central subfield thickness from the baseline OCT measurement at the 12-week visit. The assessment of OCT outcomes will be performed by masked readers. The 12-week visit was chosen as the time to assess the primary outcome because the ranibizumab treatment arm specifies injections at baseline, 4 weeks and 8 weeks in all participants, and because the peak benefit for the dexamethasone pellet appears to be at 8 to 12 weeks.
Secondary Outcome Measures:
1. IOP Elevation of >=24 mm Hg [Time Frame: During 24 weeks of follow-up]
Rate of IOP elevation of >=24 mm Hg during follow-up.
2. IOP Elevation of >=30 mm Hg [Time Frame: During 24 weeks of follow-up]
Rate of IOP elevation of >=30 mm Hg during follow-up
3. IOP Elevation of >=10 mm Hg From Baseline [Time Frame: During 24 weeks of follow-up]
Rate of IOP elevation of >=10 mm Hg from baseline
4. Change in Macular Thickness as Measured by OCT [Time Frame: Over 24 weeks of follow-up]
Percent change in macular thickness as measured by OCT
5. >=20% Reduction in Macular Thickness (or Normalization Even if <20% Reduction [Time Frame: Over 24 weeks of follow-up]
Proportion of eyes with >=20% reduction in macular thickness (or normalization of macular thickness even if there is <20% reduction)
6. Resolution of macular edema [Time Frame: Over 24 weeks of follow-up]
Proportion of eyes with resolution of macular edema defined as normalization of the macular thickness, i.e., <260 um on the standard scale
7. Change in Best-corrected Visual Acuity [Time Frame: Over 24 weeks of follow-up]
Mean change in best-corrected visual acuity
8. Vitreous Hemorrhage [Time Frame: During 24 weeks of follow-up]
Count of vitreous hemorrhage as an immediate complication of injection
9. Retinal Tear/Detachment [Time Frame: During 24 weeks of follow-up]
Count of retinal tears/detachments
10. Endophthalmitis [Time Frame: During 24 weeks of follow-up]
Occurrence of endophthalmitis
11. Severe vision loss [Time Frame: During 24 weeks of follow-up]
Severe vision loss (>=15 standard letters)
Ages Eligible for Study: 18 Years and older (Adult, Older Adult)
Sexes Eligible for Study: All
Accepts Healthy Volunteers: No
Criteria
Inclusion criteria:
Patient level inclusion criterion
1. 18 years of age or older;
Eye level inclusion criteria—at least one eye must meet all of the following conditions
2. Inactive or minimally active non-infectious anterior, intermediate, posterior or panuveitis, as defined by SUN132 criteria as ≤0.5+ anterior chamber cells, ≤0.5+ vitreous haze grade and no active retinal/choroidal lesions for a minimum of 4 weeks;
3. Macular edema (ME) defined as the presence of macular thickness greater than the normal range for the OCT machine being used (see cut points below), regardless of the presence of cysts, following an intravitreal corticosteroid injection (≥4 weeks following intravitreal triamcinolone injection or ≥12 weeks following intravitreal dexamethasone implant injection); Greater than 300 µm for Zeiss Cirrus Greater than 320 µm for Heidelberg Spectralis Greater than 300 µm for Topcon 3DOCT
4. Baseline fluorescein angiogram that, as assessed by the study ophthalmologist, is gradable for degree of leakage in the central subfield;
5. Best corrected visual acuity (BCVA) 5/200 or better;
6. Baseline intraocular pressure>5 mm Hg and ≤21 mm Hg (current use of ≤3 intraocular pressure-lowering medications and/or prior glaucoma surgery are acceptable (Note: combination medications, e.g., Combigan, are counted as two IOP-lowering medications);

7. Media clarity and pupillary dilation sufficient to allow OCT testing and assessment of the fundus.

Exclusion criteria:

Patient level exclusion criteria

1. History of infectious uveitis in either eye;
2. History of infectious scleritis of any type in either eye (Note: History of noninfectious scleritis that has been active in past 12 months is an eye-level exclusion; see #13 below);
3. History of keratitis (with the exception of keratitis due to dry eye) in either eye;
4. History of central serous retinopathy in either eye;
5. Active infectious conjunctivitis in either eye;
6. Oral prednisone dose>10 mg per day (or of an alternative corticosteroid at a dose higher than that equipotent to prednisone 10 mg per day) OR oral prednisone dose≤10 mg per day at baseline that has not been stable for at least 4 weeks (note: if patient is off of oral prednisone at baseline (M01 study visit) dose stability requirement for past 4 weeks does not apply);
7. Systemic immunosuppressive drug therapy that has not been stable for at least 4 weeks (note: use of systemic methotrexate is acceptable as long as regimen has been stable for at least 4 weeks);
8. Use of oral acetazolamide or other systemic carbonic anhydrase inhibitor at baseline;
9. Known allergy or hypersensitivity to any component of the study drugs;
10. For women of childbearing potential: pregnancy, breastfeeding, or a positive pregnancy test; unwilling to practice an adequate birth control method (abstinence, combination barrier and spermicide, or hormonal) for duration of trial;

Eye level exclusion criteria—at least one eye that meets all inclusion criteria cannot have any of the following conditions 11. History of infectious endophthalmitis;
12. History of severe glaucoma as defined by optic nerve damage (cup/disc ratio of ≥0.9 or any notching of optic nerve to the rim);
13. History of active noninfectious scleritis in past 12 months (Note: History of noninfectious scleritis is acceptable if the last episode of active scleritis resolved at least 12 months prior to enrollment);
14. Presence of an epiretinal membrane noted clinically or by OCT that per the judgment of study ophthalmologist may be significant enough to limit improvement of ME (i.e., causing substantial wrinkling of the retinal surface);
15. Torn or ruptured posterior lens capsule
16. Presence of silicone oil;
17. Ozurdex administered in past 12 weeks;
18. Anti-VEGF agent, intravitreal methotrexate, or intravitreal/periocular corticosteroid administered in past 4 weeks;
19. Fluocinolone acetonide implant (Retisert) placed in past 3 years.

Results

In the GUARD trial, methotrexate (MTX) was statistically superior to historical control (Ophthalmology 124(6): 757-767, 2017; Archives of Ophthalmology 25(9):1161-7, 2007) for the prevention of retinal detachment due to PVR over six months (P=0.024). PVR patients have a high unmet medical need due to the lack of treatment options. PVR is particularly difficult to treat. The MTX intravitreal formulation used in the presently described clinical trial was preservative-free, designed to be vitreous-compatible, and optimized for excipient composition, viscosity, density, tonicity, pH, concentration, and volume of administration.

Part 1 of the GUARD Trial was designed to assess the preliminary activity of a novel vitreous-compatible formulation of methotrexate, versus historical control and routine surgical care without therapy in patients with PVR. Sixty-eight patients received MTX, and 38 patients received routine surgical care. Relative to historical control, statistically significant reduction (P=0.024) in retinal detachment over six months was observed following serial intravitreal injection of MTX. Although not statistically powered for secondary or exploratory endpoints, the results of the GUARD Trial demonstrated numerical superiority of MTX over routine surgical care in reducing the dichotomous endpoints of retinal detachment rate over six months, hypotony (low intraocular pressure), complete retinal attachment by six months, macular attachment by six months, and epiretinal membrane formation (overall P=0.047). Visual acuity was similar between MTX treatment and routine surgical care groups. Central macular thickness was numerically lower in MTX-treated patients. No safety signals were observed in the trial, and MTX was well tolerated; there were no observed treatment-emergent serious adverse events.

|  | ADX-2191 (methotrexate, MTX) (n = 68) | Historical Control[†] (n = 292) |
|---|---|---|
| Patients with retinal detachment within 6 months of surgery | 16 | 113 |
| Odds ratio (95% CI) vs. historical control | 0.49 (0.26, 0.89) | |
| P value vs. historical control* | 0.024 | |

[†]Ophthalmology 124(6): 757-767, 2017; Archives of Ophthalmology 25(9): 1161-7, 2007.
*Fisher exact test.
CI = confidence interval.
ADX-2191 (methotrexate injection, USP) for intravitreal administration is an investigational drug candidate.

|  | ADX-2191 (n = 68) | Routine Surgical Care (n = 38) |
|---|---|---|
| Letters of visual acuity (SD) | 32.9 (19.7) | 36.5 (25.0) |
| Central macular subfield thickness (μM, SD) | 382 (182) | 484 (233) |

The most common adverse event associated with MTX treatment was punctate keratitis, a well-known side effect of intravitreal methotrexate, that was most commonly mild in severity. The most common adverse event associated with ADX-2191 administration was punctate keratitis (n=11, 16%), a well-known side effect of intravitreal methotrexate. Nine events were mild; two were moderate. The incidence of punctate keratitis was substantially less than that previously reported (58%) for intravitreal methotrexate. See Annals of Hematology, 95(4), 593-601, 2016.

Across all other treatment-emergent adverse events occurring in at least 10% of patients in either treatment arm, relative to patients treated with routine surgical care, MTX-treated patients had numerically fewer side effects, including pain, cystoid macular edema, corneal edema, macular fibrosis, corneal epithelial defects, anterior uveitis, ocular hypertension, and post-operative inflammation (overall P=0.0002). In the MTX group, there was one discontinuation, which was due to scheduling difficulties.

In addition, it is well known that improper compounding practices can result in serious drug quality problems such as contamination, or excessive amounts of active ingredient, both of which can lead to patient injury and death (fda.gov/drugs/human-drug-compounding/compounding-and-fda-questions-and-answers). Sterile endophthalmitis is an infrequent complication of intravitreal injections but has been observed in the context of compounded drugs that have not been approved for intravitreal administration (Marticorena et al. 2012). From the studies administering compounded methotrexate, 5 patients were observed to have mild to severe inflammatory reactions that were described as sterile endophthalmitis (Frenkel et al. 2008, Habot-Wilner et al. 2021, Ma et al. 2016, Smith et al. 2002). In a prospective study evaluating methotrexate administered in post-operative eyes at risk for proliferative vitreoretinopathy (PVR) (Study ADX-2191-PVR-001, the GUARD Trial), no events of sterile or infectious endophthalmitis occurred.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

We claim:

1. A method of treating retinitis pigmentosa (RP), comprising administering intravitreally to a subject in need thereof a composition comprising methotrexate at a concentration of about 5 mg/mL to about 12 mg/mL; sucrose at a concentration of about 7% w/v to about 12% w/v; and a phosphate buffer; wherein the volume of composition administered is about 20 µL to about 300 µL wherein the composition is administered for inhibiting and relieving retinitis pigmentosa and the incidence of secondary punctate keratitis in the subject is reduced by about 10% to 50% compared to a similar subject administered a non-GMP composition of methotrexate or a composition comprising methotrexate in a volume greater than 300 µL.

2. The method of claim 1, wherein the volume of composition administered is 50 µL±10 µL.

3. The method of claim 1, wherein the incidence of secondary punctate keratitis in the subject is reduced by about 20% to 40% compared to a similar subject administered a non-GMP composition of methotrexate or a composition comprising methotrexate in a volume greater than 300 µL.

4. The method of claim 1, wherein the incidence of secondary punctate keratitis in the subject is reduced by about 40% compared to a similar subject administered a non-GMP composition of methotrexate or a composition comprising methotrexate in a volume greater than 300 µL.

5. The method of claim 4, wherein the method produces a statistically significant (p<0.05) reduction in incidence of punctate keratitis across a representative group of subjects.

6. The method of claim 5, wherein the volume of composition administered is about 20 µL to about 80 µL.

7. The method of claim 5, wherein the volume of composition administered is 50 µL±10 µL.

8. The method of claim 1, wherein the method provides an improved incidence of intraocular pressure (IOP) elevation (hypotony) compared to a similar subject administered a non-GMP composition of methotrexate or a composition comprising methotrexate in a volume greater than 300 µL.

9. The method of claim 1, wherein the composition has a transit rate of less than 10 min in 1 mL of silicone oil (SiO) having a viscosity of at least 1000 centistoke and depth of 1 cm.

10. The method of claim 9, wherein the transit rate is less than 8 min.

11. The method of claim 10, wherein the SiO is polydimethyl siloxane 5000 centistoke oil or polydimethyl siloxane 1000 centistoke oil.

12. The method of claim 1, wherein the methotrexate is at a concentration of about 7 mg/mL to about 9 mg/mL.

13. The method of claim 1, wherein the composition has a density of about 1.0 to about 1.20 g/cm$^3$ at 20° C.

14. The method of claim 12, wherein the sucrose is at a concentration of about 7.0% w/v to about 8% w/v.

15. The method of claim 14, wherein the phosphate buffer is sodium phosphate dibasic, and the composition has a pH of about 6 to about 8.

16. The method of claim 1, wherein the subject has a prior history of one or more of: chronic ocular inflammation, infectious retinitis, multiple retinal detachments, large retinal breaks or giant retinal tears, multiple retinal breaks, ocular trauma, retinal detachment associated with vitreous hemorrhage, and choroidal detachment; and combinations thereof.

17. The method of claim 14, wherein each dose of methotrexate is independently about 200 µg to about 600 µg, or about 300 µg to about 500 µg.

18. The method of claim 14, wherein each dose of methotrexate is independently about 200 µg, about 300 µg, about 400 µg, or about 500 µg.

19. The method of claim 1, wherein the composition is administered once a month.

20. The method of claim 7, wherein the composition is administered once a month and the dose of methotrexate is about 400 µg.

* * * * *